US007329510B2

(12) United States Patent
Morrow et al.

(10) Patent No.: US 7,329,510 B2
(45) Date of Patent: Feb. 12, 2008

(54) FULL LENGTH HUMAN HCN1I$_H$ CHANNEL SUBUNIT AND VARIANTS

(75) Inventors: John Anthony Morrow, Edinburgh (GB); Donald Robert Dunbar, Linlithgow (GB); Deborah Grace Tolan, Gourock (GB)

(73) Assignee: N.V. Organon, Oss (NL)

( * ) Notice: Subject to any disclaimer, the term of this patent is extended or adjusted under 35 U.S.C. 154(b) by 478 days.

(21) Appl. No.: 10/296,270

(22) PCT Filed: May 22, 2001

(86) PCT No.: PCT/EP01/05959

§ 371 (c)(1), (2), (4) Date: Nov. 22, 2002

(87) PCT Pub. No.: WO01/90142

PCT Pub. Date: Nov. 29, 2001

(65) Prior Publication Data

US 2003/0180753 A1 Sep. 25, 2003

(30) Foreign Application Priority Data

May 24, 2000 (EP) ................................. 00304420
Apr. 12, 2001 (EP) ................................. 01201344

(51) Int. Cl.
*C12N 15/00* (2006.01)
*C12N 5/00* (2006.01)
*G01N 33/53* (2006.01)

(52) U.S. Cl. .................. 435/69.1; 435/320.1; 435/325; 435/7.8; 530/350

(58) Field of Classification Search ............... 435/69.1, 435/320.1, 7.8; 536/23.1
See application file for complete search history.

(56) References Cited

FOREIGN PATENT DOCUMENTS

WO 99 32615 A 7/1999
WO 02 02630 A 1/2002

OTHER PUBLICATIONS

Wells. Additivity of mutatonal effects in proteins. Biochemistry. vol. 29/37:8509-8517 (1990).*

Santoro B et al: "Identification of a gene encoding a hyperpolarization-activated pacemaker channel of brain". Cell. US. Cell Press. vol. 93. May 29, 1998. pp. 717-729.

Ludwig et al: "Two pacemaker channels from human heart with profoundly different activation kinetics.", EMBO Journal. vol. 18. No. 9. May 4, 1999. pp. 2323-2329.

Attwell et al., "Behaviour of the Rod Network in the Tiger Salamander Retina Mediated by Membrane Properties of Individual Rods," Journal of Physiology 309 (1980) 287-315.

Bader et. al., "Effect of Changes in Intra- and Extracellular Sodium on the Inward (Anomalous) Rectification in Salamander Photoreceptors," *Journal of Physiology* 347 (1984) 611-631.

Bal et. al., "Synchronized Oscillations in the Inferior Olive are Controlled by the Hyperpolarization-Activated Cation Current /η," *Journal of Neurophysiology* 77 (1997) 3145-3156.

Bal et. al., "What Stops Synchronized Thalamocortical Oscillations?" *Neuron* 17 (1996) 297-308.

Barnes et. al., "Ionic Channels of the Inner Segment of Tiger Salamander Cone Photoreceptors," Journal of General Physiology 94 (1989) 719-743.

Beaumont et. al., "Enhancement of synaptic transmission by cyclic AMP modulation of presynaptic ih channels," Nature Neuroscience 3 (2000) 133-141.

Brown et. al., "The Hyperpolarization-activated Inward Channel and Cardiac Pacemaker Activity," in *Molecular Physiology and Pharmacology of Cardiac Ion Channels and Transporters*, Marad et al., eds., (1996) 17-30.

Clapham, D.E., "Not So Funny Anymore: Pacing Channels Are Cloned," *Neuron* 21 (1998) 5-7.

DiFrancesco, D., "Pacemaker Mechanisms in Cardiac Tissue," *Annual Review of Physiology* 55 (1993) 455-472.

DiFrancesco, D., "A New Interpretation of the Pace-Maker Current in Calf Purkinje Fibres," Journal of Physiology 314 (1981) 359-376.

DiFrancesco, D., "The Hyperpolarization-activated (λ) Current: Autonomic regulation and the Control of Pacing," in *Molecular Physiology and Pharmacology of Cardiac Ion Channels and Transporters*, Marad et al., eds., (1996) 31-37.

DiFrancesco et. al., "Modulation of Single Hyperpolarization-Activated channels (/λ) by cAMP in the Rabbit Sino-Atrial Node," Journal of Physiology 474 (1994) 473-482.

Gasparini et. al., "Action of the hyperpolarization-activated current (/λ) blocker ZD 7288 in hippocampal CA1 neurons," *Pflugers Archiv - European Journal of Physiology* 435 (1997) 99-106.

Gauss et. al., "Molecular identification of a hyperpolarization-activated channel in sea urchin sperm," *Nature* 393 (1998) 583-587.

Halliwell et. al., "Voltage-Clamp Analysis of Muscarinic Excitation in Hippocampal Neurons," *Brain Research* 250 (1982) 71-92.

Harris et. al., "Mechanism of Block by ZD 7288 of the Hyperpolarization-Activated Inward Rectifying Current in Guinea Pig Substantia Nigra Neurons in Vitro," *Journal of Neurophysiology* 74 (1995) 2366-2378.

(Continued)

*Primary Examiner*—Marianne P. Allen
*Assistant Examiner*—Regina M. DeBerry
(74) *Attorney, Agent, or Firm*—Susan Hess

(57) ABSTRACT

This invention relates to a DNA sequence encoding a member of the hyperpolarized activated ion channel family (HCN) and variants thereof, and the use of said sequences in assays for the measurement of gene expression. It also relates to assays for screening of $I_h$ activators and blockers for clinical and therapeutic use in the management of human psychiatric and neurological dysfunction in the CNS, cardiovascular dysfunction of the heart, and reproductive dysfunction and/or contraception related to $I_h$ function in testes and spermatozoa. Further, antibodies against the expressed DNA sequences and other compounds reactive with the expressed DNA sequence are also part of the invention.

10 Claims, 10 Drawing Sheets

OTHER PUBLICATIONS

Lipman et al., "Rapid and Sensitive Protein Similarity Searches," Science 227 (1985) 1435-1441.
Ludwig et al., "A family of hyperpolarization-activated mammalian cation channels,"*Nature* 393 (1998) 587-591.
Luthi et. al., "H-Current: Properties of a Neuronal and Network Pacemaker," *Neuron* 21 (1998) 9-12.
Maccaferri et. al., "The Hyperpolarization-Activated Current (/λ) and its Contribution to Pacemaker Activity in Rat CA1 Hippocampal Stratum oriens-alveus Interneurones," *Journal of Physiology* 497 (1996) 119-130.
Magee, J.C., "Dendritic /λnormalizes temporal summation in hippocampal CA1 neurons," *Nature Neuroscience* 2 (1999) 508-514.
McCormick et. al., "Properties of a Hyperpolarization-Activated cation current and its Role in Rhythmic Oscillation in Thalamic Relay Neurones," *Journal of Physiology* 431 (1990) 291-318.
Moosmang et. al., "Differential Distribution of Four Hyperpolarization-Activated Cation Channels in Mouse Brain," *Biol. Chem.* 380 (1999) 975-980.
Pape, H.C., "Queer Current and Pacemaker: The Hyperpolarization-Activated Cation Current in Neurons," *Annual Review of Physiology* 58 (1996) 299-327.
Rekling et. al., "Prebotzinger Complex and Pacemaker Neurons: Hypothesized Site and Kernel for Respiratory Rhythm Generation," *Annual Review of Physiology* 60 (1998) 385-405.
Ross et. al., "Polyglutamine Pathogenesis," *Philosophical Transactions of the Royal Society of London - Series B: Biological Sciences* 354 (1999) 1005-1011.
Saiki et. al., "Analysis of Enzymatically Amplified β-globin and HLA-DQα DNA with Allele-Specific Oligonucleotide Probes, " *Nature* 324 (1986) 163-166.
Santoro et. al., "Interactive Cloning with the SH3 Domain of N-src identifies a New Brain Specific Ion Channel Protein, with Homology to Eag and Cyclic Nucleotide-Gated Channels," *Proc. Natl. Acad. Sci. USA* 94 (1997) 14815-14820.
Seifert et. al., "Molecular Characterization of a Slowly Gating Human Hyperpolarization-Activated Channel Predominantly Expressed in Thalamus, Heart, and Testis," *Proc. Natl. Acad. Sci. USA* 96 (1999) 9391-9396.
Smith et al., "Identification of Common Molecular Subsequences," *J. Mol. Biol.* 147 (1981) 195-197.
Stoesser et. al., "The EMBL Nucleotide Sequence Database," *Nucleic Acids Research* 27 (1999) 18-24.
Strata et. al., "A Pacemaker Current in Dye-Coupled Hilar Interneurons Contributes to the Generation of Giant GABAergic Potentials in Developing Hippocampus," *Journal of Neuroscience* 17 (1997) 1435-1446.
Wickman et. al., "Abnormal Heart Rate Regulation in *GIRK*4 Knockout Mice," *Neuron* 20 (1998) 103-114.

* cited by examiner

Figure 1

```
SEQ_ID_NO_2     MEGGGK-PNSSSNSRDDG-NSVFP----AKA-------SAP--GAG----PAAAE-K-R-
SEQ_ID_NO_4     MEGGGK-PNSSSNSRDDG-NSVFP----AKA-------SAP--GAG----PAAAE-K-R-
SEQ_ID_NO_6     MEGGGK-PNSSSNSRDDG-NSVFP----AKA-------SAT--GAG----PAAAE-K-R-
SEQ_ID_NO_8     MEGGGK-PNSSSNSRDDG-NSVFP----AKA-------SAT--GAG----PAAAE-K-R-
human_HCN1      ------------------------------------------------------------
human_HCN2      MDA--R-G-GGG--RP-G-ES--P---GA-T-------PAP--GPPPPPPPAPPQ-Q-QP
human_HCN4      MD---KLP-PSM--RK-RLYSL-PQQVGAKAWIMDEEEDAEEEGAGGRQDPSRRSIRLRP

SEQ_ID_NO_2     LGTP-P-G---G-G---------G-A-G---AK-E----H--GN-SV---C--FKVDG--
SEQ_ID_NO_4     LGTP-P-G---G-G---------G-A-G---AK-E----H--GN-SV---C--FKVDG--
SEQ_ID_NO_6     LGTP-P-G---G-G---------G-A-G---AK-E----H--GN-SV---C--FKVDG--
SEQ_ID_NO_8     LGTP-P-G---G-G---------G-A-G---AK-E----H--GN-SV---C--FKVDG--
human_HCN1      ------------------------------------------------------------
human_HCN2      -PPPPPPAPPPGPGPAPPQHPPRAEALPPEAAD-EGGP-R--GR------LRS-R-DS--
human_HCN4      LPSPSPSAAA-G-G-T--ES--RSSALG--AADSEG-PARGAGKSSTNGDCRRFR-GSLA

SEQ_ID_NO_2     --G--GG--G-GG-G-G---G-----G------GE-E--PAG------G-----------
SEQ_ID_NO_4     --G--GG--G-GG-G-G---G-----G------GE-E--PAG------G-----------
SEQ_ID_NO_6     --G--GG--G-GG-G-G---G-----G------GE-E--PAG------G-----------
SEQ_ID_NO_8     --G--GG--G-GG-G-G---G-----G------GE-E--PAG------G-----------
human_HCN1      ------------------------------------------------------------
human_HCN2      SCG-RPGTPGAASTAKGSPNG---ECG--R---GEPQCSPAG---PEG----PARGPKV
human_HCN4      SLGSRGG--GSGGTGSGSSHGHLHDSAEERRLIAEGDASP-GEDRTPPGLAAEPER-PG-

SEQ_ID_NO_2     -F----------------------ED-A-------E-G--------P----R-R-QYGFM
SEQ_ID_NO_4     -F----------------------ED-A-------E-G--------P----R-R-QYGFM
SEQ_ID_NO_6     -F----------------------ED-A-------E-G--------P----R-R-QYGFM
SEQ_ID_NO_8     -F----------------------ED-A-------E-G--------P----R-R-QYGFM
human_HCN1      ------------------------------------------------------------
human_HCN2      SFSCRGAASGPAPG--PGPA----EE-A-GS--E-EAG-PAGE---P----R-GSQASFM
human_HCN4      A-SAQPAASPPPPQQPPQPASASCEQPSVDTAIKVEGGAAAGDQILPEAEVRLG-QAGFM

SEQ_ID_NO_2     QRQFTSMLQPGVNKFSLRMFGSQKAVEKEQERVKTAGFWIIHPYSDFRFYWDLIMLIMMV
SEQ_ID_NO_4     QRQFTSMLQPGVNKFSLRMFGSQKAVEKEQERVKTAGFWIIHPYSDFRFYWDLIMLIMMV
SEQ_ID_NO_6     QRQFTSMLQPGVNKFSLRMFGSQKAVEKEQERVKTAGFWIIHPYSDFRFYWDLIMLIMMV
SEQ_ID_NO_8     QRQFTSMLQPGVNKFSLRMFGSQKAVEKEQERVKTAGFWIIHPYSDFRFYWDLIMLIMMV
human_HCN1      ---------------------------KEQERVKTAGFWIIHPYSDFRFYWDLIMLIMMV
human_HCN2      QRQFGALLQPGVNKFSLRMFGSQKAVEREQERVKSAGAWIIHPYSDFRFYWDFTMLLFMV
human_HCN4      QRQFGAMLQPGVNKFSLRMFGSQKAVEREQERVKSAGFWIIHPYSDFRFYWDLTMLLIMV
                                           .******.** **************  **. **
                                                                      S1

SEQ_ID_NO_2     GNLVIIPVGITFFTEQ-TTTPWIIFNVASDTVFLLDLIMNFRTGTVNEDSSEIILDP-KV
SEQ_ID_NO_4     GNLVIIPVGITFFTEQ-TTTPWIIFNVASDTVFLLDLIMNFRTGTVNEDSSEIILDP-KV
SEQ_ID_NO_6     GNLVIIPVGITFFTEQ-TTTPWIIFNVASDTVFLLDLIMNFRTGTVNEDSSEIILDP-KV
SEQ_ID_NO_8     GNLVIIPVGITFFTEQ-TTTPWIIFNVASDTVFLLDLIMNFRTGTVNEDSSEIILDP-KV
human_HCN1      GNLVIIPVGITFFTEQ-TTTPWIIFNVASDTVFLLDLIMNFRTGTVNEDSSEIILDP-KV
human_HCN2      GNLIIIPVGITFFKDE-TTAPWIVFNVVSDTFFLMDLVLNFRTGIVIEDNTEIILDPEK-
human_HCN4      GNLIIIPVGITFFKDENTT-PWIVFNVVSDTFFLIDLVLNFRTGIVVEDNTEIILDPQR-
                ***.********* .. ** ***.*** *** **.**..***** * ** .****** . 
                                          S2

SEQ_ID_NO_2     IKMNYLKSWFVVDFISSIPVDYIFLIVE-KGMDSEVYKTARALRIVRFTKILSLLRLLRL
SEQ_ID_NO_4     IKMNYLKSWFVVDFISSIPVDYIFLIVE-KGMDSEVYKTARALRIVRFTKILSLLRLLRL
SEQ_ID_NO_6     IKMNYLKSWFVVDFISSIPVDYIFLIVE-KGMDSEVYKTARALRIVRFTKILSLLRLLRL
SEQ_ID_NO_8     IKMNYLKSWFVVDFISSIPVDYIFLIVE-KGMDSEVYKTARALRIVRFTKILSLLRLLRL
human_HCN1      IKMNYLKSWFVVDFISSIPVDYIFLIVE-KGMDSEVYKTARALRIVRFTKILSLLRLLRL
human_HCN2      IKKKYLRTWFVVDFVSSIPVDYIFLIVE-KGIDSEVYKTARALRIVRFTKILSLLRLLRL
human_HCN4      IKMKYLKSWFMVDFISSIPVDYIFLIVETR-IDSEVYKTARALRIVRFTKILSLLRLLRL
                **  **..**.***.************* . .****************************
                        S3                                  S4

SEQ_ID_NO_2     SRLIRYIHQWEEIFHMTYDLASAVVRIFNLIGMMLLLCHWDGCLQFLVPLLQDFPPDCWV
SEQ_ID_NO_4     SRLIRYIHQWEEIFHMTYDLASAVVRIFNLIGMMLLLCHWDGCLQFLVPLLQDFPPDCWV
SEQ_ID_NO_6     SRLIRYIHQWEEIFHMTYDLASAVVRIFNLIGMMLLLCHWDGCLQFLVPLLQDFPPDCWV
SEQ_ID_NO_8     SRLIRYIHQWEEIFHMTYDLASAVVRIFNLIGMMLLLCHWDGCLQFLVPLLQDFPPDCWV
human_HCN1      SRLIRYIHQWEEIFHMTYDLASAVVRIFNLIGMMLLLCHWDGCLQFLVPLLQDFPPDCWV
human_HCN2      SRLIRYIHQWEEIFHMTYDLASAVMRICNLISMMLLLCHWDGCLQFLVPMLQDFPRNCWV
human_HCN4      SRLIRYIHQWEEIFHMTYDLASAVVRIVNLIGMMLLLCHWDGCLQFLVPMLQDFPDDCWV
                ************************.** *** *****************.*****  ***
                                                      S5
```

Figure 1 continued

```
SEQ_ID_NO_2    SLNEMVNDSWGKQYSYALFKAMSHMLCIGYGAQAPVSMSDLWITMLSMIVGATCYAMFVG
SEQ_ID_NO_4    SLNEMVNDSWGKQYSYALFKAMSHMLCIGYGAQAPVSMSDLWITMLSMIVGATCYAMFVG
SEQ_ID_NO_6    SLNEMVNDSWGKQYSYALFKAMSHMLCIGYGAQAPVSMSDLWITMLSMIVGATCYAMFVG
SEQ_ID_NO_8    SLNEHVNDSWGKQYSYALFKAMSHMLCIGYGAQAPVSMSDLWITMLSMIVGATCYAMFVG
human_HCN1     SLNEMVNDSWGKQYSYALFKAMSHMLCIGYGAQAPVSMSDLWITMLSMIVGATCYAMFVG
human_HCN2     SINGMVNHSWSELYSFALFKAMSHMLCIGYGRQAPESMTDIWLTMLSMIVGATCYAHFIG
human_HCN4     SINNMVNNSWGKQYSYALFKAMSHMLCIGYGRQAPVGMSDVWLTMLSMIVGATCYAMFIG
               *.* *** **    **.*************** ***  *.*.*.**************.*
                               Pore                            S6

SEQ_ID_NO_2    HATALIQSLDSSRRQYQEKYKQVEQYMSFHKLPADMRQKIHDYYEHRYQGKIFDEENILN
SEQ_ID_NO_4    HATALIQSLDSSRRQYQEKYKQVEQYMSFHKLPADMRQKIHDYYEHRYQGKIFDEENILN
SEQ_ID_NO_6    HATALIQSLDSSRRQYQEKYKQVEQYMSFHKLPADMRQKIHDYYEHRYQGKIFDEENILN
SEQ_ID_NO_8    HATALIQSLDSSRRQYQEKYKQVEQYMSFHKLPADMRQKIHDYYEHRYQGKIFDEENILN
human_HCN1     HATALIQSLDSSRRQYQEKYKQVEQYMSFHKLPADMRQKIHDYYEHRYQGKIFDEENILN
human_HCN2     HATALIQSLDSSRRQYQEKYKQVEQYMSFHKLPADFRQKIHDYYEHRYQGKMFDEDSILG
human_HCN4     HATALIQSLDSSRRQYQEKYKQVEQYMSFHKLPPDTRQRIHDYYEHRYQGKMFDEESILG
               ********************************* * **.************.***. **.

SEQ_ID_NO_2    ELNDPLREEIVNFNCRKLVATMPLFANADPNFVTAMLSKLRFEVFQPGDYIIREGAVGKK
SEQ_ID_NO_4    ELNDPLREEIVNFNCRKLVATMPLFANADPNFVTAMLSKLRFEVFQPGDYIIREGAVGKK
SEQ_ID_NO_6    ELNDPLREEIVNFNCRKLVATMPLFANADPNFVTAMLSKLRFEVFQPGDYIIREGAVGKK
SEQ_ID_NO_8    ELNDPLREEIVNFNCRKLVATMPLFANADPNFVTAMLSKLRFEVFQPGDYIIREGAVGKK
human_HCN1     ELNDPLREEIVNFNCRKLVATMPLFANADPNFVTAMLSKLRFEVFQPGDYIIREGAVGKK
human_HCN2     ELNGPLREEIVNFNCRKLVASMPLFANADPNFVTAMLTKLKFEVFQPGDYIIREGTIGKK
human_HCN4     ELSEPLREEIINFNCRKLVASMPLFANADPNFVTSMLTKLRFEVFQPGDYIIREGTIGKK
               **  ******.*********.*************.**.**.**************..***

SEQ_ID_NO_2    MYFIQHGVAGVITKSSKEMKLTDGSYFGEICLLTKGRRTASVRADTYCRLYSLSVDNFNE
SEQ_ID_NO_4    MYFIQHGVAGVITKSSKEMKLTDGSYFGEICLLTKGRRTASVRADTYCRLYSLSVDNFNE
SEQ_ID_NO_6    MYFIQHGVAGVITKSSKEMKLTDGSYFGEICLLTKGRRTASVRADTYCRLYSLSVDNFNE
SEQ_ID_NO_8    MYFIQHGVAGVITKSSKEMKLTDGSYFGEICLLTKGRRTASVRADTYCRLYSLSVDNFNE
human_HCN1     MYFIQHGVAGVITKSSKEMKLTDGSYFGEICLLTKGRRTASVRADTYCRLYSLSVDNFNE
human_HCN2     MYFIQHGVVSVLTKGNKEMKLSDGSYFGEICLLTRGRRTASVRADTYCRLYSLSVDNFNE
human_HCN4     MYFIQHGVVSVLTKGNKETKLADGSYFGEICLLTRGRRTASVRADTYCRLYSLSVDNFNE
               ********  *.**  ** **.***********.**************************
                                          CNBD

SEQ_ID_NO_2    VLEEYPMMRRAFETVAIDRLDRIGKKNSILLQKFQKDLNTGVFNNQENEILKQIVKHDRE
SEQ_ID_NO_4    VLEEYPMMRRAFETVAIDRLDRIGKKNSILLQKFQKDLNTGVFNNQENEILKQIVKHDRE
SEQ_ID_NO_6    VLEEYPMMRRAFETVAIDRLDRIGKKNSILLQKFQKDLNTGVFNNQENEILKQIVKHDRE
SEQ_ID_NO_8    VLEEYPMMRRAFETVAIDRLDRIGKKNSILLQKFQKDLNTGVFNNQENEILKQIVKHDRE
human_HCN1     VLEEYPMMRRAFETVAIDRLDRIGKKNSILLQKFQKDLNTGVFNNQENEILKQIVKHDRE
human_HCN2     VLEEYPMMRRAFETVAIDRLDRIGKKNSILLHKVQHDLNSGVFNNQENAIIQEIVKYDRE
human_HCN4     VLEEYPMMRRAFETVALDRLDRIGKKNSILLHKVQHDLNSGVFNYQENEIIQQIVQHDRE
               ****************.**************.* *.***.**** *** *...**. ***

SEQ_ID_NO_2    M------VQA-----------I------API-N----------------------Y--PQ
SEQ_ID_NO_4    M------VQA-----------I------API-N----------------------Y--PQ
SEQ_ID_NO_6    M------VQA-----------I------API-N----------------------Y--PQ
SEQ_ID_NO_8    M------VQA-----------I------API-N----------------------Y--PQ
human_HCN1     M------VQA-----------I------API-N----------------------Y--PQ
human_HCN2     M------VQ------------------QAELGQ----------------RV--GLF-PPP
human_HCN4     MAHCAHRVQAAASATPTPTPVIWTPLIQAPL-QAAAATTSVAIALTHHPRLPAAIFRPPP
               *      **                   *.  .                        .*

SEQ_ID_NO_2    ---M-------TT-----LNS--TS-----ST-TTP----T-SRMRT----Q--------
SEQ_ID_NO_4    ---M-------TT-----LNS--TS-----ST-TTP----T-SRMRT----Q--------
SEQ_ID_NO_6    ---M-------TT-----LNS--TS-----ST-TTP----T-SRMRT----Q--------
SEQ_ID_NO_8    ---M-------TT-----LNS--TS-----ST-TTP----T-SRMRT----Q--------
human_HCN1     ---M-------TT-----LNS--TS-----ST-TTP----T-SRMRT----Q--------
human_HCN2     ------------P----------P-------P---P-QV-T-SAIAT--LQQ-A---A-A
human_HCN4     GSGLGNLGAGQTPRHLKRLQSLIPSALGSASPASSPSQVDTPSS-SSFHIQQLAGFSAPA
                                                  *    * *   .    *

SEQ_ID_NO_2    --S-----------------P-----P--------V-----Y-TATS--LS--HSN-LHS
SEQ_ID_NO_4    --S-----------------P-----P--------V-----Y-TATS--LS--HSN-LHS
SEQ_ID_NO_6    --S-----------------P-----P--------V-----Y-TATS--LS--HSN-LHF
SEQ_ID_NO_8    --S-----------------P-----P--------V-----Y-TATS--LS--HSN-LHF
human_HCN1     --S-----------------P-----P--------V-----Y-TATS--LS--HSN-LHS
human_HCN2     -MS--F-----------C--PQVA-RP---L----V---GPL--ALG-------SPRLVR
human_HCN4     GLSPLLPSSSSSPPPGACGSPS-APTPSAGVAATTIAGFGHFHKALGGSLSSSDSP-LLT
                 *                 *     *        .        *         *  *
```

Figure 1 continued

```
SEQ_ID_NO_2     -P-SPSTQTPQ---PSAILSPCS-------------------------------------
SEQ_ID_NO_4     -P-SPSTQTPQ---PSAILSPCSYTTAV-C-S---PPVQSPLAARTFHYASPTASQLSLM
SEQ_ID_NO_6     -P-SPSTQTPQ---PSAILSPCS-------------------------------------
SEQ_ID_NO_8     -P-SPSTQTPQ---PSAILSPCSYTTAV-C-S---PPVQSPLAARTFHYASPTASQLSLM
human_HCN1      -P-SPSTQTPQ---PSAILSPCSYTTAV-C-S---PPVQSPLAARTFHYASPTASQLSLM
human_HCN2      RP-PPG---P--A-PAA-ASP-G------------PP--PP-AS---P---P--G--A--
human_HCN4      -PLQPGARSPQAAQPSP-APP-GARGGLGLPEHFLPP--PP-SSRS-PSSSP--GQLG--
                 *  *    *   *.    *

SEQ_ID_NO_2     ----------------------------------------TP-----KNEV----H-
SEQ_ID_NO_4     QQQPQ-Q-Q---VQ-Q-SQPPQTQP-QQPSPQPQ-TPGSS---TP-----KNEV----H-
SEQ_ID_NO_6     ----------------------------------------TP-----KNEV----H-
SEQ_ID_NO_8     QQQPQ-Q-Q---VQ-Q-SQPPQTQP-QQPSPQPQ-TPGSS---TP-----KNEV----H-
human_HCN1      QQQPQ-Q-Q---VQ-Q-SQPPQTQP-QQPSPQPQ-TPGSS---TP-----KNEV----H-
human_HCN2      ---P--------A----S--PRA-P-R------------T---SP--Y---GGL------
human_HCN4      --QPPGELSLGLATGPLST-PET-PPRQPEP-PSLVAGASGGASPVGFTPRGGLSPPGHS
                                                        .*        . .

SEQ_ID_NO_2     -------KSTQ--------------A-------L--HN-TN-LT--REVRPL---SASQP
SEQ_ID_NO_4     -------KSTQ--------------A-------L--HN-TN-LT--REVRPL---SASQP
SEQ_ID_NO_6     -------KSTQ--------------A-------L--HN-TN-LT--REVRPL---SASQP
SEQ_ID_NO_8     -------KSTQ--------------A-------L--HN-TN-LT--REVRPL---SASQP
human_HCN1      -------KSTQ--------------A-------L--HN-TN-LT--REVRPF---SAHQP
human_HCN2      -------PAAP-LA-G---------PA-------LPARR----LS--RASRPL---SASQP
human_HCN4      PGPPRTFPSAPPRASGSHGSLLLPPASSPPPPQVPQRRGTPPLTPGRLTQDLKLISASQP
                        ..               *        .  .     *.  *  .    ** **

SEQ_ID_NO_2     SLPHEVS-TLISR--PHPTVGESLASIPQ-P-V---T--AVPGTG-LQA--GGR--STVP
SEQ_ID_NO_4     SLPHEVS-TLISR--PHPTVGESLASIPQ-P-V---T--AVPGTG-LQA--GGR--STVP
SEQ_ID_NO_6     SLPHEVS-TLISR--PHPTVGESLASIPQ-P-V---T--AVPGTG-LQA--GGR--STVP
SEQ_ID_NO_8     SLPHEVS-TLISR--PHPTVGESLASIPQ-P-V---T--AVPGTG-LQA--GGR--STVP
human_HCN1      SLPHEVS-TLISR--PHPTVGESLASIPQ-P-V---T--AVPGTG-LQA--GGR--STVP
human_HCN2      SLPH-GA---------P-----GP--AASTR-P-A---S--S--STPRLRPTPAAR--AAAP
human_HCN4      ALPQDGAQTL-RRASPHSS-GESMAAFPLFPRAGGGSGGS-GSSGGLGP-PG-RPYGAIP
                .**.  .         *    *    *.    *       .  .   .   *    *   . *

SEQ_ID_NO_2     -QRVTL-FRQMSSGAIPP--NR-GVPPA---PPPPAAALPR-ESSSVLNTDPDAEKPRFA
SEQ_ID_NO_4     -QRVTL-FRQMSSGAIPP--NR-GVPPA---PPPPAAALPR-ESSSVLNTDPDAEKPRFA
SEQ_ID_NO_6     -QRVTL-FRQMSSGAIPP--NR-GVPPA---PPPPAAALPR-ESSSVLNTDPDAEKPRFA
SEQ_ID_NO_8     -QRVTL-FRQMSSGAIPP--NR-GVPPA---PPPPAAALPR-ESSSVLNTDPDAEKPRFA
human_HCN1      -QRVTF-FRQMSSGAIPP--NR-GVLPA---PLPLITPHPK-K-----------------
human_HCN2      ----S-PDRR-DSAS-P------GA--A---GG--LD--PQ-D-SA--R-------SRLS
human_HCN4      GQHVTLP-RKTSSGSLPPPLSLFGAR-ATSSGGPPLTAGPQREPGA--RPEP-V-RSKLP
                     .   *.  * . *      *   *           *.

SEQ_ID_NO_2     SNL
SEQ_ID_NO_4     SNL
SEQ_ID_NO_6     SNL
SEQ_ID_NO_8     SNL
human_HCN1      ---
human_HCN2      SNL
human_HCN4      SNL
```

Figure 2

```
rat_HCN1      MEGGGKPNSASNSRDDGNSVYPSKAPAT--GPAAADKRLGTPPGGG-AAGKEHGNSVCFK
mouse_HCN1    MEGGGKPNSASNSRDDGNSVFPSKAPAT--GPVAADKRLGTPPGGG-AAGKEHGNSVCFK
human_HCN1    ------------------------------------------------------------
SEQ_ID_NO_2   MEGGGKPNSSSNSRDDGNSVFPAKASAPGAGPAAAEKRLGTPPGGGGAGAKEHGNSVCFK
SEQ_ID_NO_4   MEGGGKPNSSSNSRDDGNSVFPAKASAPGAGPAAAEKRLGTPPGGGGAGAKEHGNSVCFK
SEQ_ID_NO_6   MEGGGKPNSSSNSRDDGNSVFPAKASATGAGPAAAEKRLGTPPGGGGAGAKEHGNSVCFK
SEQ_ID_NO_8   MEGGGKPNSSSNSRDDGNSVFPAKASATGAGPAAAEKRLGTPPGGGGAGAKEHGNSVCFK
                                            #

rat_HCN1      VDGGGG---------EEPAGSFEDAEGPRRQYGFMQRQFTSMLQPGVNKFSLRMFGSQKAV
mouse_HCN1    VDGGGG---------EEPAGSFEDAEGPRRQYGFMQRQFTSMLQPGVNKFSLRMFGSQKAV
human_HCN1    ------------------------------------------------------------
SEQ_ID_NO_2   VDGGGGGGGGGGGGEEPAGGFEDAEGPRRQYGFMQRQFTSMLQPGVNKFSLRMFGSQKAV
SEQ_ID_NO_4   VDGGGGGGGGGGGGEEPAGGFEDAEGPRRQYGFMQRQFTSMLQPGVNKFSLRMFGSQKAV
SEQ_ID_NO_6   VDGGGGGGGGGGGGEEPAGGFEDAEGPRRQYGFMQRQFTSMLQPGVNKFSLRMFGSQKAV
SEQ_ID_NO_8   VDGGGGGGGGGGGGEEPAGGFEDAEGPRRQYGFMQRQFTSMLQPGVNKFSLRMFGSQKAV

rat_HCN1      EKEQERVKTAGFWIIHPYSDFRFYWDLIMLIMMVGNLVIIPVGITFFTEQTTTPWIIFNV
mouse_HCN1    EKEQERVKTAGFWIIHPYSDFRFYWDLIMLIMMVGNLVIIPVGITFFTEQTTTPWIIFNV
human_HCN1    -KEQERVKTAGFWIIHPYSDFRFYWDLIMLIMMVGNLVIIPVGITFFTEQTTTPWIIFNV
SEQ_ID_NO_2   EKEQERVKTAGFWIIHPYSDFRFYWDLIMLIMMVGNLVIIPVGITFFTEQTTTPWIIFNV
SEQ_ID_NO_4   EKEQERVKTAGFWIIHPYSDFRFYWDLIMLIMMVGNLVIIPVGITFFTEQTTTPWIIFNV
SEQ_ID_NO_6   EKEQERVKTAGFWIIHPYSDFRFYWDLIMLIMMVGNLVIIPVGITFFTEQTTTPWIIFNV
SEQ_ID_NO_8   EKEQERVKTAGFWIIHPYSDFRFYWDLIMLIMMVGNLVIIPVGITFFTEQTTTPWIIFNV
              ************************************************** *******
                                                              S1
rat_HCN1      ASDTVFLLDLIMNFRTGTVNEDSSEIILDPKVIKMNYLKSWFVVDFISSIPVDYIFLIVE
mouse_HCN1    ASDTVFLLDLIMNFRTGTVNEDSSEIILDPKVIKMNYLKSWFVVDFISSIPVDYIFLIVE
human_HCN1    ASDTVFLLDLIMNFRTGTVNEDSSEIILDPKVIKMNYLKSWFVVDFISSIPVDYIFLIVE
SEQ_ID_NO_2   ASDTVFLLDLIMNFRTGTVNEDSSEIILDPKVIKMNYLKSWFVVDFISSIPVDYIFLIVE
SEQ_ID_NO_4   ASDTVFLLDLIMNFRTGTVNEDSSEIILDPKVIKMNYLKSWFVVDFISSIPVDYIFLIVE
SEQ_ID_NO_6   ASDTVFLLDLIMNFRTGTVNEDSSEIILDPKVIKMNYLKSWFVVDFISSIPVDYIFLIVE
SEQ_ID_NO_8   ASDTVFLLDLIMNFRTGTVNEDSSEIILDPKVIKMNYLKSWFVVDFISSIPVDYIFLIVE
              ************************************************************
                            S2                              S3
rat_HCN1      KGMDSEVYKTARALRIVRFTKILSLLRLLRLSRLIRYIHQWEEIFHMTYDLASAVVRIFN
mouse_HCN1    KGMDSEVYKTARALRIVRFTKILSLLRLLRLSRLIRYIHQWEEIFHMTYDLASAVVRIFN
human_HCN1    KGMDSEVYKTARALRIVRFTKILSLLRLLRLSRLIRYIHQWEEIFHMTYDLASAVVRIFN
SEQ_ID_NO_2   KGMDSEVYKTARALRIVRFTKILSLLRLLRLSRLIRYIHQWEEIFHMTYDLASAVVRIFN
SEQ_ID_NO_4   KGMDSEVYKTARALRIVRFTKILSLLRLLRLSRLIRYIHQWEEIFHMTYDLASAVVRIFN
SEQ_ID_NO_6   KGMDSEVYKTARALRIVRFTKILSLLRLLRLSRLIRYIHQWEEIFHMTYDLASAVVRIFN
SEQ_ID_NO_8   KGMDSEVYKTARALRIVRFTKILSLLRLLRLSRLIRYIHQWEEIFHMTYDLASAVVRIFN
              ************************************************************
                                        S4
rat_HCN1      LIGMMLLLCHWDGCLQFLVPLLQDFPPDCWVSLNEMVNDSWGKQYSYALFKAMSHMLCIG
mouse_HCN1    LIGMMLLLCHWDGCLQFLVPLLQDFPPDCWVSLNEMVNDSWGKQYSYALFKAMSHMLCIG
human_HCN1    LIGMMLLLCHWDGCLQFLVPLLQDFPPDCWVSLNEMVNDSWGKQYSYALFKAMSHMLCIG
SEQ_ID_NO_2   LIGMMLLLCHWDGCLQFLVPLLQDFPPDCWVSLNEMVNDSWGKQYSYALFKAMSHMLCIG
SEQ_ID_NO_4   LIGMMLLLCHWDGCLQFLVPLLQDFPPDCWVSLNEMVNDSWGKQYSYALFKAMSHMLCIG
SEQ_ID_NO_6   LIGMMLLLCHWDGCLQFLVPLLQDFPPDCWVSLNEMVNDSWGKQYSYALFKAMSHMLCIG
SEQ_ID_NO_8   LIGMMLLLCHWDGCLQFLVPLLQDFPPDCWVSLNEMVNDSWGKQYSYALFKAMSHMLCIG
              ************************************************************
                                S5                          Pore
rat_HCN1      YGAQAPVSMSDLWITMLSMIVGATCYAMFVGHATALIQSLDSSRRQYQEKYKQVEQYMSF
mouse_HCN1    YGAQAPVSMSDLWITMLSMIVGATCYAMFVGHATALIQSLDSSRRQYQEKYKQVEQYMSF
human_HCN1    YGAQAPVSMSDLWITMLSMIVGATCYAMFVGHATALIQSLDSSRRQYQEKYKQVEQYMSF
SEQ_ID_NO_2   YGAQAPVSMSDLWITMLSMIVGATCYAMFVGHATALIQSLDSSRRQYQEKYKQVEQYMSF
SEQ_ID_NO_4   YGAQAPVSMSDLWITMLSMIVGATCYAMFVGHATALIQSLDSSRRQYQEKYKQVEQYMSF
SEQ_ID_NO_6   YGAQAPVSMSDLWITMLSMIVGATCYAMFVGHATALIQSLDSSRRQYQEKYKQVEQYMSF
SEQ_ID_NO_8   YGAQAPVSMSDLWITMLSMIVGATCYAMFVGHATALIQSLDSSRRQYQEKYKQVEQYMSF
              ************************************************************
                                        S6
rat_HCN1      HKLPADMRQKIHDYYEHRYQGKIFDEENILSELNDPLREEIVNFNCRKLVATMPLFANAD
mouse_HCN1    HKLPADMRQKIHDYYEHRYQGKIFDEENILSELNDPLREEIVNFNCRKLVATMPLFANAD
human_HCN1    HKLPADMRQKIHDYYEHRYQGKIFDEENILNELNDPLREEIVNFNCRKLVATMPLFANAD
SEQ_ID_NO_2   HKLPADMRQKIHDYYEHRYQGKIFDEENILNELNDPLREEIVNFNCRKLVATMPLFANAD
SEQ_ID_NO_4   HKLPADMRQKIHDYYEHRYQGKIFDEENILNELNDPLREEIVNFNCRKLVATMPLFANAD
SEQ_ID_NO_6   HKLPADMRQKIHDYYEHRYQGKIFDEENILNELNDPLREEIVNFNCRKLVATMPLFANAD
SEQ_ID_NO_8   HKLPADMRQKIHDYYEHRYQGKIFDEENILNELNDPLREEIVNFNCRKLVATMPLFANAD
              ******************************  ****************************
```

Figure 2 continued

```
rat_HCN1        PNFVTAMLSKLRFEVFQPGDYIIREGAVGKKMYFIQHGVAGVITKSSKEMKLTDGSYFGE
mouse_HCN1      PNFVTAMLSKLRFEVFQPGDYIIREGAVGKKMYFIQHGVAGVITKSSKEMKLTDGSYFGE
human_HCN1      PNFVTAMLSKLRFEVFQPGDYIIREGAVGKKMYFIQHGVAGVITKSSKEMKLTDGSYFGE
SEQ_ID_NO_2     PNFVTAMLSKLRFEVFQPGDYIIREGAVGKKMYFIQHGVAGVITKSSKEMKLTDGSYFGE
SEQ_ID_NO_4     PNFVTAMLSKLRFEVFQPGDYIIREGAVGKKMYFIQHGVAGVITKSSKEMKLTDGSYFGE
SEQ_ID_NO_6     PNFVTAMLSKLRFEVFQPGDYIIREGAVGKKMYFIQHGVAGVITKSSKEMKLTDGSYFGE
SEQ_ID_NO_8     PNFVTAMLSKLRFEVFQPGDYIIREGAVGKKMYFIQHGVAGVITKSSKEMKLTDGSYFGE
                ************************************************************
                                           CNBD
rat_HCN1        ICLLTKGRRTASVRADTYCRLYSLSVDNFNEVLEEYPMMRRAFETVAIDRLDRIGKKNSI
mouse_HCN1      ICLLTKGRRTASVRADTYCRLYSLSVDNFNEVLEEYPMMRRAFETVAIDRLDRIGKKNSI
human_HCN1      ICLLTKGRRTASVRADTYCRLYSLSVDNFNEVLEEYPMMRRAFETVAIDRLDRIGKKNSI
SEQ_ID_NO_2     ICLLTKGRRTASVRADTYCRLYSLSVDNFNEVLEEYPMMRRAFETVAIDRLDRIGKKNSI
SEQ_ID_NO_4     ICLLTKGRRTASVRADTYCRLYSLSVDNFNEVLEEYPMMRRAFETVAIDRLDRIGKKNSI
SEQ_ID_NO_6     ICLLTKGRRTASVRADTYCRLYSLSVDNFNEVLEEYPMMRRAFETVAIDRLDRIGKKNSI
SEQ_ID_NO_8     ICLLTKGRRTASVRADTYCRLYSLSVDNFNEVLEEYPMMRRAFETVAIDRLDRIGKKNSI
                ************************************************************

rat_HCN1        LLQKFQKDLNTGVFNNQENEILKQIVKHDREMVQAIPPINYPQMTALNCTSSTTTPTSRM
mouse_HCN1      LLQKFQKDLNTGVFNNQENEILKQIVKHDREMVQAIPPINYPQMTALNCTSSTTTPTSRM
human_HCN1      LLQKFQKDLNTGVFNNQENEILKQIVKHDREMVQAIAPINYPQMTTLNSTSSTTTPTSRM
SEQ_ID_NO_2     LLQKFQKDLNTGVFNNQENEILKQIVKHDREMVQAIAPINYPQMTTLNSTSSTTTPTSRM
SEQ_ID_NO_4     LLQKFQKDLNTGVFNNQENEILKQIVKHDREMVQAIAPINYPQMTTLNSTSSTTTPTSRM
SEQ_ID_NO_6     LLQKFQKDLNTGVFNNQENEILKQIVKHDREMVQAIAPINYPQMTTLNSTSSTTTPTSRM
SEQ_ID_NO_8     LLQKFQKDLNTGVFNNQENEILKQIVKHDREMVQAIAPINYPQMTTLNSTSSTTTPTSRM
                ************************************ ********.**.***********

rat_HCN1        RTQSPPVYTATSLSHSNLHSPSPSTQTPQPSAILSPCSYTTAVCSPPIQSPLATRTFHYA
mouse_HCN1      RTQSPPVYTATSLSHSNLHSPSPSTQTPQPSAILSPCSYTTAVCSPPIQSPLATRTFHYA
human_HCN1      RTQSPPVYTATSLSHSNLHSPSPSTQTPQPSAILSPCSYTTAVCSPPVQSPLAARTFHYA
SEQ_ID_NO_2     RTQSPPVYTATSLSHSNLHSPSPSTQTPQPSAILSPCS----------------------
SEQ_ID_NO_4     RTQSPPVYTATSLSHSNLHSPSPSTQTPQPSAILSPCSYTTAVCSPPVQSPLAARTFHYA
SEQ_ID_NO_6     RTQSPPVYTATSLSHSNLHFPSPSTQTPQPSAILSPCS----------------------
SEQ_ID_NO_8     RTQSPPVYTATSLSHSNLHFPSPSTQTPQPSAILSPCSYTTAVCSPPVQSPLAARTFHYA
                ******************* ******************
                                   #
rat_HCN1        SPTASQLSLMQQPQPQLQQSQVQQTQTQTQQQQQQQQPQPQPQQPQQQQQQQQQQQQQQQ
mouse_HCN1      SPTASQLSLMQQPQQQLPQSQVQQTQTQTQQQQQQQQQQQQQQQQQQQQQQQQQQQQQQQ
human_HCN1      SPTASQLSLMQQ--------------------------------QPQQQVQQSQPPQTQP
SEQ_ID_NO_2     ------------------------------------------------------------
SEQ_ID_NO_4     SPTASQLSLMQQ--------------------------------QPQQQVQQSQPPQTQP
SEQ_ID_NO_6     ------------------------------------------------------------
SEQ_ID_NO_8     SPTASQLSLMQQ--------------------------------QPQQQVQQSQPPQTQP

rat_HCN1        QQQQQQPQTPGSSTPKNEVHKSTQALHNTHLTREVRPLSASQPSLPHEVSTMISRPHPTV
mouse_HCN1      QQQQQQPQTPGSSTPKNEVHKSTQALHNTNLTKEVRPLSASQPSLPHEVSTLISRPHPTV
human_HCN1      QQPSPQPQTPGSSTPKNEVHKSTQALHNTNLTREVRPFSAWQPSLPHEVSTLISRPHPTV
SEQ_ID_NO_2     -------------TPKNEVHKSTQALHNTNLTREVRPLSASQPSLPHEVSTLISRPHPTV
SEQ_ID_NO_4     QQPSPQPQTPGSSTPKNEVHKSTQALHNTNLTREVRPLSASQPSLPHEVSTLISRPHPTV
SEQ_ID_NO_6     -------------TPKNEVHKSTQALHNTNLTREVRPLSASQPSLPHEVSTLISRPHPTV
SEQ_ID_NO_8     QQPSPQPQTPGSSTPKNEVHKSTQALHNTNLTREVRPLSASQPSLPHEVSTLISRPHPTV
                             ****************.**.**** ** **********.********

rat_HCN1        GESLASIPQPVATVHSTGLQAGSRSTVPQRVTLFRQMSSGAIPPNRGVPPAPPPPAAVQ-
mouse_HCN1      GESLASIPQPVAAVHSTGLQAGSRSTVPQRVTLFRQMSSGAIPPNRGVPPAPPPPAAVQ-
human_HCN1      GESLASIPQPVTAVPGTGLQAGGRSTVPQRVTFFRQMSSGAIPPNRGVLPAPLPLITPHP
SEQ_ID_NO_2     GESLASIPQPVTAVPGTGLQAGGRSTVPQRVTLFRQMSSGAIPPNRGVPPAPPPPAAALP
SEQ_ID_NO_4     GESLASIPQPVTAVPGTGLQAGGRSTVPQRVTLFRQMSSGAIPPNRGVPPAPPPPAAALP
SEQ_ID_NO_6     GESLASIPQPVTAVPGTGLQAGGRSTVPQRVTLFRQMSSGAIPPNRGVPPAPPPPAAALP
SEQ_ID_NO_8     GESLASIPQPVTAVPGTGLQAGGRSTVPQRVTLFRQMSSGAIPPNRGVPPAPPPPAAALP
                ***********..*  ****** ********* *************** *** *

rat_HCN1        RESPSVLNKDPDAEKPRFASNL
mouse_HCN1      RESPSVLNTDPDAEKPRFASNL
human_HCN1      KK--------------------
SEQ_ID_NO_2     RESSSVLNTDPDAEKPRFASNL
SEQ_ID_NO_4     RESSSVLNTDPDAEKPRFASNL
SEQ_ID_NO_6     RESSSVLNTDPDAEKPRFASNL
SEQ_ID_NO_8     RESSSVLNTDPDAEKPRFASNL
```

Figure 3
5 A.
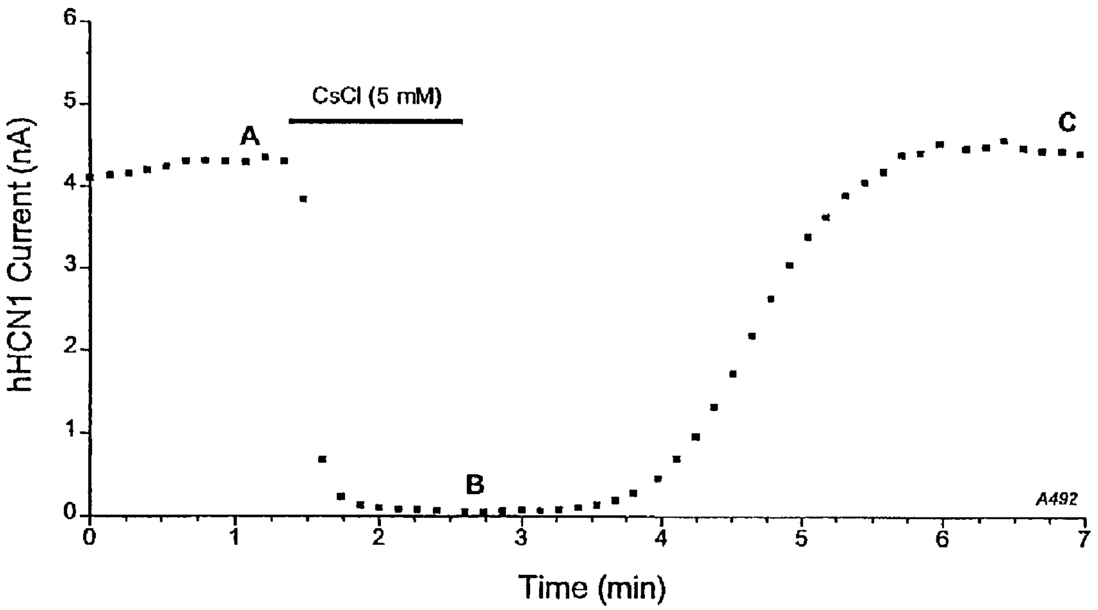
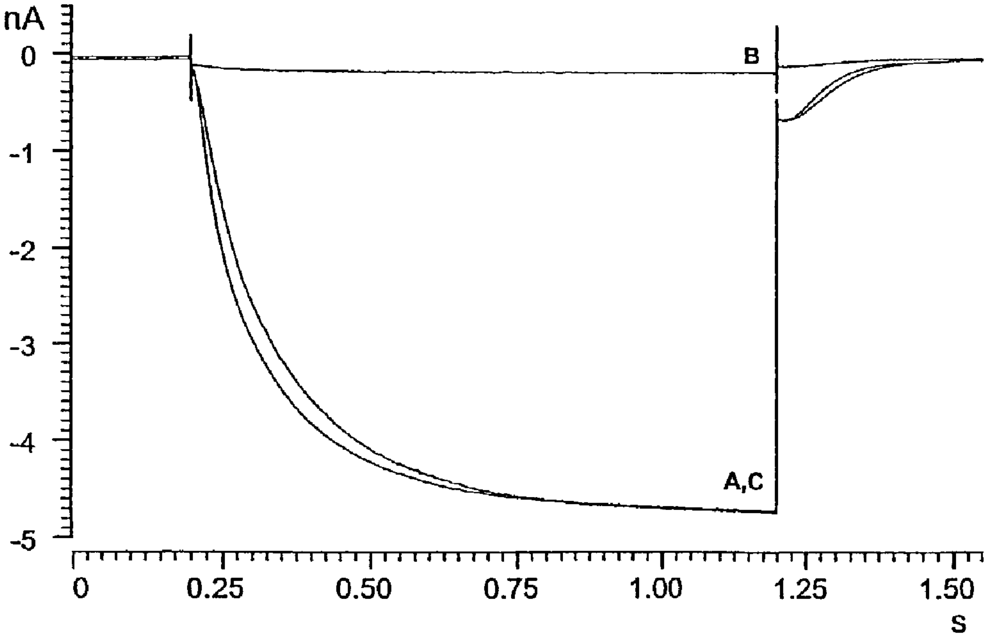
B.

Figure 4
A.
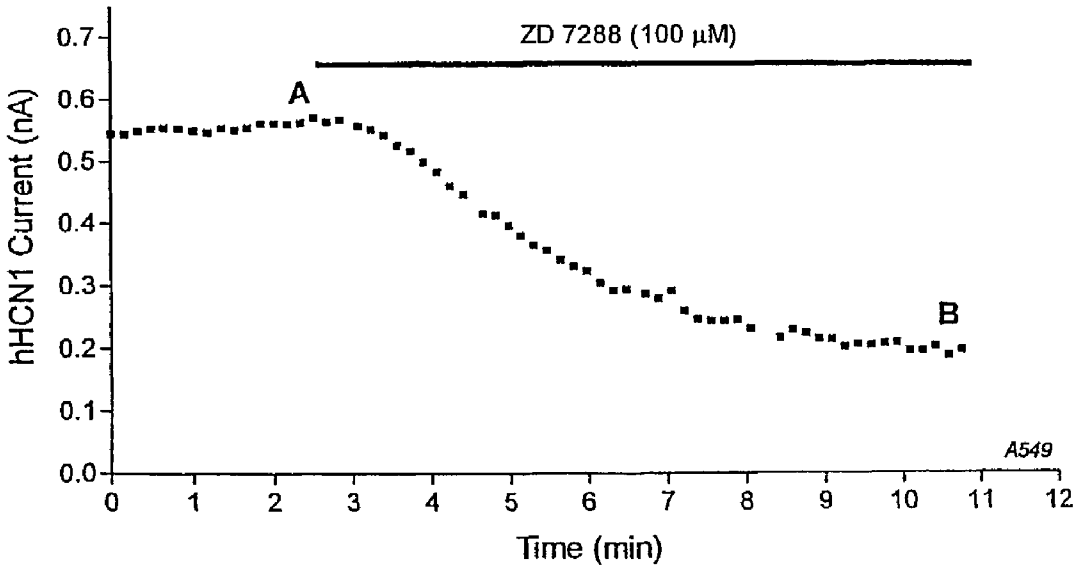
B.
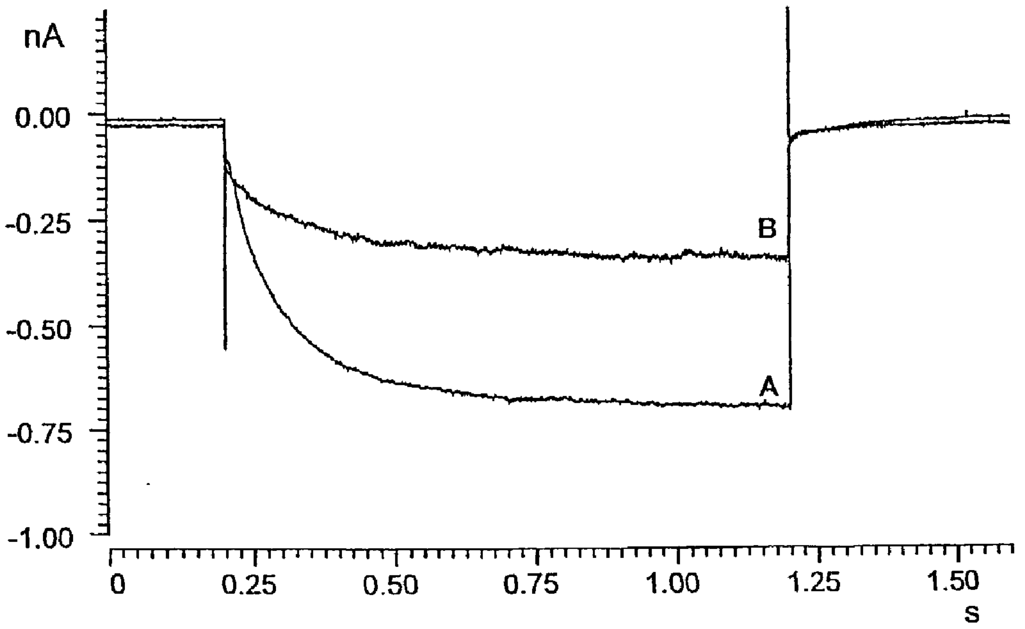

Figure 5
5 A.
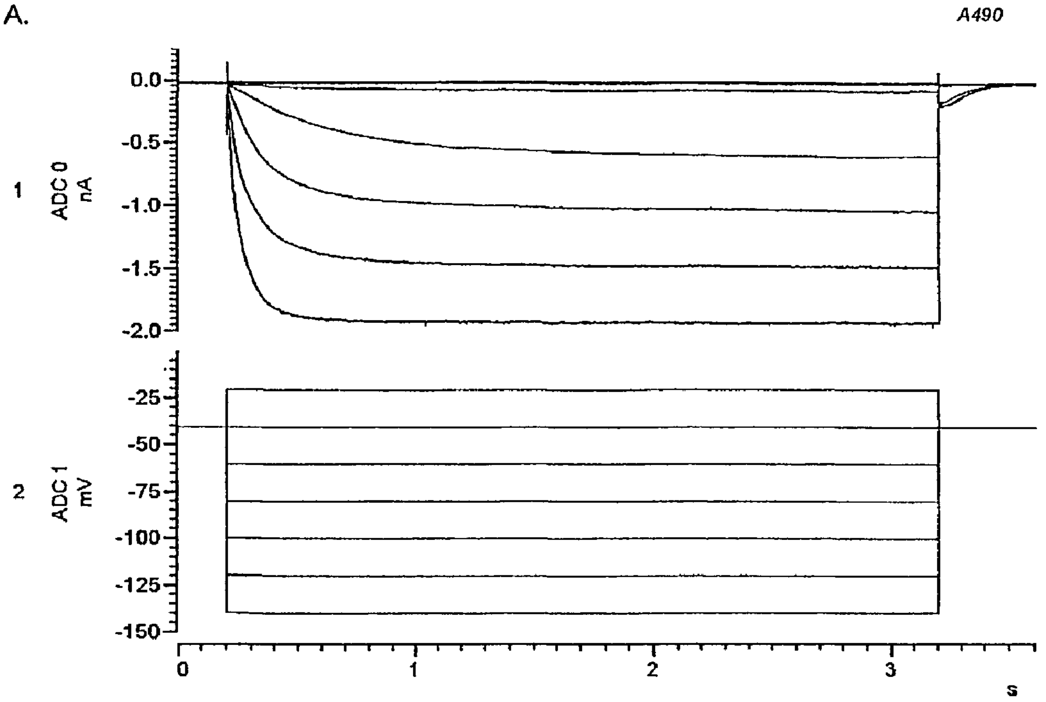
B.
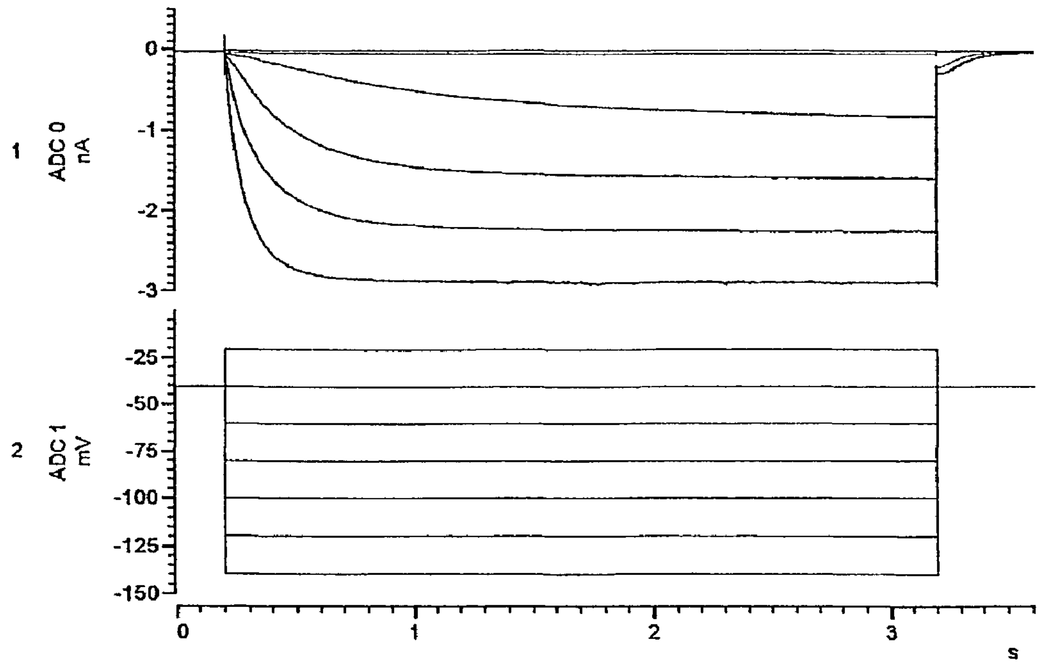

FULL LENGTH HUMAN HCN1$I_H$ CHANNEL SUBUNIT AND VARIANTS

FIELD OF THE INVENTION

This invention relates to a DNA sequence encoding a member of the hyperpolarised activated ion channel family (HCN) and variants thereof, and the use of said sequences in assays for the measurement of gene expression. It also relates to assays for screening of $I_h$ activators and blockers for clinical and therapeutic use in the management of human psychiatric and neurological dysfunction in the CNS, cardiovascular dysfunction of the heart, and reproductive dysfunction and/or contraception related to $I_h$ function in testes and spermatozoa. Further, antibodies against the expressed DNA sequences and other compounds reactive with the expressed DNA sequence are also part of the invention

BACKGROUND OF THE INVENTION

Voltage-gated ion channels play a critical role in shaping of electrical activity of neuronal and muscle cells, and in controlling the secretion of neurotransmitters and hormones through the gating of calcium ion entry. Large families of voltage gated sodium ($Na^+$), potassium ($K^+$) and calcium ($Ca^{2+}$) ion channels have been defined using electrophysiological, pharmacological and molecular techniques [1, 18]; they are named according to their selective permeability for a particular cation with reference to their voltage dependence, kinetic behaviour or molecular identity. The importance of membrane voltage and ion permeability in the control of cell function ensures that modulation of ion channels will invariably have important consequences for cells and tissues, and such modulation can often be turned to therapeutic advantage. Major indication for ion channel modulators already include cardiac arrhythmia, hypertension, anxiety, epilepsy, pain, chemotherapy-induced nausea and diabetes as well as a range of drugs in development for important new indications such as neuroprotection and psychiatry.

A variety of bodily functions such as heart beat, sleep-wake cycles, secretion of hormones and control of behavioural state depend on the action of pacemakers, specialised cells that are able to generate rhythmic, spontaneously firing action potentials. The archetypal organ displaying autonomic rhythmicity is the heart.

Pacemaking in the heart is accomplished by the rhythmic discharge of the sino atrial node [8, 11, 12]. The firing rate of the sino atrial node is determined by the diastolic depolarisation phase of the action potential. During this phase the membrane potential is slowly depolarised to the threshold triggering the next action potential. The ionic conductance underlying the cardiac pacemaker depolarisation was identified in the late seventies and early eighties [10] and called $I_f$ (f for 'funny') or $I_h$ (h for hyperpolarisation activated). A similar current was subsequently discovered in neurones, first in photoreceptors, [2, 3, 6] and then in various central neurons eg hippocampal pyramidal cells [16] where is was called $I_q$ (q for 'queer'). This current was subsequently found in a wide variety of central and peripheral neurons [25].

$I_h$ channels have several distinctive features. Unlike most voltage-gated channels, they open in response to negative-going voltage steps to potentials within the range of the normal resting potential. They conduct both $K^+$ and $Na^+$ ions with a three fold greater permeability to $K^+$, yielding a reversal potential of −30 to −40 mV under physiological conditions. As a result, the opening of these channels near the resting potential (~−60 mV) generates an inward, depolarising current that is largely carried by $Na^+$ [25]. Another unusual property of these channels is their regulation by cyclic nucleotides [11], which speed up the rate of channel activation by binding to an intracellular site on the channel. In the heart, this in an important mechanism responsible for the acceleration of heart rate in response to sympathetic stimulation. Activation of β-adrenergic receptors leads to an activation of adenylyl cyclase with the resulting increase in intracellular cAMP directly activating the $I_h$ channel. cAMP binding leads to a shift in the activation curve towards more positive voltages. This shift results in an increased inward current at a fixed membrane potential and therefore an acceleration of the diastolic depolarisation [9]. Muscarinic stimulation slows the heart rate, in part due to a decrease in cAMP level and a resulting reduction in the $I_h$ current [13, 33].

In neurons, $I_h$ channels have diverse functions. They were initially shown to be inward rectifiers; they are active near the resting potential and pass inward current more readily than outward current, thereby helping to control of resting potential and input resistance [25]. In photoreceptors, $I_h$ channels help to damp the hyperpolarising effect of light; they are activated by hyperpolarisation, causing the voltage response to light to fade during the first 100-200 ms, thus producing sensory adaptation. In many CNS neurons, activation of $I_h$ channels following post inhibitory post synaptic potentials contributes to a rebound afterdepolarisation (ADP), which can trigger an action potential. $I_h$ is also generates or contributes to 'pacemaker' potentials that controls the rate of rhythmic oscillations, similar to its role in the heart. $I_h$ has been found to regulate the rhythmic activity of thalamic relay neurons [23] and inferior olivary neurons [5] through interaction with a T-type calcium current. The oscillating single neurons are part of neuronal networks and are involved in the generation and modulation of rhythmic activity of these networks. A well studied example are spindle waves observed in the EEG during slow wave sleep, which are generated through interactions between thalamic reticular and relay neurons [4]. Regulation of $I_h$ in these cells is important in the sleep-wake cycle. Although less well investigated, results suggest a similar role for $I_h$ in the generation of oscillations in hippocampal neurons [21, 32] and respiratory neurons of the preBotzinger complex of the ventrolateral medulla [26]. $I_h$ channels are also expressed in dendrites where they influence the cable properties of the dendrite and shape the time course of the EPSP as it is propagated to the soma [22]. A recent study has extended the role of $I_h$ neurons by showing that these channels can alter neurotransmitter release from presynaptic terminals as Crayfish neuromuscular synapses. Presynaptic cAMP generation by via serotonin receptor activation directly modulates $I_h$ in axons that produces an increase in synaptic strength which cannot be explained solely by depolarisation of the presynaptic membrane [7].

The genes encoding $I_h$ channels were recently cloned from both mammals [19, 28, 29] and sea urchins [15]. These genes, called HCN1-4 in mammals, are members of the voltage gated $K^+$ channel family. The encoded proteins contain six transmembrane segments, including a positively charged S4 voltage sensor and a pore-forming P region that includes the $K^+$ channel signature sequence GYG. In addition, the C-terminus contains a 120-amino acid sequence that is homologous to the cAMP and cGMP binding domains of other proteins, and is therefore the likely site for cAMP regulation of channel opening [9,20]. All four mammalian genes are expressed in brain, with differing expression patterns [24]. While the first reported cloning of $I_h$ was from sea urchin spermatozoa [15], the functional significance is poorly understood at present. The channel is expressed in sperm flagellum and it was postulated that it may be involved in the control of flagella beating. One of the cloned isoforms, HCN4, has been detected in testes suggesting that $I_h$ may also have a function in mammalian testicular and sperm function [30].

These ion channels are the target for blocking molecules for therapeutic use in dysfunction in the CNS, cardiovascular dysfunction of the heart, and reproductive dysfunction and/or contraception related to $I_h$ function in testes and spermatozoa. For instance, compounds have already been developed with the therapeutically interesting property of inducing bradycardia with minimal inotropic side effects [14, 17]. Unfortunately, there are no compounds yet described that distinguish cardiac from neuronal isoforms, and volunteers experienced optical hallucinations probably due to reduced functionality of $I_h$ in photoreceptors. It is clear the ability to develop agents that are selective for the CNS vs heart or vice versa requires the availability of the cloned subunits to screen for compounds selective for subunits expressed in either neuronal or cardiac tissue.

BRIEF SUMMARY OF THE INVENTION

It is the object of the present invention to provide full-length functional human HCN1 channel subunits. Furthermore, variants of the full-length functional human HCN1 subunit are also provided. Human HCN1 channel subunits are preferred over subunits from other species since they are preferably used to select compounds that can be used to treat CNS disorders, cardiovascular dysfunction of the heart, and reproductive dysfunction and/or contraception related to $I_h$ function in testes and spermatozoa in humans.

DETAILED DESCRIPTION OF THE INVENTION

One aspect of the invention concerns the full length cDNA sequence of the human HCN1 channel subunit (SEQ ID NO: 1). The expression of this subunit is predominantly restricted to the CNS and has only been detected in some peripheral tissues to a very limited extend. This subunit is therefore a candidate for screening compounds with a selective effect in the CNS with a reduced propensity for undesirable side effects such as bradycardia via activity at $I_h$ in the heart. In contrast with the prior art, the present invention provides the full-length sequence of human HCN1 and sequence variants whereas previous publications have only identified partial human HCN1 sequences. The major advantage of having a full-length sequence is that this allows functional expression in in vitro systems (ie in transfected cell lines) for the identification of compounds increasing (opening the channel) or decreasing (blocking the channel) ion flux through the expressed channel. While expression of partial sequences may be possible, these will not give rise to channels with the full functional characteristics of the full-length channel since they lack polypeptide domains that contribute to the functional characteristics of the channel. In addition, partial sequences may lack polypeptide domains with important target sites for compounds that modulate channel activity. Functional expression of partial sequences, particularly those lacking the 5' end such as those reported for human HCN1 [1] is additionally problematic since they lack the sequence encoding the N-terminal signal peptide required for directing the nascent polypeptide to the endoplasmic reticulum where all nascent plasma membrane bound proteins are synthesised. The inherent advantage of an assay based on channel function, rather than, say a binding assay, is that a functional assay allows for the screening of compounds that interact with the channel as either blockers or openers. Binding assays give no such information, nor do they allow the identification of allosteric or use-dependent modulators of the channel.

By the term "full-length" as used herein we mean a DNA sequence that contains a complete open reading frame, beginning with a start codon at its 5' end, preferably with a Kozak consensus, downstream to an in-frame stop codon.

The full-length DNA sequence for HCN1 (SEQ ID NO: 1) was obtained using a combined molecular biology and bioinformatics approach. Initial screening of a proprietary database with the published human HCN1 sequence [1] identified a single clone according to SEQ ID NO: 9 that matched at the 3' end. Further analysis of the predicted amino acid sequence of this clone (SEQ ID NO: 10) confirmed that it encoded the 3' end of human HCN1 with an in-frame stop codon. Comparison with the full-length murine HCN1 sequence indicated that the published human sequence lacks approximately 330 bases of 5' sequence upstream to the translational initiation codon. Several approaches were adopted to attempt to obtain the missing 5' end. These included cDNA library screening, genomic library screening and 5' RACE-PCR. RACE-PCR consistently generated a further 153 bp (SEQ ID NO: 13) upstream of the published human HCN1 sequence. A search of genomic databases with this new 5' end sequence identified a BAC clone (RP11-398G9) in the updated EMBL high throughput genomic (HTG) database (em62htgnew). Sequence analysis of this clone suggests that it contains an in-frame initiation codon and an open reading frame homologous to murine HCN1. The 5' end of human HCN1 is extremely GC-rich (approximately 80%) thus explaining why conventional means of cloning this sequence proved fruitless.

Thus, sequence from a combination of newly identified genomic BAC clone, RACE-PCR, published sequence and the clone obtained from the proprietary database have been assembled to generate a full length cDNA encoding a full length human HCN1 Ih channel subunit (SEQ ID NO: 1).

In another aspect of the invention, the sequences of the present invention can be used to derive primers and probes for use in DNA amplification reactions in order to perform diagnostic procedures or to identify further, neighbouring genes which also may contribute to the expression of HCN1. Also, fragments may be generated with PCR procedures, as the sequences that are shown in SEQ ID NO: 13, SEQ ID NO: 14, SEQ ID NO: 15, SEQ ID NO: 18, SEQ ID NO: 19 and SEQ ID NO: 21. In this way mutation analysis may be performed.

It is known in the art that genes may vary within and among species with respect to their nucleotide sequence. The sequence of full length HCN1 cDNAs from other individuals as well as their gene sequence may now be readily identified using the above probes and primers.

Availability of the full-length sequence now allows to provide for assays that measure whether the functional characteristics of the full-length channel are altered. It is clear for the skilled person that now all kinds of functional equivalents may be genetically engineered. Therefore, the invention also comprises functional equivalents, which are characterised in that they are capable of hybridising to at least part of the HCN1 sequence shown in SEQ ID NO: 1, preferably under high stringency conditions.

The present invention also includes these functional variants. Examples of such variants are for example deletions, insertions, point substitutions (single nucleotide polymorphisms) and splice variants. Also included in this term are other sequence variants, for example splice variants of a sequence which may differ in size through inclusion or exclusion of different exons. Identification of sequence variants and single nucleotide polymorphisms in particular are important for two reasons: first by identifying the small differences that influence the type and severity of diseases contracted by individuals; and second, by being able to understand the reasons behind variation of response to medicines at the individual level. Understanding how these variations in the genetic code influence biological systems will be the key to discovering new medicines and enabling doctors to prescribe medicines to patients who are likely to respond.

The present invention provides such functional variants. SEQ ID NO: 3 which is a full-length variant that contains a 189 bp insertion at position 2114 in SEQ ID NO 1, indicative of a splicing variant compared to SEQ ID NO: 1. This insertion encodes a further 63 amino acids in SEQ ID NO 4 in a region predicted to encode a portion of the carboxy-terminal domain of the polypeptide (FIGS. 1 and 2). Two single nucleotide variants are also provided in SEQ ID NO 5. The first is a C (SEQ ID NO 1) to A (SEQ ID NO 5) transition at position 107 resulting in a change of amino acid from Pro (SEQ ID NO 2) to Thr (SEQ ID NO 6) at position 28. This occurs in a region predicted to encode the amino terminal domain of the polypeptide (FIGS. 1 and 2). The second single nucleotide variant is a C (SEQ ID NO 1) to T (SEQ ID NO 5) transition at position 2064 resulting in a change of amino acid from Ser (SEQ ID NO 2) to Phe (SEQ ID NO 6). This occurs in a region predicted to encode the carboxy-terminal domain of the polypeptide immediately upstream of the splice variant insertion site. Both single nucleotide variants may therefore occur in association with the splicing variant giving rise to SEQ ID NO 7 encoding the polypeptide SEQ ID NO 8. In addition, a functional variant may comprise only one of these single nucleotide differences in conjunction with the splicing isoforms.

In addition, the sequences of the present invention contain a number of other differences compared to the published sequence [1]. These include a further eleven point substitutions, corresponding to 5 amino acid changes, and divergent sequence at the 3' end of the published sequence [1].

Two nucleic acid fragments are considered to have hybridisable sequences if they are capable to hybridising to one another under typical hybridisation and wash conditions, as described, for example in Maniatis, et al., pages 320-328, and 382-389, or using reduced stringency wash conditions that allow at most about 25-30% basepair mismatches, for example: 2×SSC, 0.1% SDS, room temperature twice, 30 minutes each, then 2×SSC, 0.1% SDS 37° C. once, 30 minutes; then 2×SSC, room temperature twice ten minutes each. Preferably, homologous nucleic acid strands contain 15-25% basepair mismatches, even more preferably 5-15% basepair mismatches. These degrees of homology can be selected by using wash conditions of appropriate stringency for identification of clones from gene libraries or other sources of genetic material, as is well known in the art.

Furthermore, to accommodate codon variability, the invention also includes sequences coding for the same amino acid sequences as the sequences disclosed herein. Also portions of the coding sequences coding for individual domains of the expressed protein are part of the invention as well as allelic and species variations thereof. Sometimes, a gene expresses different isoforms in a certain tissue which includes splicing variants, that may result in an altered 5' or 3' mRNA or in the inclusion of an additional exon sequence. Alternatively, the messenger might have an exon less as compared to its counterpart. These sequences as well as the proteins encoded by these sequences all are expected to perform the same or similar functions and form also part of the invention.

The sequence information as provided herein should not be so narrowly construed as to require inclusion of erroneously identified bases. The specific sequence disclosed herein can be used to isolate further genes which in turn can be subjected to further sequence analyses thereby identifying sequencing errors.

Thus, in one aspect, the present invention provides for a DNA sequence encoding a full length human hyperpolarised activated ion channel of the HCN 1 subtype or functional equivalents thereof.

The DNA according to the invention may be obtained from cDNA. Alternatively, the coding sequence might be obtained from genomic DNA, or prepared using DNA synthesis techniques. The polynucleotide may also be in the form of RNA. The polynucleotide may be in single stranded or double stranded form. The single strand might be the coding strand or the non-coding (anti-sense) strand.

The present invention further relates to polynucleotides which have at least 80%, preferably 90% and more preferably 95% and even more preferably at least 98% identity with SEQ ID NO:1, provided that such polynucleotides encode polypeptides which retain essentially the same biological function or activity as the natural, mature protein. Even more preferred is the full length sequence according to SEQ ID NO: 1, SEQ ID NO: 3, SEQ ID NO 5 or SEQ ID NO 7

The percentage of identity between two sequences can be determined with programs such as DNAMAN (Lynnon Biosoft, version 3.2). Using this program two sequences can be aligned using the optimal alignment algorithm of Smith and Waterman (1981, J. Mol. Biol, 147:195-197). After alignment of the two sequences the percentage identity can be calculated by dividing the number of identical nucleotides between the two sequences by the length of the aligned sequences minus the length of all gaps.

The DNA according to the invention will be very useful for in vivo or in vitro expression of the novel sequence according to the invention in sufficient quantities and in substantially pure form.

In another aspect of the invention, a full length human hyperpolarised activated ion channel of the HCN 1 subtype or functional equivalents thereof are provided. An example of such a polypeptide is a polypeptide sequence according to SEQ ID NO: 2. SEQ ID NO: 2 is encoded by the open reading frame of SEQ ID NO: 1 and consists of 827 amino acids.

Preferably, the polypeptides according to the invention comprise the amino acid sequence as shown in SEQ ID NO: 2.

Also functional equivalents, that is polypeptides homologous to SEQ ID NO: 2 or parts thereof having variations of the sequence while still maintaining functional characteristics, are included in the invention. Such variants are provided in SEQ ID NO: 4 which is a polypeptide encoded by the open reading frame of SEQ ID NO: 3, SEQ ID NO: 6 which is a polypeptide encoded by the open reading frame of SEQ ID NO: 5 and SEQ ID NO: 8 which is a polypeptide encoded by the open reading frame of SEQ ID NO: 7

The variations that can occur in a sequence may be demonstrated by (an) amino acid difference(s) in the overall sequence or by deletions, substitutions, insertions, inversions or additions of (an) amino acid(s) in said sequence. Amino acid substitutions that are expected not to essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science, 1985, 227, 1435-1441) and determining the functional similarity between homologous polypeptides. It will be clear that also polynucleotides coding for such variants are part of the invention.

The polypeptides according to the present invention include the polypeptides comprising SEQ ID NO: 2 but also its isoforms, i.e. polypeptides with a similarity of 70%, preferably 85%, more preferably 90% even more preferably 95% or even 98%, provided these isoforms retain the same biological functions as the sequence shown in SEQ ID NO: 2, like the sequences shown in SEQ ID NO: 4, SEQ ID NO: 6 and SEQ ID NO: 8. Also fragments of such polypeptides still capable of conferring these biological effects are included. Especially portions which still bind to ligands form part of the invention. Such portions may be functional per se, e.g. in solubilized form or they might be linked to other polypeptides, either by known biotechnological ways or by chemical synthesis, to obtain chimeric proteins. Such proteins might be useful as therapeutic agent in that they may substitute the gene product in individuals with aberrant expression of the HCN1 gene. Polypeptides obtainable from alternative splice products are also included in this invention.

As an example of a functional equivalent SEQ ID NO: 4 is provided. This polypeptide corresponds to the open reading frame of SEQ ID NO: 3 and contains an insertion of 63 amino acids.

Further examples of functional variants are polypeptides derived from coding sequences with single nucleotide variations. These include SEQ ID NO: 6 and SEQ ID NO: 8 which correspond to the open reading frames of SEQ ID NO: 5, and SEQ ID NO: 7 respectively. Both polypeptides incorporate amino acid substitutions at position 28 (Pro/Thr) and 680 (Ser/Phe). It should be noted that either amino acid substitution may occur alone in the HCN1 polypeptide sequence such that any HCN1 polypeptide with either one or both of these substitutions are part of the invention.

The sequence according to SEQ ID NO: 1, SEQ ID NO: 3, SEQ ID NO: 5 or SEQ ID NO: 7 may also be used in the preparation of vector molecules for the expression of the encoded protein in suitable host cells. Also, fragments of these sequences may be cloned into an expression vector and expressed in order to determine individual functional sites along the cDNA molecule. The sequences may also be modified in that they are cloned into an expression vector either with our without the 5' and/or 3' non-coding regions. The coding region of a cDNA clone according to SEQ ID NO: 1 is shown in SEQ ID NO: 21. The coding region of a cDNA clone according to SEQ ID NO: 3 is shown in SEQ ID NO: 22. The coding region of a cDNA clone according to SEQ ID NO: 5 is shown in SEQ ID NO: 24. The coding region of a cDNA clone according to SEQ ID NO: 7 is shown in SEQ ID NO:25. The invention therefore also provides an expression vector comprising SEQ ID NO: 22, SEQ ID NO: 23, SEQ ID NO: 24 or SEQ ID NO: 25 or fragments thereof.

A wide variety of host cell and cloning vehicle combinations may be usefully employed in cloning the nucleic acid sequence coding for the HCN1 gene, the cDNA coding for HCN1 or parts thereof. For example, useful cloning vehicles may include chromosomal, non-chromosomal and synthetic DNA sequences such as various known bacterial plasmids and wider host range plasmids and vectors derived from combinations of plasmids and phage or virus DNA.

Vehicles for use in expression of the genes or a ligand-binding domain thereof of the present invention will further comprise control sequences operably linked to the nucleic acid sequence coding for a ligand-binding domain. Such control sequences generally comprise a promoter sequence and sequences which regulate and/or enhance expression levels. Of course control and other sequences can vary depending on the host cell selected.

Suitable expression vectors are for example bacterial or yeast plasmids, wide host range plasmids and vectors derived from combinations of plasmid and phage or virus DNA. Vectors derived from chromosomal DNA are also included. Furthermore an origin of replication and/or a dominant selection marker can be present in the vector according to the invention. The vectors according to the invention are suitable for transforming a host cell.

Recombinant expression vectors comprising the DNA of the invention as well as cells transformed with said DNA or said expression vector also form part of the present invention.

Suitable host cells according to the invention are bacterial host cells, yeast and other fungi, plant or animal host such as Chinese Hamster Ovary cells or monkey cells. Especially preferred cells are HEK 293. Thus, a host cell which comprises the DNA or expression vector according to the invention is also within the scope of the invention. The engineered host cells can be cultured in conventional nutrient media which can be modified e.g. for appropriate selection, amplification or induction of transcription. The culture conditions such as temperature, pH, nutrients etc. are well known to those ordinary skilled in the art.

The techniques for the preparation of the DNA or the vector according to the invention as well as the transformation or transfection of a host cell with said DNA or vector are standard and well known in the art, see for instance Sambrook et al., *Molecular Cloning: A laboratory Manual.* 2nd Ed., Cold Spring Harbor Laboratory, Cold Spring Harbor, N.Y., 1989.

The proteins according to the invention can be recovered and purified from recombinant cell cultures by common biochemical purification methods including ammonium sulfate precipitation, extraction, chromatography such as hydrophobic interaction chromatography, cation or anion exchange chromatography or affinity chromatography and high performance liquid chromatography. If necessary, also protein refolding steps can be included.

The gene products according to the present invention can be used for the in vivo or in vitro identification of novel ligands or analogs thereof. For this purpose binding studies can be performed with cells transformed with DNA according to the invention or an expression vector comprising DNA according to the invention, said cells expressing the HCN1 full length gene product according to the invention or fragments thereof.

Alternatively also the HCN1 gene products according to the invention as well as ligand-binding domains thereof can be used in an assay for the identification of functional ligands or analogs for the HCN1 gene products.

Methods to determine binding to expressed gene products as well as in vitro and in vivo assays to determine biological activity of gene products are well known. In general, expressed gene product is contacted with the compound to be tested and binding, stimulation or inhibition of a functional response is measured.

As a preferred way of detecting the binding of the ligand to the expressed protein, also signal transduction capacity may be measured.

The present invention thus provides for a quick and economic method to screen for therapeutic agents for the prevention and/or treatment of diseases related to CNS disorders such as human psychiatric and neurological dysfunction, cardiovascular dysfunction of the heart, and reproductive dysfunction and/or contraception related to $I_h$ function in testes and spermatozoa. The method is especially suited to be used for the high throughput screening of numerous potential compounds.

Compounds which activate or inhibit the function of HCN1 gene product may be employed in therapeutic treatments to activate or inhibit the polypeptides of the present invention.

Also within the scope of the invention are antibodies, especially monoclonal antibodies raised against the polypeptide molecule according to the invention. Such antibodies can be used therapeutically to inhibit HCN1 gene product function and diagnostically to detect HCN1 gene products.

The invention furthermore relates to the use of the HCN1 gene products as part of a diagnostic assay for detecting clinical abnormalities or susceptibility to any of the above disorders or investigation of different clinical outcomes in response to medical treatment related to mutations in the nucleic acid sequences encoding the HCN1 gene. Two examples single nucleotide variants are provided in this invention. Such variants or mutations may e.g. be detected by using PCR (Saiki et al., 1986, Nature, 324, 163-166). Also the relative levels of RNA can be determined using e.g. hybridization or quantitative PCR technology. The presence and the levels of the HCN1 gene products themselves can be assayed by immunological technologies such as radioimmuno assays, Western blots and ELISA using specific antibodies raised against the gene products. Such techniques for measuring RNA and protein levels are well known to the skilled artisan.

The determination of expression levels of the HCN1 gene products and variants thereof in individual patients may lead to fine tuning of treatment protocols.

Also, transgenic animals may be prepared in which the expression of the HCN1 gene is altered or abolished.

EXAMPLE 1

Full-length Sequence Identification

Proprietary databases were screened by BLAST2 for the presence of related human cDNA sequences using parts of the DNA sequence of the human HCN1 channel (Accession No AF064876) [29] and mouse HCN1 (Accession number AJ225123). A single cDNA clone (SEQ ID NO: 9) was identified from a brain cDNA library, obtained and sequenced using an ABI Prism 310 Genetic analyser (PE Biosystems). Sequencing reactions were performed using ABI Prism BigDye Terminator cycle sequencing Ready reaction kit (PE Biosystems). Each sequencing reaction contained 300 ng cDNA clone, 3.2 pmol sequencing primer, and PE Biosystems Terminator Ready reaction mix in a final volume of 20 ul. Reactions were cycled as follows: 25 cycles of 96° C. for 10 sec, 50° C. for 5 sec and 60° C. for 4 min in a PE Biosystems GeneAmp PCR system 9700. Following cycling, the extension products were precipitated by adding 2 ul 3M NaOAc (pH 4.6) and 50 ul 95% ethanol. Products were precipitated at RT for 15 min and collected by centrifugation at 14000 rpm for 20 min. Pellets were washed 2× with 70% ethanol prior to resuspension in 20 ul The published human HCN1 sequence and the 5' sequence obtained by RACE-PCR was used to design primers to PCR the region of human HCN1 flanked by the RACE-PCR product (SEQ ID NO: 13) and SEQ ID NO: 9 and covered by the published sequence. Each PCR reaction contained 1× PCR buffer (Expand High Fidelity buffer), 1.5 mM $MgCl_2$, 2□1 whole brain Marathon-Ready cDNA (Clontech), 400 nM primer 1 (HCN1PCRA 5'-TGCTGCAGCCCGGGGTCAACAAAT-3' (SEQ ID NO:37)), 400 nM primer 2 (HCN1PCRB 5'-GAGGCGGTGGGGGAGGCATAGTGG-3' (SEQ ID NO:38)), 400□M dATP, 400 μM dCTP, 400 μM dGTP, 400□M dTTP, 5% DMSO and 2.625 units Expand High Fidelity PCR enzyme mix in a total volume of 50 μl. Reactions were cycled in a MJ Research PTC-200 Thermal Cycler using the following conditions: 94° C., 2 min and 35 cycles of 24° C. for 30 sec, 60° C. for 30 sec, 72° C. for 90 sec, followed by an extension of 72° C. for 5 min. A PCR product of approximately 1.9 kb was identified, purified and sequenced as previously described (SEQ ID NO: 19). Some independently derived clones were also found to contain a single nucleotide variation (a C to T transition) indicated in SEQ ID NO: 20.

The full length sequence of HCN1 indicates that the cDNA consists of 2484 bp open reading frame (SEQ ID NO: 22) encoding an 827 amino acid channel. The functional equivalent sequence shown in SEQ ID NO: 3 comprises an 2673 bp open reading frame (SEQ ID NO: 23) encoding a 890 amino acid channel. Two single nucleotide variants were found which altered the amino acid sequence, and these are indicated in conjunction with the splice variant in SEQ ID NO: 24 and SEQ ID NO: 25. To date, four members of the hyperpolarisation-activated cation channel have been identified and cloned from mouse (HCN1-4). Full length clones of human HCN-2 and HCN-4 (Accession NOs AF065164 and AJ238850) have also been obtained whereas only a single partial sequence exists for human HCN-1. These channels share close overall homology. Analysis of the channel sequence have shown that these channels have the classic $K^+$ channel structure of 6 transmembrane domains and an ion conducting pore loop. Additionally, they possess a cyclic nucleotide binding domain. Within the transmembrane, pore and CNBD regions there is very high conservation among the channel subtypes. Alignment of the HCN1 sequences according to the invention with the other members of the HCN channel family suggest that this sequence does encode an hyperpolarisation activated ion channel. Regions of conservation between the human HCN channels are denoted by asterixes in FIG. 1. The transmembrane domains, pore regions and CNBD are underlined. Alignment of HCN1 polypeptides shows that the novel sequences do encode HCN1 channels (FIG. 2). The single amino acid variants are indicated in bold and are underscored with a # in the alignment in FIG. 2.

The cloned full length mouse HCN1 channel contains a polyglutamine repeat in the C-terminal region [29]. Expansions of polyglutamine repeats have been implicated in several neurodegenerative diseases [27]. Although no polyglutamine repeat appears to be present in the novel sequence the possibility arises of allelic variation and expansion of a polyglutamine tract resulting in increased propensity to neurodegenerative diseases. The 189 bp deletion identified in the new splice variant spans the corresponding region in the mouse HCN1 channel containing the polyglutamine repeat.

EXAMPLE 2

Tissue Distribution of SEQ ID NO: 1 and SEQ ID NO: 3

In order to analyze the expression of the ion channels comprising SEQ ID NO:1 and SEQ ID NO: 3 in different human tissues, Northern blot analysis was performed. A human Multiple Tissue Expression (MTE) Array was obtained from Clontech, which contains poly $A^+$ RNA from a variety of human tissues including nervous system, cardiovascular, digestive, and immune tissue. Prehybridization was performed in Clontech's ExpressHyb supplemented with 100 μg/ml denatured sheared salmon DNA for 2 hr at 65° C. For RNA detection, $^{32}$P labeled DNA fragments were generated with an Oligolabeling kit (High Prime, Boehringer Mannheim) using a 627 bp fragment generated from SEQ ID NO: 9. This fragment starts at a SmaI site 717 bp from the 5' end of the coding sequence and stops at the NotI cloning site (SEQ ID NO:21) and is common to both SEQ ID NO: 1 and SEQ ID NO: 3. The $^{32}$P labeled probes were hybridized to the array for 16 hours at 65° C. Subsequently, the array was washed with 2×SSC/1% SDS at 65° C. (4×20 min) followed by 2×20 min washes at 50° C. in 0.1×SSC/0.5% SDS. Filters were exposed to a phosphorscreen for 20 hr and analysed using Molecular Dynamics Storm Scan phosphorimage package.

From the results it can be concluded that human SEQ ID NO: 1 and SEQ ID NO: 3 are expressed predominantly in nervous tissue. Positive signals were detected in a variety of brain regions including cerebral cortex, cerebellum, occipital lobe, temporal lobe and nucleus accumbens, Weaker expression was observed in fetal brain. Peripherally, only weak expression was detected in atrial tissue of the heart.

EXAMPLE 3

Tissue Distribution of SEQ ID: 1 and 3 in Nervous Tissue

In order to further analyze the expression of the ion channels comprising SEQ ID NO:1 and SEQ ID NO: 3 in nervous tissue, Northern blot analysis was performed. A human Multiple Tissue Northern was obtained from Clontech (Human Brain MTN Blot II), which contains poly $A^+$ RNA from a variety of brain regions. Prehybridization was performed in Clontech's ExpressHyb for 2 hr at 65° C. For RNA detection, $^{32}$P labeled DNA fragments were generated as described previously for MTE array. The $^{32}$P labeled probes were hybridized to the filters for 16 hours at 65° C. Subsequently, the filters were washed with 2×SSC/0.05% SDS at room temperature (2×40 min) followed by 2×20 min washes at 50° C. in 0.1×SSC/0.1% SDS. Filters were exposed to a phosphorimager screen for 20 hr and analysed using Molecular Dynamics Storm Scan phosphorimage package.

From the results it can be concluded that human SEQ ID NO: 1 and SEQ ID NO: 3 are expressed in a variety of nervous tissue. Multiple transcripts were detected in a cerebral cortex, cerebellum, occipital lobe, temporal lobe and frontal lobe. Weaker expression was observed in putamen and medulla, with no expression in spinal cord.

EXAMPLE 4

Functional Assay for Detecting HCN1 Channel Currents

Human HCN1 channel currents were detected under voltage-clamp using the whole-cell configuration of the patch-clamp technique. Appropriate cells (HEK293) expressing human HCN1 channel subunits were placed in a recording chamber containing extracellular solution (Sodium chloride 135 mM; Potassium chloride 5 mM; Calcium chloride 1.8 mM; Magnesium chloride 0.5 mM; HEPES 5 mM) at a temperature of 20-25 degrees centigrade. In some experiments the extracellular solution contained 30 mM Potassium chloride, in which cases the Sodium chloride concentration was reduced to 110 mM. The glass pipettes used for recording contained pipette solution (Sodium chloride 10 mM; Potassium chloride 130 mM; Magnesium chloride 0.5 mM; HEPES 5 mM; EGTA 1 mM) Using standard equipment and methodology, a cell was voltage-clamped at a holding potential of −40 mV (not allowing for liquid junction potentials). The membrane current was recorded throughout the experiment. To determine the current-voltage relationship of human HCN1 channels, every 8 seconds the membrane potential was stepped sequentially to the following values (in mV) for 2 or 3 seconds each: −20, −40, −60, −80, −100, −120, −140 (FIGS. 5 and 6). To determine the effects of caesium chloride (5 mM) or ZD 7288 (100 micromolar) on human HCN1 channel currents, t every 8 or 10 seconds the cell potential was hyperpolarised to a potential of −120 mV (not allowing for liquid junction potentials) for 1-5 seconds and the potential then returned to the holding potential of −40 mV. The membrane current was measured just after (1-10 milliseconds) the start of the hyperpolarising step and just before (10-100 milliseconds) its end. The difference in these two values of membrane current was taken as the amplitude of the current due to the human HCN1 channel subunits. For each cell, the current amplitude was determined first in normal extracellular solution and then in extracellular solution containing caesium chloride (FIG. 3) or ZD 7288 (FIGS. 4 and 7). Alternatively, the effect of caesium chloride (5 mM) on human HCN1 channel currents was determined by measuring the current-voltage relationship in normal extracellular solution and also in extracellular solution containing caesium chloride (FIG. 6). Human HCN1 channel currents were reduced by caesium chloride (5 mM) and by ZD 7288 (100 micromolar) [17, 25].

A clone which has the following characteristics is considered to be an $I_h$ ion channel:

Template suppression reagent (PE Biosystems) for sequencing. This clone encoded the 3' end of human HCN-1. The sequence is shown in SEQ ID NOs: 9.

The presence of a second splice variant was confirmed by PCR using primers designed against the published sequence flanking either side of the 189 bp deletion identified in SEQ ID NO: 9 compared to the published sequence. Each PCR reaction contained 1×PCR buffer (Expand High Fidelity buffer), 1.5 mM $MgCl_2$, 2□1 whole brain Marathon-Ready cDNA (Clontech), 400 nM primer 1 and 2 (HCN1SPLICEA 5'-TGCTGCAGCCCGGGGTCAACAAAT-3' (SEQ ID NO:26) and HCN1SPLICE B 5'-CTCCTGCCCCCTGCCT-GAAG-3' (SEQ ID NO:27), or HCN1SPLICEC 5'-TCTAC-TACGACCCCGACCTC-3' (SEQ ID NO:28) and HCN1SPLICED 5'-TGGCTCCCGACGACATCT-3' (SEQ ID NO:29)), 400□M dATP, 400 μM dCTP, 400□M dGTP, 400□M dTTP, 5% DMSO and 2.625 units Expand High Fidelity PCR enzyme mix in a total volume of 50□1. Reactions were cycled in a MJ Research PTC-200 Thermal Cycler using the following conditions: 94° C., 2 mm and 35 cycles of 24° C. for 30 sec, 60° C. for 30 sec, 72° C. for 90 sec, followed by an extension of 72° C. for 5 mm. PCR products of approximately 560 bp (HCN1SPLICEA and HCN1SPLICEB) and 600 bp (HCN1SPLICEC and HCN1SPLICED) were identified, purified and sequenced as previously described (SEQ ID NO: 17). This sequence had no deletion compared to the published sequence. Several independently derived clones were observed to contain a single nucleotide variant (a C to T transition) shown in SEQ ID NO: 11 which results in a change in amino acid (Ser to Phe) in SEQ ID NO: 12.

Primers were designed using the known human HCN1 sequence to attempt to obtain the 5' end of HCN1 by RACE-PCR using Clontech SMART RACE cDNA amplification kit. SMART 5'-RACE-ready cDNA was synthesised as follows, 1 μg of hippocampal polyA$^+$ RNA was mixed with 2 μM 5'-RACE cDNA synthesis primer (Clontech 5'-$(T)_{25}N_{-1}N$-3') and 2 M SMART II oligonucleotide (Clontech 5'-AAGCAGTGGTAACAACGCAGAG-TACGCGGG-3' (SEQ ID NO: 30)) in a total volume of 5 μl. Tubes were incubated at 70° C. for 2 min and cooled on ice for a further 2 min. The following was then added, 1× First strand buffer (50 mM Tris-HCl pH8.3, 75 mM KCl and 6 mM $MgCl_2$), 2 mM DTT, 1 mM dATP, 1 mM dCTP, 1 mM dGTP, 1 mM dTTP and 200 u MMLV reverse transcriptase. The reactions were incubated at 42° C. for 1.5 hr in an air incubator. The reaction product was diluted with 250 ul Tricine-EDTA buffer and heated at 72° C. for 7 min prior to storage at 20° C.

Each RACE-PCR reaction contained 1×PCR buffer (Clontech Advantage-GC 2 PCR buffer, 40 mM Tricine-KOH pH9.2, 15 mM KOAc, 3.5 mM $Mg(OAc)_2$, 5% DMSO, 187.5 ng BSA, 0.005% Nonidet P-40 and 0.005% Tween-20), 200 uM dATP, 200 uM dCTP, 200 uM dGTP, 200 uM dTTP, 2.5 ul RACE-ready cDNA, Clontech Universal primer mix (20 nM long primer 5'-CTAATACGACT-CACTATAGGGCAAGCAGTGGTAACAACGCAGAGT-3' (SEQ ID NO:31), 100 nM short primer 5'-AAGCAGTGGTAACAACGCAGACT-3'SEQ ID NO:32), 200 nM Gene Specific Primer (BCNG1R2, 5'-CTGGCTGTCTFfGTAAACTFITCAGATCCATFF-3' (SEQ ID NO: 33), BCNG1R3 5'-CTGTAAGGGTG-GATAATCCAGAAGCCTGC-3' (SEQ ID NO: 34), BCNG R4B, 5'-TTCTGGCTCCCAAACATGCGGAGG-3' (SEQ ID NO: 35)), 1× Advantage-GC 2 polymerase mix (1% glycerol, 0.3 mM Tris-HCl pH 8.0, 1.5 mM KCl, 1 uM EDTA) and 0.5M GC-melt (Clontech) in a total volume of 50 ul. Reactions were cycled in a MJ Research PTC-200 Thermal Cycler using the following conditions: 95° C., 3 min and 40 cycles of 94° C. for 20 sec, 65° C. for 20 sec, 72° C. for 90 sec, followed by an extension of 72° C. for 5 min. A PCR product of approximately 300 bp was identified, purified and sequenced as previously described. RACE-PCR generated novel sequence information of 153 bp upstream of published human HCN1 sequence SEQ ID NO: 13.

SEQ ID NO: 13 was used to screen by BLAST2 human public EST and genomic databases available from EMBL [31]. A human genomic bacterial artificial chromosome (BAC) clone (RP11 -398G9: accession number AC013384) that contained sequence similarity was identified from the high throughput genomic division of the EMBL release 62. The region corresponding to human HCN-1 was sequenced as described previously. This clone appeared to encode the 5' end of human HCN-1 including the translation initiation codon. The sequences are shown in SEQ ID NO: 14. Several independently derived clones were found to have a single nucleotide variant (a C to A transition) indicated in SEQ ID NO: 15 resulting in a change of amino acid from Pro to Thr.

1. It opens through hyperpolarisation and closes at positive voltage values ($V_m$-10 mV;
2. Whose activation and deactivation proceeds with a relatively slow time course;
3. Which conducts not only $K^+$ ions but also $Na^+$ ions;
4. Which are blocked preferentially by extracellular caesium ions rather than by extracellular barium ions.
5. Which are directly modulated by cyclic nucleotides, particularly cAMP and cGMP

BRIEF DESCRIPTION OF THE DRAWING

FIG. 1: CLUSTAL W Multiple Sequence Alignments of SEQ ID NO: 2 SEQ ID NO: 4, SEQ ID NO: 6 and SEQ ID NO: 8 with human HCN1 (SEQ ID NO:36), human HCN2 (SEQ ID NO:39) and human HCN4 (SEQ ID NO: 40).

FIG. 2: CLUSTAL W Multiple Sequence Alignments of SEQ ID NO: 2, SEQ ID NO: 4, SEQ ID NO: 6 and SEQ ID NO: 8 with rat (SEQ ID NO: 41), mouse (SEQ ID NO: 42) and partial human HCN1 (SEQ ID NO: 43) channels.

FIG. 3: Effect of caesium chloride (5 mM) on hHCN1 (full-length) currents. Whole-cell patch-clamp recording from a HEK 293F cell transfected with an expression vector containing SEQ ID NO 7. Panel A: each data point represents a measurement from one data sweep. Caesium chloride was added to the bathing medium for the time represented by the bar above the data points. Panel B: representative data sweeps (corresponding letters in panels A & B identify the times at which the sweeps in panel B were taken). Inward membrane currents in panel B are plotted as negative quantities (following convention), but the amplitude of hHCN1 current in panel A is plotted as a positive value.

FIG. 4: Effect of ZD 7288 (100 micromolar) on hHCN1 (full-length) currents. Whole-cell patch-clamp recording from a HEK 293F cell transfected with an expression vector containing SEQ ID NO 7. Panel A: each data point represents a measurement from one data sweep. ZD 7288 was added to the bathing medium for the time represented by the bar above the data points. Panel B: representative data sweeps (corresponding letters in panels A & B identify the times at which the sweeps in panel B were taken). Inward membrane currents in panel B are plotted as negative quantities (following convention), but the amplitude of hHCN1 current in panel A is plotted as a positive value.

FIG. 5: Current-voltage relationships of whole-cell patch-clamp recordings from HEK 293F cells transfected with DNA for hHCN1. Panel A: SEQ ID NO 5. Panel B: SEQ ID NO 7. For each panel, the upper traces display the currents evoked by the voltage steps shown in the lower traces.

REFERENCES

Figure 6:
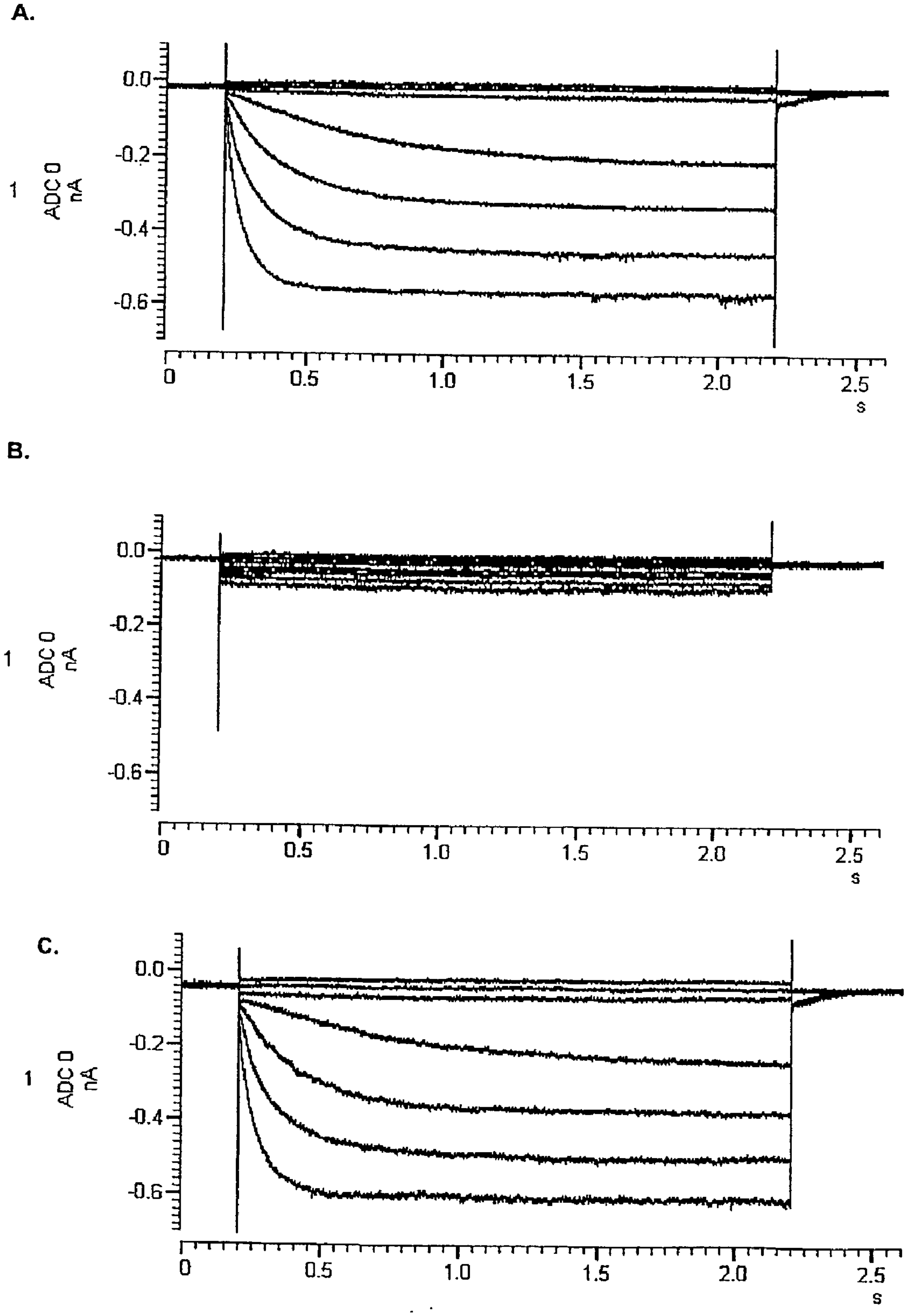
FIG. 6: Current-voltage relationship and block by caesium chloride of hHCN1 current. Whole-cell patch-clamp recording from a HEK 293F cell transfected with DNA expressing SEQ ID NO:3. Each panel shows the currents evoked by voltage commands (voltage traces not shown). Panel A: normal extracellular solution. Panel B: extracellular solution containing 5 mM caesium chloride. Panel C: return to normal extracellular solution. All panels from the same cell.
Figure 7:
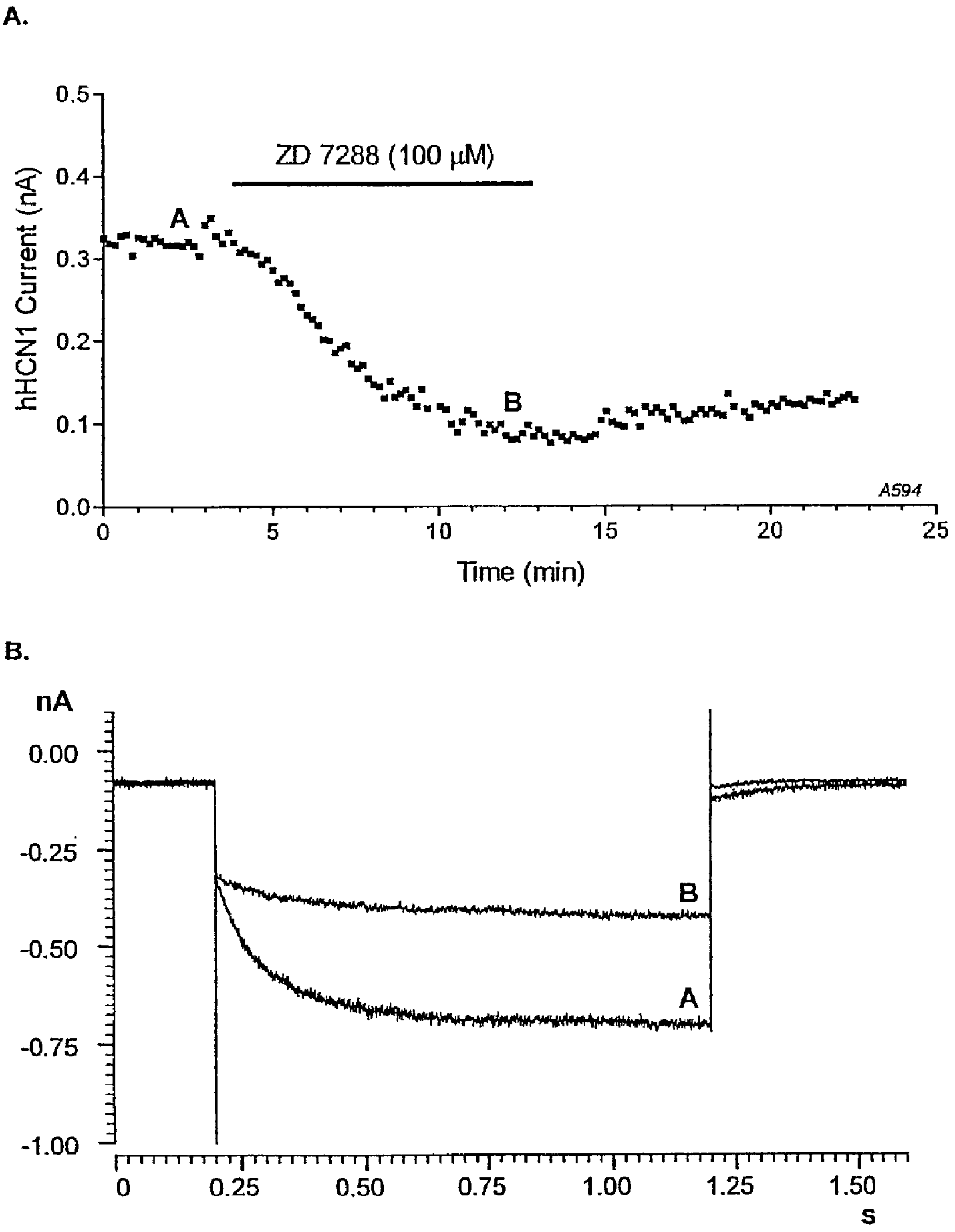
FIG. 7: Effect of ZD 7288 (100 micromolar) on hHCN1 current. Whole-cell patch-clamp recording from a HEK 293 cell transfected with KDNA expressing SEQ ID NO:3. Panel A: each data point represents a measurement from one data sweep. ZD 7288 was added to the bathing medium for the time represented by the bar above the data points. Panel B: representative data sweeps (corresponding letters in panels A & B identify the times at which the sweeps in panel B were taken). Note that inward membrane currents in panel B are plotted as negative quantities (following convention), but that the amplitude of hHCN1 current in panel A is plotted as a positive value.

[1] North, R. A. (ed) (1995) Ligand- and Voltage-gated Ion Channels, CRC Press,
[2] Attwell, D. and Wilson, M. (1980) Journal of Physiology 309, 287-315.
[3] Bader, C. R. and Bertrand, D. (1984) Journal of Physiology 347, 611-631.
[4] Bal, T. and McCormick, D. A. (1996) Neuron 17, 297-308.
[5] Bal, T. and McCormick, D. A. (1997) Journal of Neurophysiology 77, 3145-3156.
[6] Barnes, S. and Hille, B. (1989) Journal of General Physiology 94, 719-743.
[7] Beaumont, V. and Zucker, R.S. (2000) Nature Neuroscience 3, 133-141.
[8] Brown, H F and Ho, W K. (1996) in: Molecular physiology and pharmacology of cardiac ion channels and transporters. (Morad, M., Ebashi, S., Trautwein, W., and Kurachi, Y., Eds.) pp. 17-30 Kluwert Academic Publishers, Dordrecht
[9] Clapham, D. E. (1998) Neuron 21, 5-7.
[10] DiFrancesco, D. (1981) Journal of Physiology 314, 359-376.
[11] DiFrancesco, D. (1993) Annual Review of Physiology 55, 455-472.
[12] DiFrancesco, D. (1996) in: Molecular physiology and pharmacology of cardiac ion channels and transporters. (Morad, M., Ebashi, S., Trautwein, W., and Kurachi, Y., Eds.) pp. 31-37 Kluwer Academic Publishers, Dordrecht
[13] DiFrancesco, D. and Mangoni, M. (994) Journal of Physiology 474, 473-482.
[14] Gasparini, S. and DiFrancesco, D. (1997) Pflugers Archiv—European Journal of Physiology 435, 99-106.
[15] Gauss, R., Seifert, R., and Kaupp, U. B. (1998) Nature 393, 583-587.
[16] Halliwell, J. V. and Adams, P. R. (1982) Brain Research 250, 71-92.
[17] Harris, N. C. and Constanti, A. (1995) Journal of Neurophysiology 74, 2366-2378.
[18] Hille, B. (1992) Ionic Channels of Excitable Membranes, Sinauer Associates,
[19] Ludwig, A., Zong, X., Jeglitsch, M., Hofmann, F., and Biel, M. (1998) Nature 393, 587-591.
[20] Luthi, A. and McCormick, D. A. (1998) Neuron 21, 9-12.
[21] Maccaferri, G. and McBain, C. J. (1996) Journal of Physiology 497, 119-130.
[22] Magee, J. C. (1999) Nature Neuroscience 2, 508-514.
[23] McCormick, D. A. and Pape, H. C. (1990) Journal of Physiology 431, 291-318.
[24] Moosmang, S., Biel, M., Hofmann, F., and Ludwig, A. (1999) Biol. 380, 975-980.
[25] Pape, H. C. (1996) Annual Review of Physiology 58, 299-327.
[26] Rekling, J. C. and Feldman, J. L. (1998) Annual Review of Physiology 60, 385-405.
[27] Ross, C. A., Wood, J. D., Schilling, G., Peters, M. F., Nucifora, F. C. J., Cooper, J. K. et al. (1999) Philosophical Transactions of the Royal Society of London—Series B: Biological Sciences 354, 1005-1011.
[28] Santoro, B., Grant, S. G. N., Bartsch, D., and Kandel, E. R. (1997) Proc. 94, 14815-14820.
[29] Santoro, B., Liu, D. T., Yao, H., Bartsch, D., Kandel, E. R., Siegelbaum, S. A. et al. (1998) Cell 93, 717-729.
[30] Seifert, R., Scholten, A., Gauss, R., Mincheva, A., Lichter, P., and Kaupp, U. B. (1999) Proc. 96, 9391-9396.
[31] Stoesser, G., Tuli, M. A., Lopez, R., and Sterk, P. (1999) Nucleic Acids Research 27, 18-24.
[32] Strata, F., Atzori, M., Molnar, M., Ugolini, G., Tempia, F., and Cherubini, E. (1997) Journal of Neuroscience 17, 1435-1446.
[33] Wickman, K., Nemec, J., Gendler, S. J., and Clapham, D. E. (1998) Neuron 20, 103-114.

We claim:

1. An isolated DNA sequence encoding a full length human hyperpolarized activated ion channel of the HCN 1 subtype, comprising:

SEQ ID: 5.

2. An isolated DNA sequence comprising SEQ ID NO: 22 or SEQ ID NO: 24.

3. An isolated DNA sequence comprising SEQ ID NO: 23 or SEQ ID NO: 25.

4. An isolated DNA sequence comprising SEQ ID NO: 3 or SEQ ID NO: 7.

5. An isolated, full length human hyperpolarized activated ion channel of the HCN1 subtype, comprising an amino acid sequence selected from the group consisting of SEQ ID NO: 2, SEQ ID NO: 4, SEQ ID NO: 6 and SEQ ID NO: 8.

6. The isolated, full length human hyperpolarized activated ion channel of the HCN 1 subtype of claim 5, comprising:

SEQ ID NO: 6.

7. The isolated, full length hyperpolarized activated ion channel of the HCN1 subtype of claim 5, comprising SEQ ID NO:8.

8. An in vitro screening assay for the selection of compounds that bind the human hyperpolarised activated ion channel of the HCN 1 subtype, comprising:

providing cells expressing the full length human hyperpolarized activated ion channel of the HCN 1 subtype according to claim 5, contacting the compounds with the full length human hyperpolarized activated ion channel of the HCN 1 subtype, and determining whether the compounds bind specifically to the full length human hyperpolarized activated ion channel of HCN 1 subtype.

9. A method to screen for compounds that influence a function of the human hyperpolarised activated ion channel of the HCN 1 subtype, comprising:

assaying compounds with the full length human hyperpolarized activated ion channel of the HCN 1 subtype according to claim 5 to determine whether the compounds activate or inhibit said ion channel.

10. An isolated expression vector comprising SEQ ID NO: 22, SEQ ID NO: 24, SEQ ID NO: 23, SEQ ID NO: 25.

* * * * *

SEQUENCE LISTING

<160> NUMBER OF SEQ ID NOS: 25
<210> SEQ ID NO 1
<211> LENGTH: 2791
<212> TYPE: DNA
<213> ORGANISM: Homo sapiens

<400> SEQUENCE: 1

```
ccgtcgccgg ccgcgtcctc cgggcatgga aggaggcggc aagcccaact cttcgtctaa      60

cagccgggac gatggcaaca gcgtcttccc cgccaaggcg tccgcgccgg gcgcggggcc     120

ggccgcggcc gagaagcgcc tgggcacccc gccgggggc  ggcggggccg gcgcgaagga     180

gcacggcaac tccgtgtgct tcaaggtgga cggcggtggc ggcggtggcg gcggcggcgg     240

cggcggcgag gagccggcgg ggggcttcga agacgccgag gggccccggc ggcagtacgg     300

cttcatgcag aggcagttca cctccatgct gcagcccggg gtcaacaaat tctccctccg     360

catgtttggg agccagaagg cggtggaaaa ggagcaggaa agggttaaaa ctgcaggctt     420
```

-continued

```
ctggattatc caccccttaca gtgatttcag gttttactgg gatttaataa tgcttataat    480
gatggttgga aatctagtca tcataccagt tggaatcaca ttctttacag agcaaacaac    540
aacaccatgg attattttca atgtggcatc agatacagtt ttcctattgg acctgatcat    600
gaattttagg actgggactg tcaatgaaga cagttctgaa atcatcctgg accccaaagt    660
gatcaagatg aattatttaa aaagctggtt tgtggttgac ttcatctcat ccatcccagt    720
ggattatatc tttcttattg tagaaaaagg aatggattct gaagtttaca agacagccag    780
ggcacttcgc attgtgaggt ttacaaaaat tctcagtctc ttgcgtttat tacgactttc    840
aaggttaatt agatacatac atcaatggga agagatattc cacatgacat atgatctcgc    900
cagtgcagtg gtgagaattt ttaatctcat cggcatgatg ctgctcctgt gccactggga    960
tggttgtctt cagttcttag taccactact gcaggacttc ccaccagatt gctgggtgtc   1020
tttaaatgaa atggttaatg attcttgggg aaagcagtat tcatacgcac tcttcaaagc   1080
tatgagtcac atgctgtgca ttgggtatgg agcccaagcc ccagtcagca tgtctgacct   1140
ctggattacc atgctgagca tgatcgtcgg ggccacctgc tatgccatgt ttgtcggcca   1200
tgccaccgct ttaatccagt ctctggattc ttcgaggcgg cagtatcaag agaagtataa   1260
gcaagtggaa caatacatgt cattccataa gttaccagct gatatgcgtc agaagataca   1320
tgattactat gaacacagat accaaggcaa aatctttgat gaggaaaata ttctcaatga   1380
actcaatgat cctctgagag aggagatagt caacttcaac tgtcggaaac tggtggctac   1440
aatgccttta tttgctaatg cggatcctaa ttttgtgact gccatgctga gcaagttgag   1500
atttgaggtg tttcaacctg gagattatat catacgagaa ggagccgtgg gtaaaaaaat   1560
gtatttcatt caacacggtg ttgctggtgt cattacaaaa tccagtaaag aaatgaagct   1620
gacagatggc tcttactttg gagagatttg cctgctgacc aaaggacgtc gtactgccag   1680
tgttcgagct gatacatatt gtcgtcttta ctcactttcc gtggacaatt tcaacgaggt   1740
cctggaggaa tatccaatga tgaggagagc ctttgagaca gttgccattg accgactaga   1800
tcgaatagga aagaaaaatt caattcttct gcaaaagttc cagaaggatc tgaacactgg   1860
tgttttcaac aatcaggaga acgaaatcct caagcagatt gtgaaacatg acagggagat   1920
ggtgcaggca atcgctccca tcaattatcc tcaaatgaca accctgaatt ccacatcgtc   1980
tactacgacc ccgacctccc gcatgaggac acaatctcca ccggtgtaca cagcgaccag   2040
cctgtctcac agcaacctgc actcccccag tcccagcaca cagacccccc agccatcagc   2100
catcctgtca ccctgctcca cgccgaaaaa tgaagtgcac aagagcacgc aggcgcttca   2160
caacaccaac ctgacccggg aagtcaggcc actctccgcc tcgcagccct cgctgcccca   2220
tgaggtgtcc actctgattt ccagacctca tcccactgtg ggcgagtccc tggcctccat   2280
ccctcaaccc gtgacggcgg tccccggaac gggccttcag gcagggggca ggagcactgt   2340
cccgcagcgc gtcaccctct tccgacagat gtcgtcggga gccatccccc cgaaccgagg   2400
agtccctcca gcacccccctc caccagcagc tgctcttcca agagaatctt cctcagtctt   2460
aaacacagac ccagacgcag aaaagccacg atttgcttca aatttatgat ccctgctgat   2520
tgtcaaagca gaaagaaata ctctcataaa ctgagactat actcagatct tattttattc   2580
tatctcctga tagatccctc tagcctacta tgaagagata ttttagacag ctgtggccta   2640
cacgtgaaat gtaaaaatat atatacatat actataaaat atatatctaa attcccaaga   2700
gagggtcaaa agacctgttt agcattcagt gttatatgtc ttcctttctt taaatcatta   2760
```

-continued

```
aaggatttaa aatgtcaaaa aaaaaaaaaa a                                2791


<210> SEQ ID NO 2
<211> LENGTH: 827
<212> TYPE: PRT
<213> ORGANISM: Homo sapiens

<400> SEQUENCE: 2

Met Glu Gly Gly Gly Lys Pro Asn Ser Ser Ser Asn Ser Arg Asp Asp
  1               5                  10                  15

Gly Asn Ser Val Phe Pro Ala Lys Ala Ser Ala Pro Gly Ala Gly Pro
             20                  25                  30

Ala Ala Ala Glu Lys Arg Leu Gly Thr Pro Pro Gly Gly Gly Gly Ala
         35                  40                  45

Gly Ala Lys Glu His Gly Asn Ser Val Cys Phe Lys Val Asp Gly Gly
     50                  55                  60

Gly Gly Gly Gly Gly Gly Gly Gly Gly Gly Glu Glu Pro Ala Gly Gly
 65                  70                  75                  80

Phe Glu Asp Ala Glu Gly Pro Arg Arg Gln Tyr Gly Phe Met Gln Arg
                 85                  90                  95

Gln Phe Thr Ser Met Leu Gln Pro Gly Val Asn Lys Phe Ser Leu Arg
            100                 105                 110

Met Phe Gly Ser Gln Lys Ala Val Glu Lys Glu Gln Glu Arg Val Lys
        115                 120                 125

Thr Ala Gly Phe Trp Ile Ile His Pro Tyr Ser Asp Phe Arg Phe Tyr
    130                 135                 140

Trp Asp Leu Ile Met Leu Ile Met Met Val Gly Asn Leu Val Ile Ile
145                 150                 155                 160

Pro Val Gly Ile Thr Phe Phe Thr Glu Gln Thr Thr Thr Pro Trp Ile
                165                 170                 175

Ile Phe Asn Val Ala Ser Asp Thr Val Phe Leu Leu Asp Leu Ile Met
            180                 185                 190

Asn Phe Arg Thr Gly Thr Val Asn Glu Asp Ser Ser Glu Ile Ile Leu
        195                 200                 205

Asp Pro Lys Val Ile Lys Met Asn Tyr Leu Lys Ser Trp Phe Val Val
    210                 215                 220

Asp Phe Ile Ser Ser Ile Pro Val Asp Tyr Ile Phe Leu Ile Val Glu
225                 230                 235                 240

Lys Gly Met Asp Ser Glu Val Tyr Lys Thr Ala Arg Ala Leu Arg Ile
                245                 250                 255

Val Arg Phe Thr Lys Ile Leu Ser Leu Leu Arg Leu Leu Arg Leu Ser
            260                 265                 270

Arg Leu Ile Arg Tyr Ile His Gln Trp Glu Glu Ile Phe His Met Thr
        275                 280                 285

Tyr Asp Leu Ala Ser Ala Val Val Arg Ile Phe Asn Leu Ile Gly Met
    290                 295                 300

Met Leu Leu Leu Cys His Trp Asp Gly Cys Leu Gln Phe Leu Val Pro
305                 310                 315                 320

Leu Leu Gln Asp Phe Pro Pro Asp Cys Trp Val Ser Leu Asn Glu Met
                325                 330                 335

Val Asn Asp Ser Trp Gly Lys Gln Tyr Ser Tyr Ala Leu Phe Lys Ala
            340                 345                 350

Met Ser His Met Leu Cys Ile Gly Tyr Gly Ala Gln Ala Pro Val Ser
        355                 360                 365
```

-continued

```
Met Ser Asp Leu Trp Ile Thr Met Leu Ser Met Ile Val Gly Ala Thr
    370                 375                 380

Cys Tyr Ala Met Phe Val Gly His Ala Thr Ala Leu Ile Gln Ser Leu
385                 390                 395                 400

Asp Ser Ser Arg Arg Gln Tyr Gln Glu Lys Tyr Lys Gln Val Glu Gln
                405                 410                 415

Tyr Met Ser Phe His Lys Leu Pro Ala Asp Met Arg Gln Lys Ile His
            420                 425                 430

Asp Tyr Tyr Glu His Arg Tyr Gln Gly Lys Ile Phe Asp Glu Glu Asn
        435                 440                 445

Ile Leu Asn Glu Leu Asn Asp Pro Leu Arg Glu Glu Ile Val Asn Phe
    450                 455                 460

Asn Cys Arg Lys Leu Val Ala Thr Met Pro Leu Phe Ala Asn Ala Asp
465                 470                 475                 480

Pro Asn Phe Val Thr Ala Met Leu Ser Lys Leu Arg Phe Glu Val Phe
                485                 490                 495

Gln Pro Gly Asp Tyr Ile Ile Arg Glu Gly Ala Val Gly Lys Lys Met
            500                 505                 510

Tyr Phe Ile Gln His Gly Val Ala Gly Val Ile Thr Lys Ser Ser Lys
        515                 520                 525

Glu Met Lys Leu Thr Asp Gly Ser Tyr Phe Gly Glu Ile Cys Leu Leu
    530                 535                 540

Thr Lys Gly Arg Arg Thr Ala Ser Val Arg Ala Asp Thr Tyr Cys Arg
545                 550                 555                 560

Leu Tyr Ser Leu Ser Val Asp Asn Phe Asn Glu Val Leu Glu Glu Tyr
                565                 570                 575

Pro Met Met Arg Arg Ala Phe Glu Thr Val Ala Ile Asp Arg Leu Asp
            580                 585                 590

Arg Ile Gly Lys Lys Asn Ser Ile Leu Leu Gln Lys Phe Gln Lys Asp
        595                 600                 605

Leu Asn Thr Gly Val Phe Asn Asn Gln Glu Asn Glu Ile Leu Lys Gln
    610                 615                 620

Ile Val Lys His Asp Arg Glu Met Val Gln Ala Ile Ala Pro Ile Asn
625                 630                 635                 640

Tyr Pro Gln Met Thr Thr Leu Asn Ser Thr Ser Ser Thr Thr Thr Pro
                645                 650                 655

Thr Ser Arg Met Arg Thr Gln Ser Pro Pro Val Tyr Thr Ala Thr Ser
            660                 665                 670

Leu Ser His Ser Asn Leu His Ser Pro Ser Pro Ser Thr Gln Thr Pro
        675                 680                 685

Gln Pro Ser Ala Ile Leu Ser Pro Cys Ser Thr Pro Lys Asn Glu Val
    690                 695                 700

His Lys Ser Thr Gln Ala Leu His Asn Thr Asn Leu Thr Arg Glu Val
705                 710                 715                 720

Arg Pro Leu Ser Ala Ser Gln Pro Ser Leu Pro His Glu Val Ser Thr
                725                 730                 735

Leu Ile Ser Arg Pro His Pro Thr Val Gly Glu Ser Leu Ala Ser Ile
            740                 745                 750

Pro Gln Pro Val Thr Ala Val Pro Gly Thr Gly Leu Gln Ala Gly Gly
        755                 760                 765

Arg Ser Thr Val Pro Gln Arg Val Thr Leu Phe Arg Gln Met Ser Ser
    770                 775                 780

Gly Ala Ile Pro Pro Asn Arg Gly Val Pro Pro Ala Pro Pro Pro Pro
```

-continued

```
785                 790                 795                 800

Ala Ala Ala Leu Pro Arg Glu Ser Ser Ser Val Leu Asn Thr Asp Pro
                805                 810                 815

Asp Ala Glu Lys Pro Arg Phe Ala Ser Asn Leu
            820                 825
```

<210> SEQ ID NO 3
<211> LENGTH: 2980
<212> TYPE: DNA
<213> ORGANISM: Homo sapiens

<400> SEQUENCE: 3

```
ccgtcgccgg ccgcgtcctc cgggcatgga aggaggcggc aagcccaact cttcgtctaa     60

cagccgggac gatggcaaca gcgtcttccc cgccaaggcg tccgcgccgg gcgcggggcc    120

ggccgcggcc gagaagcgcc tgggcacccc gccggggggc ggcggggccg gcgcgaagga    180

gcacggcaac tccgtgtgct tcaaggtgga cggcggtggc ggcggtggcg gcggcggcgg    240

cggcggcgag gagccggcgg ggggcttcga agacgccgag gggccccggc ggcagtacgg    300

cttcatgcag aggcagttca cctccatgct gcagcccggg gtcaacaaat tctccctccg    360

catgtttggg agccagaagg cggtggaaaa ggagcaggaa agggttaaaa ctgcaggctt    420

ctggattatc cacccttaca gtgatttcag gttttactgg gatttaataa tgcttataat    480

gatggttgga aatctagtca tcataccagt tggaatcaca ttctttacag agcaaacaac    540

aacaccatgg attattttca atgtggcatc agatacagtt ttcctattgg acctgatcat    600

gaattttagg actgggactg tcaatgaaga cagttctgaa atcatcctgg accccaaagt    660

gatcaagatg aattatttaa aaagctggtt tgtggttgac ttcatctcat ccatcccagt    720

ggattatatc tttcttattg tagaaaaagg aatggattct gaagtttaca agacagccag    780

ggcacttcgc attgtgaggt ttacaaaaat tctcagtctc ttgcgtttat tacgactttc    840

aaggttaatt agatacatac atcaatggga agagatattc cacatgacat atgatctcgc    900

cagtgcagtg gtgagaattt ttaatctcat cggcatgatg ctgctcctgt gccactggga    960

tggttgtctt cagttcttag taccactact gcaggacttc ccaccagatt gctgggtgtc   1020

tttaaatgaa atggttaatg attcttgggg aaagcagtat tcatacgcac tcttcaaagc   1080

tatgagtcac atgctgtgca ttgggtatgg agcccaagcc ccagtcagca tgtctgacct   1140

ctggattacc atgctgagca tgatcgtcgg ggccacctgc tatgccatgt ttgtcggcca   1200

tgccaccgct ttaatccagt ctctggattc ttcgaggcgg cagtatcaag agaagtataa   1260

gcaagtggaa caatacatgt cattccataa gttaccagct gatatgcgtc agaagataca   1320

tgattactat gaacacagat accaaggcaa aatctttgat gaggaaaata ttctcaatga   1380

actcaatgat cctctgagag aggagatagt caacttcaac tgtcggaaac tggtggctac   1440

aatgccttta tttgctaatg cggatcctaa ttttgtgact gccatgctga gcaagttgag   1500

atttgaggtg tttcaacctg gagattatat catacgagaa ggagccgtgg gtaaaaaaat   1560

gtatttcatt caacacggtg ttgctggtgt cattacaaaa tccagtaaag aaatgaagct   1620

gacagatggc tcttactttg gagagatttg cctgctgacc aaaggacgtc gtactgccag   1680

tgttcgagct gatacatatt gtcgtcttta ctcactttcc gtggacaatt tcaacgaggt   1740

cctggaggaa tatccaatga tgaggagagc ctttgagaca gttgccattg accgactaga   1800

tcgaatagga aagaaaaatt caattcttct gcaaaagttc cagaaggatc tgaacactgg   1860

tgttttcaac aatcaggaga acgaaatcct caagcagatt gtgaaacatg acagggagat   1920
```

-continued

```
ggtgcaggca atcgctccca tcaattatcc tcaaatgaca accctgaatt ccacatcgtc   1980

tactacgacc ccgacctccc gcatgaggac acaatctcca ccggtgtaca cagcgaccag   2040

cctgtctcac agcaacctgc actcccccag tcccagcaca cagaccccccc agccatcagc   2100

catcctgtca ccctgctcct acaccaccgc ggtctgcagc cctcctgtac agagccctct   2160

ggccgctcga actttccact atgcctcccc caccgcctcc cagctgtcac tcatgcaaca   2220

gcagccgcag cagcaggtac agcagtccca gccgccgcag actcagccac agcagccgtc   2280

cccgcagcca cagacacctg gcagctccac gccgaaaaat gaagtgcaca agagcacgca   2340

ggcgcttcac aacaccaacc tgacccggga agtcaggcca ctctccgcct cgcagccctc   2400

gctgccccat gaggtgtcca ctctgatttc cagacctcat cccactgtgg gcgagtccct   2460

ggcctccatc cctcaacccg tgacggcggt ccccggaacg ggccttcagg caggggggcag   2520

gagcactgtc ccgcagcgcg tcaccctctt ccgacagatg tcgtcgggag ccatcccccc   2580

gaaccgagga gtccctccag cacccccctcc accagcagct gctcttccaa gagaatcttc   2640

ctcagtctta aacacagacc cagacgcaga aaagccacga tttgcttcaa atttatgatc   2700

cctgctgatt gtcaaagcag aaagaaatac tctcataaac tgagactata ctcagatctt   2760

attttattct atctcctgat agatccctct agcctactat gaagagatat tttagacagc   2820

tgtggcctac acgtgaaatg taaaaatata tatacatata ctataaaata tatatctaaa   2880

ttcccaagag agggtcaaaa gacctgttta gcattcagtg ttatatgtct tcctttcttt   2940

aaatcattaa aggatttaaa atgtcaaaaa aaaaaaaaaa                         2980
```

```
<210> SEQ ID NO 4
<211> LENGTH: 890
<212> TYPE: PRT
<213> ORGANISM: Homo sapiens

<400> SEQUENCE: 4

Met Glu Gly Gly Gly Lys Pro Asn Ser Ser Ser Asn Ser Arg Asp Asp
  1               5                  10                  15

Gly Asn Ser Val Phe Pro Ala Lys Ala Ser Ala Pro Gly Ala Gly Pro
             20                  25                  30

Ala Ala Ala Glu Lys Arg Leu Gly Thr Pro Pro Gly Gly Gly Gly Ala
         35                  40                  45

Gly Ala Lys Glu His Gly Asn Ser Val Cys Phe Lys Val Asp Gly Gly
     50                  55                  60

Gly Gly Gly Gly Gly Gly Gly Gly Gly Gly Glu Glu Pro Ala Gly Gly
 65                  70                  75                  80

Phe Glu Asp Ala Glu Gly Pro Arg Arg Gln Tyr Gly Phe Met Gln Arg
                 85                  90                  95

Gln Phe Thr Ser Met Leu Gln Pro Gly Val Asn Lys Phe Ser Leu Arg
            100                 105                 110

Met Phe Gly Ser Gln Lys Ala Val Glu Lys Glu Gln Glu Arg Val Lys
        115                 120                 125

Thr Ala Gly Phe Trp Ile Ile His Pro Tyr Ser Asp Phe Arg Phe Tyr
    130                 135                 140

Trp Asp Leu Ile Met Leu Ile Met Met Val Gly Asn Leu Val Ile Ile
145                 150                 155                 160

Pro Val Gly Ile Thr Phe Phe Thr Glu Gln Thr Thr Thr Pro Trp Ile
                165                 170                 175

Ile Phe Asn Val Ala Ser Asp Thr Val Phe Leu Leu Asp Leu Ile Met
```

-continued

```
            180                 185                 190

Asn Phe Arg Thr Gly Thr Val Asn Glu Asp Ser Ser Glu Ile Ile Leu
        195                 200                 205

Asp Pro Lys Val Ile Lys Met Asn Tyr Leu Lys Ser Trp Phe Val Val
    210                 215                 220

Asp Phe Ile Ser Ser Ile Pro Val Asp Tyr Ile Phe Leu Ile Val Glu
225                 230                 235                 240

Lys Gly Met Asp Ser Glu Val Tyr Lys Thr Ala Arg Ala Leu Arg Ile
                245                 250                 255

Val Arg Phe Thr Lys Ile Leu Ser Leu Leu Arg Leu Leu Arg Leu Ser
            260                 265                 270

Arg Leu Ile Arg Tyr Ile His Gln Trp Glu Glu Ile Phe His Met Thr
        275                 280                 285

Tyr Asp Leu Ala Ser Ala Val Val Arg Ile Phe Asn Leu Ile Gly Met
    290                 295                 300

Met Leu Leu Leu Cys His Trp Asp Gly Cys Leu Gln Phe Leu Val Pro
305                 310                 315                 320

Leu Leu Gln Asp Phe Pro Pro Asp Cys Trp Val Ser Leu Asn Glu Met
                325                 330                 335

Val Asn Asp Ser Trp Gly Lys Gln Tyr Ser Tyr Ala Leu Phe Lys Ala
            340                 345                 350

Met Ser His Met Leu Cys Ile Gly Tyr Gly Ala Gln Ala Pro Val Ser
        355                 360                 365

Met Ser Asp Leu Trp Ile Thr Met Leu Ser Met Ile Val Gly Ala Thr
    370                 375                 380

Cys Tyr Ala Met Phe Val Gly His Ala Thr Ala Leu Ile Gln Ser Leu
385                 390                 395                 400

Asp Ser Ser Arg Arg Gln Tyr Gln Glu Lys Tyr Lys Gln Val Glu Gln
                405                 410                 415

Tyr Met Ser Phe His Lys Leu Pro Ala Asp Met Arg Gln Lys Ile His
            420                 425                 430

Asp Tyr Tyr Glu His Arg Tyr Gln Gly Lys Ile Phe Asp Glu Glu Asn
        435                 440                 445

Ile Leu Asn Glu Leu Asn Asp Pro Leu Arg Glu Glu Ile Val Asn Phe
    450                 455                 460

Asn Cys Arg Lys Leu Val Ala Thr Met Pro Leu Phe Ala Asn Ala Asp
465                 470                 475                 480

Pro Asn Phe Val Thr Ala Met Leu Ser Lys Leu Arg Phe Glu Val Phe
                485                 490                 495

Gln Pro Gly Asp Tyr Ile Ile Arg Glu Gly Ala Val Gly Lys Lys Met
            500                 505                 510

Tyr Phe Ile Gln His Gly Val Ala Gly Val Ile Thr Lys Ser Ser Lys
        515                 520                 525

Glu Met Lys Leu Thr Asp Gly Ser Tyr Phe Gly Glu Ile Cys Leu Leu
    530                 535                 540

Thr Lys Gly Arg Arg Thr Ala Ser Val Arg Ala Asp Thr Tyr Cys Arg
545                 550                 555                 560

Leu Tyr Ser Leu Ser Val Asp Asn Phe Asn Glu Val Leu Glu Glu Tyr
                565                 570                 575

Pro Met Met Arg Arg Ala Phe Glu Thr Val Ala Ile Asp Arg Leu Asp
            580                 585                 590

Arg Ile Gly Lys Lys Asn Ser Ile Leu Leu Gln Lys Phe Gln Lys Asp
        595                 600                 605
```

-continued

```
Leu Asn Thr Gly Val Phe Asn Asn Gln Glu Asn Glu Ile Leu Lys Gln
    610                 615                 620

Ile Val Lys His Asp Arg Glu Met Val Gln Ala Ile Ala Pro Ile Asn
625                 630                 635                 640

Tyr Pro Gln Met Thr Thr Leu Asn Ser Thr Ser Ser Thr Thr Thr Pro
                645                 650                 655

Thr Ser Arg Met Arg Thr Gln Ser Pro Pro Val Tyr Thr Ala Thr Ser
            660                 665                 670

Leu Ser His Ser Asn Leu His Ser Pro Ser Pro Ser Thr Gln Thr Pro
        675                 680                 685

Gln Pro Ser Ala Ile Leu Ser Pro Cys Ser Tyr Thr Thr Ala Val Cys
    690                 695                 700

Ser Pro Pro Val Gln Ser Pro Leu Ala Ala Arg Thr Phe His Tyr Ala
705                 710                 715                 720

Ser Pro Thr Ala Ser Gln Leu Ser Leu Met Gln Gln Gln Pro Gln Gln
                725                 730                 735

Gln Val Gln Gln Ser Gln Pro Pro Gln Thr Gln Pro Gln Gln Pro Ser
            740                 745                 750

Pro Gln Pro Gln Thr Pro Gly Ser Ser Thr Pro Lys Asn Glu Val His
        755                 760                 765

Lys Ser Thr Gln Ala Leu His Asn Thr Asn Leu Thr Arg Glu Val Arg
    770                 775                 780

Pro Leu Ser Ala Ser Gln Pro Ser Leu Pro His Glu Val Ser Thr Leu
785                 790                 795                 800

Ile Ser Arg Pro His Pro Thr Val Gly Glu Ser Leu Ala Ser Ile Pro
                805                 810                 815

Gln Pro Val Thr Ala Val Pro Gly Thr Gly Leu Gln Ala Gly Gly Arg
            820                 825                 830

Ser Thr Val Pro Gln Arg Val Thr Leu Phe Arg Gln Met Ser Ser Gly
        835                 840                 845

Ala Ile Pro Pro Asn Arg Gly Val Pro Pro Ala Pro Pro Pro Pro Ala
    850                 855                 860

Ala Ala Leu Pro Arg Glu Ser Ser Ser Val Leu Asn Thr Asp Pro Asp
865                 870                 875                 880

Ala Glu Lys Pro Arg Phe Ala Ser Asn Leu
                885                 890


<210> SEQ ID NO 5
<211> LENGTH: 2791
<212> TYPE: DNA
<213> ORGANISM: Homo sapiens

<400> SEQUENCE: 5

ccgtcgccgg ccgcgtcctc cgggcatgga aggaggcggc aagcccaact cttcgtctaa      60

cagccgggac gatggcaaca gcgtcttccc cgccaaggcg tccgcgacgg gcgcggggcc     120

ggccgcggcc gagaagcgcc tgggcacccc gccggggggc ggcggggccg gcgcgaagga     180

gcacggcaac tccgtgtgct tcaaggtgga cggcggtggc ggcggtggcg gcggcggcgg     240

cggcggcgag gagccggcgg ggggcttcga agacgccgag gggccccggc ggcagtacgg     300

cttcatgcag aggcagttca cctccatgct gcagcccggg gtcaacaaat tctccctccg     360

catgtttggg agccagaagg cggtggaaaa ggagcaggaa agggttaaaa ctgcaggctt     420

ctggattatc caccettaca gtgatttcag gttttactgg gatttaataa tgcttataat     480
```

-continued

```
gatggttgga aatctagtca tcataccagt tggaatcaca ttctttacag agcaaacaac    540
aacaccatgg attattttca atgtggcatc agatacagtt ttcctattgg acctgatcat    600
gaattttagg actgggactg tcaatgaaga cagttctgaa atcatcctgg accccaaagt    660
gatcaagatg aattatttaa aaagctggtt tgtggttgac ttcatctcat ccatcccagt    720
ggattatatc tttcttattg tagaaaaagg aatggattct gaagtttaca agacagccag    780
ggcacttcgc attgtgaggt ttacaaaaat tctcagtctc ttgcgtttat tacgactttc    840
aaggttaatt agatacatac atcaatggga agagatattc cacatgacat atgatctcgc    900
cagtgcagtg gtgagaattt ttaatctcat cggcatgatg ctgctcctgt gccactggga    960
tggttgtctt cagttcttag taccactact gcaggacttc ccaccagatt gctgggtgtc   1020
tttaaatgaa atggttaatg attcttgggg aaagcagtat tcatacgcac tcttcaaagc   1080
tatgagtcac atgctgtgca ttgggtatgg agcccaagcc ccagtcagca tgtctgacct   1140
ctggattacc atgctgagca tgatcgtcgg ggccacctgc tatgccatgt ttgtcggcca   1200
tgccaccgct ttaatccagt ctctggattc ttcgaggcgg cagtatcaag agaagtataa   1260
gcaagtggaa caatacatgt cattccataa gttaccagct gatatgcgtc agaagataca   1320
tgattactat gaacacagat accaaggcaa aatctttgat gaggaaaata ttctcaatga   1380
actcaatgat cctctgagag aggagatagt caacttcaac tgtcggaaac tggtggctac   1440
aatgccttta tttgctaatg cggatcctaa ttttgtgact gccatgctga gcaagttgag   1500
atttgaggtg tttcaacctg gagattatat catacgagaa ggagccgtgg gtaaaaaaat   1560
gtatttcatt caacacggtg ttgctggtgt cattacaaaa tccagtaaag aaatgaagct   1620
gacagatggc tcttactttg gagagatttg cctgctgacc aaaggacgtc gtactgccag   1680
tgttcgagct gatacatatt gtcgtcttta ctcactttcc gtggacaatt tcaacgaggt   1740
cctggaggaa tatccaatga tgaggagagc ctttgagaca gttgccattg accgactaga   1800
tcgaatagga aagaaaaatt caattcttct gcaaaagttc cagaaggatc tgaacactgg   1860
tgttttcaac aatcaggaga acgaaatcct caagcagatt gtgaaacatg acagggagat   1920
ggtgcaggca atcgctccca tcaattatcc tcaaatgaca accctgaatt ccacatcgtc   1980
tactacgacc ccgacctccc gcatgaggac acaatctcca ccggtgtaca cagcgaccag   2040
cctgtctcac agcaacctgc acttccccag tcccagcaca cagaccccca agccatcagc   2100
catcctgtca ccctgctcca cgccgaaaaa tgaagtgcac aagagcacgc aggcgcttca   2160
caacaccaac ctgacccggg aagtcaggcc actctccgcc tcgcagccct cgctgcccca   2220
tgaggtgtcc actctgattt ccagacctca tcccactgtg ggcgagtccc tggcctccat   2280
ccctcaaccc gtgacggcgg tccccggaac gggccttcag gcagggggca ggagcactgt   2340
cccgcagcgc gtcaccctct tccgacagat gtcgtcggga gccatccccc cgaaccgagg   2400
agtccctcca gcaccccctc caccagcagc tgctcttcca agagaatctt cctcagtctt   2460
aaacacagac ccagacgcag aaaagccacg atttgcttca aatttatgat ccctgctgat   2520
tgtcaaagca gaaagaaata ctctcataaa ctgagactat actcagatct tattttattc   2580
tatctcctga tagatccctc tagcctacta tgaagagata ttttagacag ctgtggccta   2640
cacgtgaaat gtaaaaatat atatacatat actataaaat atatatctaa attcccaaga   2700
gagggtcaaa agacctgttt agcattcagt gttatatgtc ttcctttctt taaatcatta   2760
aaggatttaa aatgtcaaaa aaaaaaaaaa a                                  2791
```

-continued

<210> SEQ ID NO 6
<211> LENGTH: 827
<212> TYPE: PRT
<213> ORGANISM: Homo sapiens

<400> SEQUENCE: 6

```
Met Glu Gly Gly Gly Lys Pro Asn Ser Ser Ser Asn Ser Arg Asp Asp
  1               5                  10                  15

Gly Asn Ser Val Phe Pro Ala Lys Ala Ser Ala Thr Gly Ala Gly Pro
             20                  25                  30

Ala Ala Ala Glu Lys Arg Leu Gly Thr Pro Pro Gly Gly Gly Gly Ala
         35                  40                  45

Gly Ala Lys Glu His Gly Asn Ser Val Cys Phe Lys Val Asp Gly Gly
     50                  55                  60

Gly Gly Gly Gly Gly Gly Gly Gly Gly Gly Glu Glu Pro Ala Gly Gly
 65                  70                  75                  80

Phe Glu Asp Ala Glu Gly Pro Arg Arg Gln Tyr Gly Phe Met Gln Arg
                 85                  90                  95

Gln Phe Thr Ser Met Leu Gln Pro Gly Val Asn Lys Phe Ser Leu Arg
            100                 105                 110

Met Phe Gly Ser Gln Lys Ala Val Glu Lys Glu Gln Glu Arg Val Lys
        115                 120                 125

Thr Ala Gly Phe Trp Ile Ile His Pro Tyr Ser Asp Phe Arg Phe Tyr
    130                 135                 140

Trp Asp Leu Ile Met Leu Ile Met Met Val Gly Asn Leu Val Ile Ile
145                 150                 155                 160

Pro Val Gly Ile Thr Phe Phe Thr Glu Gln Thr Thr Thr Pro Trp Ile
                165                 170                 175

Ile Phe Asn Val Ala Ser Asp Thr Val Phe Leu Leu Asp Leu Ile Met
            180                 185                 190

Asn Phe Arg Thr Gly Thr Val Asn Glu Asp Ser Ser Glu Ile Ile Leu
        195                 200                 205

Asp Pro Lys Val Ile Lys Met Asn Tyr Leu Lys Ser Trp Phe Val Val
    210                 215                 220

Asp Phe Ile Ser Ser Ile Pro Val Asp Tyr Ile Phe Leu Ile Val Glu
225                 230                 235                 240

Lys Gly Met Asp Ser Glu Val Tyr Lys Thr Ala Arg Ala Leu Arg Ile
                245                 250                 255

Val Arg Phe Thr Lys Ile Leu Ser Leu Leu Arg Leu Leu Arg Leu Ser
            260                 265                 270

Arg Leu Ile Arg Tyr Ile His Gln Trp Glu Glu Ile Phe His Met Thr
        275                 280                 285

Tyr Asp Leu Ala Ser Ala Val Val Arg Ile Phe Asn Leu Ile Gly Met
    290                 295                 300

Met Leu Leu Leu Cys His Trp Asp Gly Cys Leu Gln Phe Leu Val Pro
305                 310                 315                 320

Leu Leu Gln Asp Phe Pro Pro Asp Cys Trp Val Ser Leu Asn Glu Met
                325                 330                 335

Val Asn Asp Ser Trp Gly Lys Gln Tyr Ser Tyr Ala Leu Phe Lys Ala
            340                 345                 350

Met Ser His Met Leu Cys Ile Gly Tyr Gly Ala Gln Ala Pro Val Ser
        355                 360                 365

Met Ser Asp Leu Trp Ile Thr Met Leu Ser Met Ile Val Gly Ala Thr
    370                 375                 380
```

-continued

```
Cys Tyr Ala Met Phe Val Gly His Ala Thr Ala Leu Ile Gln Ser Leu
385                 390                 395                 400

Asp Ser Ser Arg Arg Gln Tyr Gln Glu Lys Tyr Lys Gln Val Glu Gln
                405                 410                 415

Tyr Met Ser Phe His Lys Leu Pro Ala Asp Met Arg Gln Lys Ile His
            420                 425                 430

Asp Tyr Tyr Glu His Arg Tyr Gln Gly Lys Ile Phe Asp Glu Glu Asn
        435                 440                 445

Ile Leu Asn Glu Leu Asn Asp Pro Leu Arg Glu Glu Ile Val Asn Phe
    450                 455                 460

Asn Cys Arg Lys Leu Val Ala Thr Met Pro Leu Phe Ala Asn Ala Asp
465                 470                 475                 480

Pro Asn Phe Val Thr Ala Met Leu Ser Lys Leu Arg Phe Glu Val Phe
                485                 490                 495

Gln Pro Gly Asp Tyr Ile Ile Arg Glu Gly Ala Val Gly Lys Lys Met
            500                 505                 510

Tyr Phe Ile Gln His Gly Val Ala Gly Val Ile Thr Lys Ser Ser Lys
        515                 520                 525

Glu Met Lys Leu Thr Asp Gly Ser Tyr Phe Gly Glu Ile Cys Leu Leu
    530                 535                 540

Thr Lys Gly Arg Arg Thr Ala Ser Val Arg Ala Asp Thr Tyr Cys Arg
545                 550                 555                 560

Leu Tyr Ser Leu Ser Val Asp Asn Phe Asn Glu Val Leu Glu Glu Tyr
                565                 570                 575

Pro Met Met Arg Arg Ala Phe Glu Thr Val Ala Ile Asp Arg Leu Asp
            580                 585                 590

Arg Ile Gly Lys Lys Asn Ser Ile Leu Leu Gln Lys Phe Gln Lys Asp
        595                 600                 605

Leu Asn Thr Gly Val Phe Asn Asn Gln Glu Asn Glu Ile Leu Lys Gln
    610                 615                 620

Ile Val Lys His Asp Arg Glu Met Val Gln Ala Ile Ala Pro Ile Asn
625                 630                 635                 640

Tyr Pro Gln Met Thr Thr Leu Asn Ser Thr Ser Ser Thr Thr Thr Pro
                645                 650                 655

Thr Ser Arg Met Arg Thr Gln Ser Pro Pro Val Tyr Thr Ala Thr Ser
            660                 665                 670

Leu Ser His Ser Asn Leu His Phe Pro Ser Pro Ser Thr Gln Thr Pro
        675                 680                 685

Gln Pro Ser Ala Ile Leu Ser Pro Cys Ser Thr Pro Lys Asn Glu Val
    690                 695                 700

His Lys Ser Thr Gln Ala Leu His Asn Thr Asn Leu Thr Arg Glu Val
705                 710                 715                 720

Arg Pro Leu Ser Ala Ser Gln Pro Ser Leu Pro His Glu Val Ser Thr
                725                 730                 735

Leu Ile Ser Arg Pro His Pro Thr Val Gly Glu Ser Leu Ala Ser Ile
            740                 745                 750

Pro Gln Pro Val Thr Ala Val Pro Gly Thr Gly Leu Gln Ala Gly Gly
        755                 760                 765

Arg Ser Thr Val Pro Gln Arg Val Thr Leu Phe Arg Gln Met Ser Ser
    770                 775                 780

Gly Ala Ile Pro Pro Asn Arg Gly Val Pro Pro Ala Pro Pro Pro Pro
785                 790                 795                 800

Ala Ala Ala Leu Pro Arg Glu Ser Ser Ser Val Leu Asn Thr Asp Pro
```

-continued

```
                805                 810                 815

Asp Ala Glu Lys Pro Arg Phe Ala Ser Asn Leu
            820                 825


<210> SEQ ID NO 7
<211> LENGTH: 2980
<212> TYPE: DNA
<213> ORGANISM: Homo sapiens

<400> SEQUENCE: 7

ccgtcgccgg ccgcgtcctc cgggcatgga aggaggcggc aagcccaact cttcgtctaa     60

cagccgggac gatggcaaca gcgtcttccc cgccaaggcg tccgcgacgg gcgcggggcc    120

ggccgcggcc gagaagcgcc tgggcacccc gccggggggc ggcggggccg gcgcgaagga    180

gcacggcaac tccgtgtgct tcaaggtgga cggcggtggc ggcggtggcg gcggcggcgg    240

cggcggcgag gagccggcgg ggggcttcga agacgccgag ggccccggc ggcagtacgg    300

cttcatgcag aggcagttca cctccatgct gcagcccggg gtcaacaaat tctccctccg    360

catgtttggg agccagaagg cggtggaaaa ggagcaggaa agggttaaaa ctgcaggctt    420

ctggattatc caccccttaca gtgatttcag gttttactgg gatttaataa tgcttataat    480

gatggttgga aatctagtca tcataccagt tggaatcaca ttctttacag agcaaacaac    540

aacaccatgg attattttca atgtggcatc agatacagtt ttcctattgg acctgatcat    600

gaattttagg actgggactg tcaatgaaga cagttctgaa atcatcctgg accccaaagt    660

gatcaagatg aattatttaa aaagctggtt tgtggttgac ttcatctcat ccatcccagt    720

ggattatatc tttcttattg tagaaaaagg aatggattct gaagtttaca agacagccag    780

ggcacttcgc attgtgaggt ttacaaaaat tctcagtctc ttgcgtttat tacgactttc    840

aaggttaatt agatacatac atcaatggga agagatattc cacatgacat atgatctcgc    900

cagtgcagtg gtgagaattt ttaatctcat cggcatgatg ctgctcctgt gccactggga    960

tggttgtctt cagttcttag taccactact gcaggacttc ccaccagatt gctgggtgtc   1020

tttaaatgaa atggttaatg attcttgggg aaagcagtat tcatacgcac tcttcaaagc   1080

tatgagtcac atgctgtgca ttgggtatgg agcccaagcc ccagtcagca tgtctgacct   1140

ctggattacc atgctgagca tgatcgtcgg ggccacctgc tatgccatgt ttgtcggcca   1200

tgccaccgct ttaatccagt ctctggattc ttcgaggcgg cagtatcaag agaagtataa   1260

gcaagtggaa caatacatgt cattccataa gttaccagct gatatgcgtc agaagataca   1320

tgattactat gaacacagat accaaggcaa aatctttgat gaggaaaata ttctcaatga   1380

actcaatgat cctctgagag aggagatagt caacttcaac tgtcggaaac tggtggctac   1440

aatgccttta tttgctaatg cggatcctaa ttttgtgact gccatgctga gcaagttgag   1500

atttgaggtg tttcaacctg gagattatat catacgagaa ggagccgtgg gtaaaaaaat   1560

gtatttcatt caacacggtg ttgctggtgt cattacaaaa tccagtaaag aaatgaagct   1620

gacagatggc tcttactttg gagagatttg cctgctgacc aaaggacgtc gtactgccag   1680

tgttcgagct gatacatatt gtcgtcttta ctcactttcc gtggacaatt tcaacgaggt   1740

cctggaggaa tatccaatga tgaggagagc ctttgagaca gttgccattg accgactaga   1800

tcgaatagga aagaaaaatt caattcttct gcaaaagttc cagaaggatc tgaacactgg   1860

tgttttcaac aatcaggaga acgaaatcct caagcagatt gtgaaacatg acagggagat   1920

ggtgcaggca atcgctccca tcaattatcc tcaaatgaca accctgaatt ccacatcgtc   1980
```

-continued

```
tactacgacc ccgacctccc gcatgaggac acaatctcca ccggtgtaca cagcgaccag   2040

cctgtctcac agcaacctgc acttccccag tcccagcaca cagaccccc agccatcagc   2100

catcctgtca ccctgctcct acaccaccgc ggtctgcagc cctcctgtac agagccctct   2160

ggccgctcga actttccact atgcctcccc caccgcctcc cagctgtcac tcatgcaaca   2220

gcagccgcag cagcaggtac agcagtccca gccgccgcag actcagccac agcagccgtc   2280

cccgcagcca cagacacctg gcagctccac gccgaaaaat gaagtgcaca agagcacgca   2340

ggcgcttcac aacaccaacc tgacccggga agtcaggcca ctctccgcct cgcagccctc   2400

gctgccccat gaggtgtcca ctctgatttc cagacctcat cccactgtgg gcgagtccct   2460

ggcctccatc cctcaacccg tgacggcggt ccccggaacg ggccttcagg caggggggcag   2520

gagcactgtc ccgcagcgcg tcaccctctt ccgacagatg tcgtcgggag ccatcccccc   2580

gaaccgagga gtccctccag caccccctcc accagcagct gctcttccaa gagaatcttc   2640

ctcagtctta aacacagacc cagacgcaga aaagccacga tttgcttcaa atttatgatc   2700

cctgctgatt gtcaaagcag aaagaaatac tctcataaac tgagactata ctcagatctt   2760

attttattct atctcctgat agatccctct agcctactat gaagagatat tttagacagc   2820

tgtggcctac acgtgaaatg taaaaatata tatacatata ctataaaata tatatctaaa   2880

ttcccaagag agggtcaaaa gacctgttta gcattcagtg ttatatgtct tcctttcttt   2940

aaatcattaa aggatttaaa atgtcaaaaa aaaaaaaaaa                        2980
```

<210> SEQ ID NO 8
<211> LENGTH: 890
<212> TYPE: PRT
<213> ORGANISM: Homo sapiens

<400> SEQUENCE: 8

```
Met Glu Gly Gly Gly Lys Pro Asn Ser Ser Ser Asn Ser Arg Asp Asp
  1               5                  10                  15

Gly Asn Ser Val Phe Pro Ala Lys Ala Ser Ala Thr Gly Ala Gly Pro
             20                  25                  30

Ala Ala Ala Glu Lys Arg Leu Gly Thr Pro Pro Gly Gly Gly Gly Ala
         35                  40                  45

Gly Ala Lys Glu His Gly Asn Ser Val Cys Phe Lys Val Asp Gly Gly
     50                  55                  60

Gly Gly Gly Gly Gly Gly Gly Gly Gly Gly Glu Glu Pro Ala Gly Gly
 65                  70                  75                  80

Phe Glu Asp Ala Glu Gly Pro Arg Arg Gln Tyr Gly Phe Met Gln Arg
                 85                  90                  95

Gln Phe Thr Ser Met Leu Gln Pro Gly Val Asn Lys Phe Ser Leu Arg
            100                 105                 110

Met Phe Gly Ser Gln Lys Ala Val Glu Lys Glu Gln Glu Arg Val Lys
        115                 120                 125

Thr Ala Gly Phe Trp Ile Ile His Pro Tyr Ser Asp Phe Arg Phe Tyr
    130                 135                 140

Trp Asp Leu Ile Met Leu Ile Met Met Val Gly Asn Leu Val Ile Ile
145                 150                 155                 160

Pro Val Gly Ile Thr Phe Phe Thr Glu Gln Thr Thr Thr Pro Trp Ile
                165                 170                 175

Ile Phe Asn Val Ala Ser Asp Thr Val Phe Leu Leu Asp Leu Ile Met
            180                 185                 190

Asn Phe Arg Thr Gly Thr Val Asn Glu Asp Ser Ser Glu Ile Ile Leu
```

-continued

```
        195                 200                 205

Asp Pro Lys Val Ile Lys Met Asn Tyr Leu Lys Ser Trp Phe Val Val
    210                 215                 220

Asp Phe Ile Ser Ser Ile Pro Val Asp Tyr Ile Phe Leu Ile Val Glu
225                 230                 235                 240

Lys Gly Met Asp Ser Glu Val Tyr Lys Thr Ala Arg Ala Leu Arg Ile
                245                 250                 255

Val Arg Phe Thr Lys Ile Leu Ser Leu Leu Arg Leu Leu Arg Leu Ser
            260                 265                 270

Arg Leu Ile Arg Tyr Ile His Gln Trp Glu Glu Ile Phe His Met Thr
        275                 280                 285

Tyr Asp Leu Ala Ser Ala Val Val Arg Ile Phe Asn Leu Ile Gly Met
    290                 295                 300

Met Leu Leu Leu Cys His Trp Asp Gly Cys Leu Gln Phe Leu Val Pro
305                 310                 315                 320

Leu Leu Gln Asp Phe Pro Pro Asp Cys Trp Val Ser Leu Asn Glu Met
                325                 330                 335

Val Asn Asp Ser Trp Gly Lys Gln Tyr Ser Tyr Ala Leu Phe Lys Ala
            340                 345                 350

Met Ser His Met Leu Cys Ile Gly Tyr Gly Ala Gln Ala Pro Val Ser
        355                 360                 365

Met Ser Asp Leu Trp Ile Thr Met Leu Ser Met Ile Val Gly Ala Thr
    370                 375                 380

Cys Tyr Ala Met Phe Val Gly His Ala Thr Ala Leu Ile Gln Ser Leu
385                 390                 395                 400

Asp Ser Ser Arg Arg Gln Tyr Gln Glu Lys Tyr Lys Gln Val Glu Gln
                405                 410                 415

Tyr Met Ser Phe His Lys Leu Pro Ala Asp Met Arg Gln Lys Ile His
            420                 425                 430

Asp Tyr Tyr Glu His Arg Tyr Gln Gly Lys Ile Phe Asp Glu Glu Asn
        435                 440                 445

Ile Leu Asn Glu Leu Asn Asp Pro Leu Arg Glu Glu Ile Val Asn Phe
    450                 455                 460

Asn Cys Arg Lys Leu Val Ala Thr Met Pro Leu Phe Ala Asn Ala Asp
465                 470                 475                 480

Pro Asn Phe Val Thr Ala Met Leu Ser Lys Leu Arg Phe Glu Val Phe
                485                 490                 495

Gln Pro Gly Asp Tyr Ile Ile Arg Glu Gly Ala Val Gly Lys Lys Met
            500                 505                 510

Tyr Phe Ile Gln His Gly Val Ala Gly Val Ile Thr Lys Ser Ser Lys
        515                 520                 525

Glu Met Lys Leu Thr Asp Gly Ser Tyr Phe Gly Glu Ile Cys Leu Leu
    530                 535                 540

Thr Lys Gly Arg Arg Thr Ala Ser Val Arg Ala Asp Thr Tyr Cys Arg
545                 550                 555                 560

Leu Tyr Ser Leu Ser Val Asp Asn Phe Asn Glu Val Leu Glu Glu Tyr
                565                 570                 575

Pro Met Met Arg Arg Ala Phe Glu Thr Val Ala Ile Asp Arg Leu Asp
            580                 585                 590

Arg Ile Gly Lys Lys Asn Ser Ile Leu Leu Gln Lys Phe Gln Lys Asp
        595                 600                 605

Leu Asn Thr Gly Val Phe Asn Asn Gln Glu Asn Glu Ile Leu Lys Gln
    610                 615                 620
```

-continued

```
Ile Val Lys His Asp Arg Glu Met Val Gln Ala Ile Ala Pro Ile Asn
625                 630                 635                 640

Tyr Pro Gln Met Thr Thr Leu Asn Ser Thr Ser Ser Thr Thr Thr Pro
                645                 650                 655

Thr Ser Arg Met Arg Thr Gln Ser Pro Pro Val Tyr Thr Ala Thr Ser
            660                 665                 670

Leu Ser His Ser Asn Leu His Phe Pro Ser Pro Ser Thr Gln Thr Pro
        675                 680                 685

Gln Pro Ser Ala Ile Leu Ser Pro Cys Ser Tyr Thr Thr Ala Val Cys
    690                 695                 700

Ser Pro Pro Val Gln Ser Pro Leu Ala Ala Arg Thr Phe His Tyr Ala
705                 710                 715                 720

Ser Pro Thr Ala Ser Gln Leu Ser Leu Met Gln Gln Gln Pro Gln Gln
                725                 730                 735

Gln Val Gln Gln Ser Gln Pro Pro Gln Thr Gln Pro Gln Gln Pro Ser
            740                 745                 750

Pro Gln Pro Gln Thr Pro Gly Ser Ser Thr Pro Lys Asn Glu Val His
        755                 760                 765

Lys Ser Thr Gln Ala Leu His Asn Thr Asn Leu Thr Arg Glu Val Arg
    770                 775                 780

Pro Leu Ser Ala Ser Gln Pro Ser Leu Pro His Glu Val Ser Thr Leu
785                 790                 795                 800

Ile Ser Arg Pro His Pro Thr Val Gly Glu Ser Leu Ala Ser Ile Pro
                805                 810                 815

Gln Pro Val Thr Ala Val Pro Gly Thr Gly Leu Gln Ala Gly Gly Arg
            820                 825                 830

Ser Thr Val Pro Gln Arg Val Thr Leu Phe Arg Gln Met Ser Ser Gly
        835                 840                 845

Ala Ile Pro Pro Asn Arg Gly Val Pro Pro Ala Pro Pro Pro Pro Ala
    850                 855                 860

Ala Ala Leu Pro Arg Glu Ser Ser Ser Val Leu Asn Thr Asp Pro Asp
865                 870                 875                 880

Ala Glu Lys Pro Arg Phe Ala Ser Asn Leu
                885                 890
```

<210> SEQ ID NO 9
<211> LENGTH: 1046
<212> TYPE: DNA
<213> ORGANISM: Homo sapiens

<400> SEQUENCE: 9

```
cgagtaattt tgtgactgcc atgctgagca agttgagatt tgaggtgttt caacctggag     60

attatatcat acgagaagga gccgtgggta aaaaaatgta tttcattcaa cacggtgttg    120

ctggtgtcat tacaaaatcc agtaaagaaa tgaagctgac agatggctct tactttggag    180

agatttgcct gctgaccaaa ggacgtcgta ctgccagtgt tcgagctgat acatattgtc    240

gtctttactc actttccgtg gacaatttca acgaggtcct ggaggaatat ccaatgatga    300

ggagagcctt tgagacagtt gccattgacc gactagatcg aataggaaag aaaaattcaa    360

ttcttctgca aaagttccag aaggatctga acactggtgt tttcaacaat caggagaacg    420

aaatcctcaa gcagattgtg aaacatgaca gggagatggt gcaggcaatc gctcccatca    480

attatcctca aatgacaacc ctgaattcca catcgtctac tacgaccccg acctcccgca    540

tgaggacaca atctccaccg gtgtacacag cgaccagcct gtctcacagc aacctgcact    600
```

-continued

```
cccccagtcc cagcacacag accccccagc catcagccat cctgtcaccc tgctccacgc    660

cgaaaaatga agtgcacaag agcacgcagg cgcttcacaa caccaacctg acccgggaag    720

tcaggccact ctccgcctcg cagccctcgc tgccccatga ggtgtccact ctgatttcca    780

gacctcatcc cactgtgggc gagtccctgg cctccatccc tcaacccgtg acggcggtcc    840

ccggaacggg ccttcaggca gggggcagga gcactgtccc gcagcgcgtc accctcttcc    900

gacagatgtc gtcgggagcc atccccccga accgaggagt ccctccagca ccccctccac    960

cagcagctgc tcttccaaga gaatcttcct cagtcttaaa cacagaccca gacgcagaaa   1020

agccacgatt tgcttcaaat ttatga                                        1046


<210> SEQ ID NO 10
<211> LENGTH: 346
<212> TYPE: PRT
<213> ORGANISM: Homo sapiens

<400> SEQUENCE: 10

Asn Phe Val Thr Ala Met Leu Ser Lys Leu Arg Phe Glu Val Phe Gln
  1               5                  10                  15

Pro Gly Asp Tyr Ile Ile Arg Glu Gly Ala Val Gly Lys Lys Met Tyr
             20                  25                  30

Phe Ile Gln His Gly Val Ala Gly Val Ile Thr Lys Ser Ser Lys Glu
         35                  40                  45

Met Lys Leu Thr Asp Gly Ser Tyr Phe Gly Glu Ile Cys Leu Leu Thr
     50                  55                  60

Lys Gly Arg Arg Thr Ala Ser Val Arg Ala Asp Thr Tyr Cys Arg Leu
 65                  70                  75                  80

Tyr Ser Leu Ser Val Asp Asn Phe Asn Glu Val Leu Glu Glu Tyr Pro
                 85                  90                  95

Met Met Arg Arg Ala Phe Glu Thr Val Ala Ile Asp Arg Leu Asp Arg
            100                 105                 110

Ile Gly Lys Lys Asn Ser Ile Leu Leu Gln Lys Phe Gln Lys Asp Leu
        115                 120                 125

Asn Thr Gly Val Phe Asn Asn Gln Glu Asn Glu Ile Leu Lys Gln Ile
    130                 135                 140

Val Lys His Asp Arg Glu Met Val Gln Ala Ile Ala Pro Ile Asn Tyr
145                 150                 155                 160

Pro Gln Met Thr Thr Leu Asn Ser Thr Ser Ser Thr Thr Thr Pro Thr
                165                 170                 175

Ser Arg Met Arg Thr Gln Ser Pro Pro Val Tyr Thr Ala Thr Ser Leu
            180                 185                 190

Ser His Ser Asn Leu His Ser Pro Ser Pro Ser Thr Gln Thr Pro Gln
        195                 200                 205

Pro Ser Ala Ile Leu Ser Pro Cys Ser Thr Pro Lys Asn Glu Val His
    210                 215                 220

Lys Ser Thr Gln Ala Leu His Asn Thr Asn Leu Thr Arg Glu Val Arg
225                 230                 235                 240

Pro Leu Ser Ala Ser Gln Pro Ser Leu Pro His Glu Val Ser Thr Leu
                245                 250                 255

Ile Ser Arg Pro His Pro Thr Val Gly Glu Ser Leu Ala Ser Ile Pro
            260                 265                 270

Gln Pro Val Thr Ala Val Pro Gly Thr Gly Leu Gln Ala Gly Gly Arg
        275                 280                 285
```

-continued

```
Ser Thr Val Pro Gln Arg Val Thr Leu Phe Arg Gln Met Ser Ser Gly
    290                 295                 300

Ala Ile Pro Pro Asn Arg Gly Val Pro Pro Ala Pro Pro Pro Pro Ala
305                 310                 315                 320

Ala Ala Leu Pro Arg Glu Ser Ser Ser Val Leu Asn Thr Asp Pro Asp
                325                 330                 335

Ala Glu Lys Pro Arg Phe Ala Ser Asn Leu
            340                 345


<210> SEQ ID NO 11
<211> LENGTH: 1046
<212> TYPE: DNA
<213> ORGANISM: Homo sapiens

<400> SEQUENCE: 11

cgagtaattt tgtgactgcc atgctgagca agttgagatt tgaggtgttt caacctggag     60

attatatcat acgagaagga gccgtgggta aaaaaatgta tttcattcaa cacggtgttg    120

ctggtgtcat tacaaaatcc agtaaagaaa tgaagctgac agatggctct tactttggag    180

agatttgcct gctgaccaaa ggacgtcgta ctgccagtgt tcgagctgat acatattgtc    240

gtctttactc actttccgtg gacaatttca acgaggtcct ggaggaatat ccaatgatga    300

ggagagcctt tgagacagtt gccattgacc gactagatcg aataggaaag aaaaattcaa    360

ttcttctgca aaagttccag aaggatctga acactggtgt tttcaacaat caggagaacg    420

aaatcctcaa gcagattgtg aaacatgaca gggagatggt gcaggcaatc gctcccatca    480

attatcctca aatgacaacc ctgaattcca catcgtctac tacgaccccg acctcccgca    540

tgaggacaca atctccaccg gtgtacacag cgaccagcct gtctcacagc aacctgcact    600

tccccagtcc cagcacacag accccccagc catcagccat cctgtcaccc tgctccacgc    660

cgaaaaatga agtgcacaag agcacgcagg cgcttcacaa caccaacctg acccgggaag    720

tcaggccact ctccgcctcg cagccctcgc tgccccatga ggtgtccact ctgatttcca    780

gacctcatcc cactgtgggc gagtccctgg cctccatccc tcaacccgtg acggcggtcc    840

ccggaacggg ccttcaggca gggggcagga gcactgtccc gcagcgcgtc accctcttcc    900

gacagatgtc gtcgggagcc atcccccccga accgaggagt ccctccagca ccccctccac    960

cagcagctgc tcttccaaga gaatcttcct cagtcttaaa cacagaccca gacgcagaaa   1020

agccacgatt tgcttcaaat ttatga                                        1046


<210> SEQ ID NO 12
<211> LENGTH: 346
<212> TYPE: PRT
<213> ORGANISM: Homo sapiens

<400> SEQUENCE: 12

Asn Phe Val Thr Ala Met Leu Ser Lys Leu Arg Phe Glu Val Phe Gln
  1             5                  10                  15

Pro Gly Asp Tyr Ile Ile Arg Glu Gly Ala Val Gly Lys Lys Met Tyr
             20                  25                  30

Phe Ile Gln His Gly Val Ala Gly Val Ile Thr Lys Ser Ser Lys Glu
         35                  40                  45

Met Lys Leu Thr Asp Gly Ser Tyr Phe Gly Glu Ile Cys Leu Leu Thr
     50                  55                  60

Lys Gly Arg Arg Thr Ala Ser Val Arg Ala Asp Thr Tyr Cys Arg Leu
 65                  70                  75                  80
```

-continued

```
Tyr Ser Leu Ser Val Asp Asn Phe Asn Glu Val Leu Glu Glu Tyr Pro
                 85                  90                  95

Met Met Arg Arg Ala Phe Glu Thr Val Ala Ile Asp Arg Leu Asp Arg
            100                 105                 110

Ile Gly Lys Lys Asn Ser Ile Leu Leu Gln Lys Phe Gln Lys Asp Leu
        115                 120                 125

Asn Thr Gly Val Phe Asn Asn Gln Glu Asn Glu Ile Leu Lys Gln Ile
    130                 135                 140

Val Lys His Asp Arg Glu Met Val Gln Ala Ile Ala Pro Ile Asn Tyr
145                 150                 155                 160

Pro Gln Met Thr Thr Leu Asn Ser Thr Ser Ser Thr Thr Thr Pro Thr
                165                 170                 175

Ser Arg Met Arg Thr Gln Ser Pro Pro Val Tyr Thr Ala Thr Ser Leu
            180                 185                 190

Ser His Ser Asn Leu His Phe Pro Ser Pro Ser Thr Gln Thr Pro Gln
        195                 200                 205

Pro Ser Ala Ile Leu Ser Pro Cys Ser Thr Pro Lys Asn Glu Val His
    210                 215                 220

Lys Ser Thr Gln Ala Leu His Asn Thr Asn Leu Thr Arg Glu Val Arg
225                 230                 235                 240

Pro Leu Ser Ala Ser Gln Pro Ser Leu Pro His Glu Val Ser Thr Leu
                245                 250                 255

Ile Ser Arg Pro His Pro Thr Val Gly Glu Ser Leu Ala Ser Ile Pro
            260                 265                 270

Gln Pro Val Thr Ala Val Pro Gly Thr Gly Leu Gln Ala Gly Gly Arg
        275                 280                 285

Ser Thr Val Pro Gln Arg Val Thr Leu Phe Arg Gln Met Ser Ser Gly
    290                 295                 300

Ala Ile Pro Pro Asn Arg Gly Val Pro Pro Ala Pro Pro Pro Pro Ala
305                 310                 315                 320

Ala Ala Leu Pro Arg Glu Ser Ser Ser Val Leu Asn Thr Asp Pro Asp
                325                 330                 335

Ala Glu Lys Pro Arg Phe Ala Ser Asn Leu
            340                 345


<210> SEQ ID NO 13
<211> LENGTH: 153
<212> TYPE: DNA
<213> ORGANISM: Homo sapiens

<400> SEQUENCE: 13

ggcggcggcg gcgaggagcc ggcgggggc ttcgaagacg ccgaggggcc ccggcggcag      60

tacggcttca tgcagaggca gttcacctcc atgctgcagc ccggggtcaa caaattctcc    120

ctccgcatgt ttgggagcca gaaggcggtg gaa                                 153


<210> SEQ ID NO 14
<211> LENGTH: 452
<212> TYPE: DNA
<213> ORGANISM: Homo sapiens

<400> SEQUENCE: 14

ccgtcgccgg ccgcgtcctc cgggcatgga aggaggcggc aagcccaact cttcgtctaa      60

cagccgggac gatggcaaca gcgtcttccc cgccaaggcg tccgcgccgg gcgcggggcc    120

ggccgcggcc gagaagcgcc tgggcacccc gccgggggc ggcggggccg gcgcgaagga    180
```

-continued gcacggcaac tccgtgtgct tcaaggtgga cggcggtggc ggcggtggcg gcggcggcgg 240
cggcggcgag gagccggcgg ggggcttcga agacgccgag gggccccggc ggcagtacgg 300
cttcatgcag aggcagttca cctccatgct gcagcccggg gtcaacaaat tctccctccg 360
catgtttggg agccagaagg cggtggaaaa ggagcaggaa agggttaaaa ctgcaggctt 420
ctggattatc cacccttaca gtgatttcag gt 452

<210> SEQ ID NO 15
<211> LENGTH: 452
<212> TYPE: DNA
<213> ORGANISM: Homo sapiens

<400> SEQUENCE: 15
ccgtcgccgg ccgcgtcctc cgggcatgga aggaggcggc aagcccaact cttcgtctaa 60
cagccgggac gatggcaaca gcgtcttccc cgccaaggcg tccgcgacgg gcgcggggcc 120
ggccgcggcc gagaagcgcc tgggcacccc gccgggggc ggcggggccg gcgcgaagga 180
gcacggcaac tccgtgtgct tcaaggtgga cggcggtggc ggcggtggcg gcggcggcgg 240
cggcggcgag gagccggcgg ggggcttcga agacgccgag gggccccggc ggcagtacgg 300
cttcatgcag aggcagttca cctccatgct gcagcccggg gtcaacaaat tctccctccg 360
catgtttggg agccagaagg cggtggaaaa ggagcaggaa agggttaaaa ctgcaggctt 420
ctggattatc cacccttaca gtgatttcag gt 452

<210> SEQ ID NO 16
<211> LENGTH: 142
<212> TYPE: PRT
<213> ORGANISM: Homo sapiens

<400> SEQUENCE: 16

Met Glu Gly Gly Gly Lys Pro Asn Ser Ser Ser Asn Ser Arg Asp Asp
1 5 10 15

Gly Asn Ser Val Phe Pro Ala Lys Ala Ser Ala Pro Gly Ala Gly Pro
20 25 30

Ala Ala Ala Glu Lys Arg Leu Gly Thr Pro Pro Gly Gly Gly Gly Ala
35 40 45

Gly Ala Lys Glu His Gly Asn Ser Val Cys Phe Lys Val Asp Gly Gly
50 55 60

Gly Gly Gly Gly Gly Gly Gly Gly Gly Gly Glu Glu Pro Ala Gly Gly
65 70 75 80

Phe Glu Asp Ala Glu Gly Pro Arg Arg Gln Tyr Gly Phe Met Gln Arg
85 90 95

Gln Phe Thr Ser Met Leu Gln Pro Gly Val Asn Lys Phe Ser Leu Arg
100 105 110

Met Phe Gly Ser Gln Lys Ala Val Glu Lys Glu Gln Glu Arg Val Lys
115 120 125

Thr Ala Gly Phe Trp Ile Ile His Pro Tyr Ser Asp Phe Arg
130 135 140

<210> SEQ ID NO 17
<211> LENGTH: 142
<212> TYPE: PRT
<213> ORGANISM: Homo sapiens

<400> SEQUENCE: 17

Met Glu Gly Gly Gly Lys Pro Asn Ser Ser Ser Asn Ser Arg Asp Asp
1 5 10 15

-continued

```
Gly Asn Ser Val Phe Pro Ala Lys Ala Ser Ala Thr Gly Ala Gly Pro
             20                  25                  30

Ala Ala Ala Glu Lys Arg Leu Gly Thr Pro Pro Gly Gly Gly Gly Ala
         35                  40                  45

Gly Ala Lys Glu His Gly Asn Ser Val Cys Phe Lys Val Asp Gly Gly
     50                  55                  60

Gly Gly Gly Gly Gly Gly Gly Gly Gly Gly Glu Glu Pro Ala Gly Gly
 65                  70                  75                  80

Phe Glu Asp Ala Glu Gly Pro Arg Arg Gln Tyr Gly Phe Met Gln Arg
                 85                  90                  95

Gln Phe Thr Ser Met Leu Gln Pro Gly Val Asn Lys Phe Ser Leu Arg
            100                 105                 110

Met Phe Gly Ser Gln Lys Ala Val Glu Lys Glu Gln Glu Arg Val Lys
        115                 120                 125

Thr Ala Gly Phe Trp Ile Ile His Pro Tyr Ser Asp Phe Arg
    130                 135                 140
```

<210> SEQ ID NO 18
<211> LENGTH: 614
<212> TYPE: DNA
<213> ORGANISM: Homo sapiens

<400> SEQUENCE: 18

```
aaccctgaat tccacatcgt ctactacgac cccgacctcc cgcatgagga cacaatctcc      60

accggtgtac acagcgacca gcctgtctca cagcaacctg cactccccca gtcccagcac     120

acagaccccc cagccatcag ccatcctgtc accctgctcc tacaccaccg cggtctgcag     180

ccctcctgta cagagccctc tggccgctcg aactttccac tatgcctccc ccaccgcctc     240

ccagctgtca ctcatgcaac agcagccgca gcagcaggta cagcagtccc agccgccgca     300

gactcagcca cagcagccgt ccccgcagcc acagacacct ggcagctcca cgccgaaaaa     360

tgaagtgcac aagagcacgc aggcgcttca caacaccaac ctgacccggg aagtcaggcc     420

actctccgcc tcgcagccct cgctgcccca tgaggtgtcc actctgattt ccagacctca     480

tcccactgtg ggcgagtccc tggcctccat ccctcaaccc gtgacggcgg tccccggaac     540

gggccttcag gcaggggcca ggagcactgt cccgcagcgc gtcaccctct tccgacagat     600

gtcgtcggga gcca                                                      614
```

<210> SEQ ID NO 19
<211> LENGTH: 1873
<212> TYPE: DNA
<213> ORGANISM: Homo sapiens

<400> SEQUENCE: 19

```
tgctgcagcc cggggtcaac aaattctccc tccgcatgtt tgggagccag aaggcggtgg      60

aaaaggagca ggaaagggtt aaaactgcag gcttctggat tatccaccct tacagtgatt     120

tcaggtttta ctgggattta ataatgctta taatgatggt tggaaatcta gtcatcatac     180

cagttggaat cacattcttt acagagcaaa caacaacacc atggattatt ttcaatgtgg     240

catcagatac agttttccta ttggacctga tcatgaattt taggactggg actgtcaatg     300

aagacagttc tgaaatcatc ctggacccca aagtgatcaa gatgaattat ttaaaaagct     360

ggtttgtggt tgacttcatc tcatccatcc cagtggatta tatctttctt attgtagaaa     420

aaggaatgga ttctgaagtt tacaagacag ccagggcact tcgcattgtg aggtttacaa     480
```

-continued

```
aaattctcag tctcttgcgt ttattacgac tttcaaggtt aattagatac atacatcaat    540

gggaagagat attccacatg acatatgatc tcgccagtgc agtggtgaga atttttaatc    600

tcatcggcat gatgctgctc ctgtgccact gggatggttg tcttcagttc ttagtaccac    660

tactgcagga cttcccacca gattgctggg tgtctttaaa tgaaatggtt aatgattctt    720

ggggaaagca gtattcatac gcactcttca aagctatgag tcacatgctg tgcattgggt    780

atggagccca agccccagtc agcatgtctg acctctggat taccatgctg agcatgatcg    840

tcggggccac ctgctatgcc atgtttgtcg gccatgccac cgctttaatc cagtctctgg    900

attcttcgag gcggcagtat caagagaagt ataagcaagt ggaacaatac atgtcattcc    960

ataagttacc agctgatatg cgtcagaaga tacatgatta ctatgaacac agataccaag   1020

gcaaaatctt tgatgaggaa aatattctca atgaactcaa tgatcctctg agagaggaga   1080

tagtcaactt caactgtcgg aaactggtgg ctacaatgcc tttatttgct aatgcggatc   1140

ctaattttgt gactgccatg ctgagcaagt tgagatttga ggtgtttcaa cctggagatt   1200

atatcatacg agaaggagcc gtgggtaaaa aaatgtattt cattcaacac ggtgttgctg   1260

gtgtcattac aaaatccagt aaagaaatga agctgacaga tggctcttac tttggagaga   1320

tttgcctgct gaccaaagga cgtcgtactg ccagtgttcg agctgataca tattgtcgtc   1380

tttactcact ttccgtggac aatttcaacg aggtcctgga ggaatatcca atgatgagga   1440

gagcctttga gacagttgcc attgaccgac tagatcgaat aggaaagaaa aattcaattc   1500

ttctgcaaaa gttccagaag gatctgaaca ctggtgtttt caacaatcag gagaacgaaa   1560

tcctcaagca gattgtgaaa catgacaggg agatggtgca ggcaatcgct cccatcaatt   1620

atcctcaaat gacaaccctg aattccacat cgtctactac gacccggacc tcccgcatga   1680

ggacacaatc tccaccggtg tacacagcga ccagcctgtc tcacagcaac ctgcactccc   1740

ccagtcccag cacacagacc ccccagccat cagccatcct gtcaccctgc tcctacacca   1800

ccgcggtctg cagccctcct gtacagagcc ctctggccgc tcgaactttc cactatgcct   1860

cccccaccgc ctc                                                      1873
```

```
<210> SEQ ID NO 20
<211> LENGTH: 1873
<212> TYPE: DNA
<213> ORGANISM: Homo sapiens

<400> SEQUENCE: 20

tgctgcagcc cggggtcaac aaattctccc tccgcatgtt tgggagccag aaggcggtgg     60

aaaaggagca ggaaagggtt aaaactgcag gcttctggat tatccaccct tacagtgatt    120

tcaggtttta ctgggattta ataatgctta taatgatggt tggaaatcta gtcatcatac    180

cagttggaat cacattcttt acagagcaaa caacaacacc atggattatt ttcaatgtgg    240

catcagatac agttttccta ttggacctga tcatgaattt taggactggg actgtcaatg    300

aagacagttc tgaaatcatc ctggacccca aagtgatcaa gatgaattat ttaaaaagct    360

ggtttgtggt tgacttcatc tcatccatcc cagtggatta tatctttctt attgtagaaa    420

aaggaatgga ttctgaagtt tacaagacag ccagggcact tcgcattgtg aggtttacaa    480

aaattctcag tctcttgcgt ttattacgac tttcaaggtt aattagatac atacatcaat    540

gggaagagat attccacatg acatatgatc tcgccagtgc agtggtgaga atttttaatc    600

tcatcggcat gatgctgctc ctgtgccact gggatggttg tcttcagttc ttagtaccac    660

tactgcagga cttcccacca gattgctggg tgtctttaaa tgaaatggtt aatgattctt    720
```

-continued

```
ggggaaagca gtattcatac gcactcttca aagctatgag tcacatgctg tgcattgggt    780

atggagccca agccccagtc agcatgtctg acctctggat taccatgctg agcatgatcg    840

tcggggccac ctgctatgcc atgtttgtcg gccatgccac cgctttaatc cagtctctgg    900

attcttcgag gcggcagtat caagagaagt ataagcaagt ggaacaatac atgtcattcc    960

ataagttacc agctgatatg cgtcagaaga tacatgatta ctatgaacac agataccaag   1020

gcaaaatctt tgatgaggaa aatattctca atgaactcaa tgatcctctg agagaggaga   1080

tagtcaactt caactgtcgg aaactggtgg ctacaatgcc tttatttgct aatgcggatc   1140

ctaattttgt gactgccatg ctgagcaagt tgagatttga ggtgtttcaa cctggagatt   1200

atatcatacg agaaggagcc gtgggtaaaa aaatgtattt cattcaacac ggtgttgctg   1260

gtgtcattac aaaatccagt aaagaaatga agctgacaga tggctcttac tttggagaga   1320

tttgcctgct gaccaaagga cgtcgtactg ccagtgttcg agctgataca tattgtcgtc   1380

tttactcact ttccgtggac aatttcaacg aggtcctgga ggaatatcca atgatgagga   1440

gagcctttga gacagttgcc attgaccgac tagatcgaat aggaaagaaa aattcaattc   1500

ttctgcaaaa gttccagaag gatctgaaca ctggtgtttt caacaatcag gagaacgaaa   1560

tcctcaagca gattgtgaaa catgacaggg agatggtgca ggcaatcgct cccatcaatt   1620

atcctcaaat gacaaccctg aattccacat cgtctactac gaccccgacc tcccgcatga   1680

ggacacaatc tccaccggtg tacacagcga ccagcctgtc tcacagcaac ctgcacttcc   1740

ccagtcccag cacacagacc ccccagccat cagccatcct gtcaccctgc tcctacacca   1800

ccgcggtctg cagccctcct gtacagagcc ctctggccgc tcgaactttc cactatgcct   1860

cccccaccgc ctc                                                      1873
```

<210> SEQ ID NO 21
<211> LENGTH: 627
<212> TYPE: DNA
<213> ORGANISM: Homo sapiens

<400> SEQUENCE: 21

```
cccgggaagt caggccactc tccgcctcgc agccctcgct gccccatgag gtgtccactc     60

tgatttccag acctcatccc actgtgggcg agtccctggc ctccatccct caacccgtga    120

cggcggtccc cggaacgggc cttcaggcag ggggcaggag cactgtcccg cagcgcgtca    180

ccctcttccg acagatgtcg tcgggagcca tccccccgaa ccgaggagtc cctccagcac    240

cccctccacc agcagctgct cttccaagag aatcttcctc agtcttaaac acagacccag    300

acgcagaaaa gccacgattt gcttcaaatt tatgatccct gctgattgtc aaagcagaaa    360

gaaatactct cataaactga gactatactc agatcttatt ttattctatc tcctgataga    420

tccctctagc ctactatgaa gagatatttt agacagctgt ggcctacacg tgaaatgtaa    480

aaatatatat acatatacta taaaatatat atctaaattc ccaagagagg gtcaaaagac    540

ctgtttagca ttcagtgtta tatgtcttcc tttctttaaa tcattaaagg atttaaaatg    600

tcaaaaaaaa aaaaaaaggg cggccgc                                        627
```

<210> SEQ ID NO 22
<211> LENGTH: 2484
<212> TYPE: DNA
<213> ORGANISM: Homo sapiens

<400> SEQUENCE: 22

-continued

```
atggaaggag gcggcaagcc caactcttcg tctaacagcc gggacgatgg caacagcgtc     60
ttccccgcca aggcgtccgc gccgggcgcg gggccggccg cggccgagaa gcgcctgggc    120
accccgccgg ggggcggcgg ggccggcgcg aaggagcacg gcaactccgt gtgcttcaag    180
gtggacggcg gtggcggcgg tggcggcggc ggcggcggcg gcgaggagcc ggcggggggc    240
ttcgaagacg ccgaggggcc ccggcggcag tacggcttca tgcagaggca gttcacctcc    300
atgctgcagc ccggggtcaa caaattctcc ctccgcatgt ttgggagcca gaaggcggtg    360
gaaaaggagc aggaaagggt taaaactgca ggcttctgga ttatccaccc ttacagtgat    420
ttcaggtttt actgggattt aataatgctt ataatgatgg ttggaaatct agtcatcata    480
ccagttggaa tcacattctt tacagagcaa acaacaacac catggattat tttcaatgtg    540
gcatcagata cagttttcct attggacctg atcatgaatt ttaggactgg gactgtcaat    600
gaagacagtt ctgaaatcat cctggacccc aaagtgatca agatgaatta tttaaaaagc    660
tggtttgtgg ttgacttcat ctcatccatc ccagtggatt atatctttct tattgtagaa    720
aaaggaatgg attctgaagt ttacaagaca gccagggcac ttcgcattgt gaggtttaca    780
aaaattctca gtctcttgcg tttattacga ctttcaaggt taattagata catacatcaa    840
tgggaagaga tattccacat gacatatgat ctcgccagtg cagtggtgag aatttttaat    900
ctcatcggca tgatgctgct cctgtgccac tgggatggtt gtcttcagtt cttagtacca    960
ctactgcagg acttcccacc agattgctgg gtgtctttaa atgaaatggt taatgattct   1020
tggggaaagc agtattcata cgcactcttc aaagctatga gtcacatgct gtgcattggg   1080
tatggagccc aagccccagt cagcatgtct gacctctgga ttaccatgct gagcatgatc   1140
gtcggggcca cctgctatgc catgtttgtc ggccatgcca ccgctttaat ccagtctctg   1200
gattcttcga ggcggcagta tcaagagaag tataagcaag tggaacaata catgtcattc   1260
cataagttac cagctgatat gcgtcagaag atacatgatt actatgaaca cagataccaa   1320
ggcaaaatct ttgatgagga aaatattctc aatgaactca atgatcctct gagagaggag   1380
atagtcaact tcaactgtcg gaaactggtg gctacaatgc ctttatttgc taatgcggat   1440
cctaattttg tgactgccat gctgagcaag ttgagatttg aggtgtttca acctggagat   1500
tatatcatac gagaaggagc cgtgggtaaa aaaatgtatt tcattcaaca cggtgttgct   1560
ggtgtcatta caaaatccag taaagaaatg aagctgacag atggctctta ctttggagag   1620
atttgcctgc tgaccaaagg acgtcgtact gccagtgttc gagctgatac atattgtcgt   1680
ctttactcac tttccgtgga caatttcaac gaggtcctgg aggaatatcc aatgatgagg   1740
agagcctttg agacagttgc cattgaccga ctagatcgaa taggaaagaa aaattcaatt   1800
cttctgcaaa agttccagaa ggatctgaac actggtgttt tcaacaatca ggagaacgaa   1860
atcctcaagc agattgtgaa acatgacagg gagatggtgc aggcaatcgc tcccatcaat   1920
tatcctcaaa tgacaaccct gaattccaca tcgtctacta cgaccccgac ctcccgcatg   1980
aggacacaat ctccaccggt gtacacagcg accagcctgt ctcacagcaa cctgcactcc   2040
cccagtccca gcacacagac cccccagcca tcagccatcc tgtcaccctg ctccacgccg   2100
aaaaatgaag tgcacaagag cacgcaggcg cttcacaaca ccaacctgac ccgggaagtc   2160
aggccactct ccgcctcgca gccctcgctg ccccatgagg tgtccactct gatttccaga   2220
cctcatccca ctgtgggcga gtccctggcc tccatccctc aacccgtgac ggcggtcccc   2280
ggaacgggcc ttcaggcagg gggcaggagc actgtcccgc agcgcgtcac cctcttccga   2340
cagatgtcgt cgggagccat ccccccgaac cgaggagtcc ctccagcacc ccctccacca   2400
```

-continued

```
gcagctgctc ttccaagaga atcttcctca gtcttaaaca cagacccaga cgcagaaaag   2460

ccacgatttg cttcaaattt atga                                           2484


<210> SEQ ID NO 23
<211> LENGTH: 2673
<212> TYPE: DNA
<213> ORGANISM: Homo sapiens

<400> SEQUENCE: 23

atggaaggag gcggcaagcc caactcttcg tctaacagcc gggacgatgg caacagcgtc     60

ttccccgcca aggcgtccgc gccgggcgcg gggccggccg cggccgagaa gcgcctgggc    120

accccgccgg ggggcggcgg ggccggcgcg aaggagcacg gcaactccgt gtgcttcaag    180

gtggacggcg gtggcggcgg tggcggcggc ggcggcggcg gcgaggagcc ggcggggggc    240

ttcgaagacg ccgaggggcc ccggcggcag tacggcttca tgcagaggca gttcacctcc    300

atgctgcagc ccggggtcaa caaattctcc ctccgcatgt ttgggagcca gaaggcggtg    360

gaaaaggagc aggaaagggt taaaactgca ggcttctgga ttatccaccc ttacagtgat    420

ttcaggtttt actgggattt aataatgctt ataatgatgg ttggaaatct agtcatcata    480

ccagttggaa tcacattctt tacagagcaa acaacaacac catggattat tttcaatgtg    540

gcatcagata cagttttcct attggacctg atcatgaatt ttaggactgg gactgtcaat    600

gaagacagtt ctgaaatcat cctggacccc aaagtgatca agatgaatta tttaaaaagc    660

tggtttgtgg ttgacttcat ctcatccatc ccagtggatt atatctttct tattgtagaa    720

aaaggaatgg attctgaagt ttacaagaca gccagggcac ttcgcattgt gaggtttaca    780

aaaattctca gtctcttgcg tttattacga ctttcaaggt taattagata catacatcaa    840

tgggaagaga tattccacat gacatatgat ctcgccagtg cagtggtgag aatttttaat    900

ctcatcggca tgatgctgct cctgtgccac tgggatggtt gtcttcagtt cttagtacca    960

ctactgcagg acttcccacc agattgctgg gtgtctttaa atgaaatggt taatgattct   1020

tggggaaagc agtattcata cgcactcttc aaagctatga gtcacatgct gtgcattggg   1080

tatggagccc aagccccagt cagcatgtct gacctctgga ttaccatgct gagcatgatc   1140

gtcggggcca cctgctatgc catgtttgtc ggccatgcca ccgctttaat ccagtctctg   1200

gattcttcga ggcggcagta tcaagagaag tataagcaag tggaacaata catgtcattc   1260

cataagttac cagctgatat gcgtcagaag atacatgatt actatgaaca cagataccaa   1320

ggcaaaatct ttgatgagga aaatattctc aatgaactca atgatcctct gagagaggag   1380

atagtcaact tcaactgtcg gaaactggtg gctacaatgc ctttatttgc taatgcggat   1440

cctaattttg tgactgccat gctgagcaag ttgagatttg aggtgtttca acctggagat   1500

tatatcatac gagaaggagc cgtgggtaaa aaaatgtatt tcattcaaca cggtgttgct   1560

ggtgtcatta caaaatccag taaagaaatg aagctgacag atggctctta ctttggagag   1620

atttgcctgc tgaccaaagg acgtcgtact gccagtgttc gagctgatac atattgtcgt   1680

ctttactcac tttccgtgga caatttcaac gaggtcctgg aggaatatcc aatgatgagg   1740

agagcctttg agacagttgc cattgaccga ctagatcgaa taggaaagaa aaattcaatt   1800

cttctgcaaa agttccagaa ggatctgaac actggtgttt tcaacaatca ggagaacgaa   1860

atcctcaagc agattgtgaa acatgacagg gagatggtgc aggcaatcgc tcccatcaat   1920

tatcctcaaa tgacaaccct gaattccaca tcgtctacta cgaccccgac ctcccgcatg   1980
```

-continued aggacacaat ctccaccggt gtacacagcg accagcctgt ctcacagcaa cctgcactcc 2040
cccagtccca gcacacagac cccccagcca tcagccatcc tgtcaccctg ctcctacacc 2100
accgcggtct gcagccctcc tgtacagagc cctctggccg ctcgaacttt ccactatgcc 2160
tcccccaccg cctcccagct gtcactcatg caacagcagc cgcagcagca ggtacagcag 2220
tcccagccgc cgcagactca gccacagcag ccgtccccgc agccacagac acctggcagc 2280
tccacgccga aaaatgaagt gcacaagagc acgcaggcgc ttcacaacac caacctgacc 2340
cgggaagtca ggccactctc cgcctcgcag ccctcgctgc cccatgaggt gtccactctg 2400
atttccagac ctcatcccac tgtgggcgag tccctggcct ccatccctca acccgtgacg 2460
gcggtccccg gaacgggcct tcaggcaggg ggcaggagca ctgtcccgca gcgcgtcacc 2520
ctcttccgac agatgtcgtc gggagccatc cccccgaacc gaggagtccc tccagcaccc 2580
cctccaccag cagctgctct tccaagagaa tcttcctcag tcttaaacac agacccagac 2640
gcagaaaagc cacgatttgc ttcaaattta tga 2673

<210> SEQ ID NO 24
<211> LENGTH: 2484
<212> TYPE: DNA
<213> ORGANISM: Homo sapiens

<400> SEQUENCE: 24
atggaaggag gcggcaagcc caactcttcg tctaacagcc gggacgatgg caacagcgtc 60
ttccccgcca aggcgtccgc gacgggcgcg gggccggccg cggccgagaa gcgcctgggc 120
accccgccgg ggggcggcgg ggccggcgcg aaggagcacg gcaactccgt gtgcttcaag 180
gtggacggcg gtggcggcgg tggcggcggc ggcggcggcg gcgaggagcc ggcgggggc 240 ttcgaagacg ccgaggggcc ccggcggcag tacggcttca tgcagaggca gttcacctcc 300
atgctgcagc ccggggtcaa caaattctcc ctccgcatgt ttgggagcca gaaggcggtg 360
gaaaaggagc aggaaagggt taaaactgca ggcttctgga ttatccaccc ttacagtgat 420
ttcaggtttt actgggattt aataatgctt ataatgatgg ttggaaatct agtcatcata 480
ccagttggaa tcacattctt tacagagcaa acaacaacac catggattat tttcaatgtg 540
gcatcagata cagttttcct attggacctg atcatgaatt ttaggactgg gactgtcaat 600
gaagacagtt ctgaaatcat cctggacccc aaagtgatca agatgaatta tttaaaaagc 660
tggtttgtgg ttgacttcat ctcatccatc ccagtggatt atatctttct tattgtagaa 720
aaaggaatgg attctgaagt ttacaagaca gccagggcac ttcgcattgt gaggtttaca 780
aaaattctca gtctcttgcg tttattacga ctttcaaggt taattagata catacatcaa 840
tgggaagaga tattccacat gacatatgat ctcgccagtg cagtggtgag aatttttaat 900
ctcatcggca tgatgctgct cctgtgccac tgggatggtt gtcttcagtt cttagtacca 960
ctactgcagg acttcccacc agattgctgg gtgtctttaa atgaaatggt taatgattct 1020
tggggaaagc agtattcata cgcactcttc aaagctatga gtcacatgct gtgcattggg 1080
tatggagccc aagccccagt cagcatgtct gacctctgga ttaccatgct gagcatgatc 1140
gtcggggcca cctgctatgc catgtttgtc ggccatgcca ccgctttaat ccagtctctg 1200
gattcttcga ggcggcagta tcaagagaag tataagcaag tggaacaata catgtcattc 1260
cataagttac cagctgatat gcgtcagaag atacatgatt actatgaaca cagataccaa 1320
ggcaaaatct ttgatgagga aaatattctc aatgaactca atgatcctct gagagaggag 1380
atagtcaact tcaactgtcg gaaactggtg gctacaatgc ctttatttgc taatgcggat 1440

-continued

```
cctaattttg tgactgccat gctgagcaag ttgagatttg aggtgtttca acctggagat   1500

tatatcatac gagaaggagc cgtgggtaaa aaaatgtatt tcattcaaca cggtgttgct   1560

ggtgtcatta caaaatccag taaagaaatg aagctgacag atggctctta ctttggagag   1620

atttgcctgc tgaccaaagg acgtcgtact gccagtgttc gagctgatac atattgtcgt   1680

ctttactcac tttccgtgga caatttcaac gaggtcctgg aggaatatcc aatgatgagg   1740

agagcctttg agacagttgc cattgaccga ctagatcgaa taggaaagaa aaattcaatt   1800

cttctgcaaa agttccagaa ggatctgaac actggtgttt tcaacaatca ggagaacgaa   1860

atcctcaagc agattgtgaa acatgacagg gagatggtgc aggcaatcgc tcccatcaat   1920

tatcctcaaa tgacaaccct gaattccaca tcgtctacta cgaccccgac ctcccgcatg   1980

aggacacaat ctccaccggt gtacacagcg accagcctgt ctcacagcaa cctgcacttc   2040

cccagtccca gcacacagac cccccagcca tcagccatcc tgtcaccctg ctccacgccg   2100

aaaaatgaag tgcacaagag cacgcaggcg cttcacaaca ccaacctgac ccgggaagtc   2160

aggccactct ccgcctcgca gccctcgctg ccccatgagg tgtccactct gatttccaga   2220

cctcatccca ctgtgggcga gtccctggcc tccatccctc aacccgtgac ggcggtcccc   2280

ggaacgggcc ttcaggcagg gggcaggagc actgtcccgc agcgcgtcac cctcttccga   2340

cagatgtcgt cgggagccat ccccccgaac cgaggagtcc ctccagcacc ccctccacca   2400

gcagctgctc ttccaagaga atcttcctca gtcttaaaca cagacccaga cgcagaaaag   2460

ccacgatttg cttcaaattt atga                                           2484

<210> SEQ ID NO 25
<211> LENGTH: 2673
<212> TYPE: DNA
<213> ORGANISM: Homo sapiens

<400> SEQUENCE: 25

atggaaggag gcggcaagcc caactcttcg tctaacagcc gggacgatgg caacagcgtc     60

ttccccgcca aggcgtccgc gacgggcgcg gggccggccg cggccgagaa gcgcctgggc    120

accccgccgg ggggcggcgg ggccggcgcg aaggagcacg gcaactccgt gtgcttcaag    180

gtggacggcg gtggcggcgg tggcggcggc ggcggcggcg gcgaggagcc ggcgggggc    240

ttcgaagacg ccgaggggcc ccggcggcag tacggcttca tgcagaggca gttcacctcc    300

atgctgcagc ccggggtcaa caaattctcc ctccgcatgt ttgggagcca gaaggcggtg    360

gaaaaggagc aggaaagggt taaaactgca ggcttctgga ttatccaccc ttacagtgat    420

ttcaggtttt actgggattt aataatgctt ataatgatgg ttggaaatct agtcatcata    480

ccagttggaa tcacattctt tacagagcaa acaacaacac catggattat tttcaatgtg    540

gcatcagata cagttttcct attggacctg atcatgaatt ttaggactgg gactgtcaat    600

gaagacagtt ctgaaatcat cctggacccc aaagtgatca agatgaatta tttaaaaagc    660

tggtttgtgg ttgacttcat ctcatccatc ccagtggatt atatctttct tattgtagaa    720

aaaggaatgg attctgaagt ttacaagaca gccagggcac ttcgcattgt gaggtttaca    780

aaaattctca gtctcttgcg tttattacga ctttcaaggt taattagata catacatcaa    840

tgggaagaga tattccacat gacatatgat ctcgccagtg cagtggtgag aatttttaat    900

ctcatcggca tgatgctgct cctgtgccac tgggatggtt gtcttcagtt cttagtacca    960

ctactgcagg acttcccacc agattgctgg gtgtctttaa atgaaatggt taatgattct   1020
```

-continued

| | |
|---|---|
| tggggaaagc agtattcata cgcactcttc aaagctatga gtcacatgct gtgcattggg | 1080 |
| tatggagccc aagccccagt cagcatgtct gacctctgga ttaccatgct gagcatgatc | 1140 |
| gtcggggcca cctgctatgc catgtttgtc ggccatgcca ccgctttaat ccagtctctg | 1200 |
| gattcttcga ggcggcagta tcaagagaag tataagcaag tggaacaata catgtcattc | 1260 |
| cataagttac cagctgatat gcgtcagaag atacatgatt actatgaaca cagataccaa | 1320 |
| ggcaaaatct ttgatgagga aaatattctc aatgaactca atgatcctct gagagaggag | 1380 |
| atagtcaact tcaactgtcg gaaactggtg gctacaatgc ctttatttgc taatgcggat | 1440 |
| cctaattttg tgactgccat gctgagcaag ttgagatttg aggtgtttca acctggagat | 1500 |
| tatatcatac gagaaggagc cgtgggtaaa aaaatgtatt tcattcaaca cggtgttgct | 1560 |
| ggtgtcatta caaaatccag taaagaaatg aagctgacag atggctctta ctttggagag | 1620 |
| atttgcctgc tgaccaaagg acgtcgtact gccagtgttc gagctgatac atattgtcgt | 1680 |
| ctttactcac tttccgtgga caatttcaac gaggtcctgg aggaatatcc aatgatgagg | 1740 |
| agagcctttg agacagttgc cattgaccga ctagatcgaa taggaaagaa aaattcaatt | 1800 |
| cttctgcaaa agttccagaa ggatctgaac actggtgttt tcaacaatca ggagaacgaa | 1860 |
| atcctcaagc agattgtgaa acatgacagg gagatggtgc aggcaatcgc tcccatcaat | 1920 |
| tatcctcaaa tgacaaccct gaattccaca tcgtctacta cgaccccgac ctcccgcatg | 1980 |
| aggacacaat ctccaccggt gtacacagcg accagcctgt ctcacagcaa cctgcacttc | 2040 |
| cccagtccca gcacacagac cccccagcca tcagccatcc tgtcaccctg ctcctacacc | 2100 |
| accgcggtct gcagccctcc tgtacagagc cctctggccg ctcgaacttt ccactatgcc | 2160 |
| tcccccaccg cctcccagct gtcactcatg caacagcagc cgcagcagca ggtacagcag | 2220 |
| tcccagccgc cgcagactca gccacagcag ccgtccccgc agccacagac acctggcagc | 2280 |
| tccacgccga aaaatgaagt gcacaagagc acgcaggcgc ttcacaacac caacctgacc | 2340 |
| cgggaagtca ggccactctc cgcctcgcag ccctcgctgc cccatgaggt gtccactctg | 2400 |
| atttccagac ctcatcccac tgtgggcgag tccctggcct ccatccctca acccgtgacg | 2460 |
| gcggtccccg gaacgggcct tcaggcaggg ggcaggagca ctgtcccgca gcgcgtcacc | 2520 |
| ctcttccgac agatgtcgtc gggagccatc cccccgaacc gaggagtccc tccagcaccc | 2580 |
| cctccaccag cagctgctct tccaagagaa tcttcctcag tcttaaacac agacccagac | 2640 |
| gcagaaaagc cacgatttgc ttcaaattta tga | 2673 |